(12) United States Patent
Muthuchidambaram et al.

(10) Patent No.: US 12,343,038 B2
(45) Date of Patent: Jul. 1, 2025

(54) PINCH-TO-RELEASE CANNULA DEPTH LIMITER

(71) Applicant: Cilag GmbH International, Zug (CH)

(72) Inventors: Arunachalam Muthuchidambaram, Madurai (IN); Arunkumar Radhakrishnan, B. Komarapalayam (IN); Rushikesh Shrikant Suryawanshi, Patan (IN); Dhivakar A, Suryawanshi, Chengalpattu (IN); Cameron D. McLain, Deer Park, OH (US); Lauren M. Valente, Macomb, MI (US); Matthew S. Corbin, San Antonio, TX (US); Gregory G. Scott, Cincinnati, OH (US); Sajayesh Vijayachandran, Kannur (IN); Haribaskaran Nagarathinam, Aruppukottai (IN); Giri Prasannakumar Mathivanan, Mettur RS (IN)

(73) Assignee: Cilag GmbH International, Zug (CH)

( * ) Notice: Subject to any disclaimer, the term of this patent is extended or adjusted under 35 U.S.C. 154(b) by 120 days.

(21) Appl. No.: 18/077,331

(22) Filed: Dec. 8, 2022

(65) Prior Publication Data
US 2023/0225760 A1    Jul. 20, 2023

Related U.S. Application Data

(63) Continuation of application No. 17/213,302, filed on Mar. 26, 2021, now Pat. No. 11,633,211.

(30) Foreign Application Priority Data

May 1, 2020  (IN) .............................. 202011018670

(51) Int. Cl.
*A61B 17/34* (2006.01)

(52) U.S. Cl.
CPC ...... *A61B 17/3423* (2013.01); *A61B 17/3439* (2013.01); *A61B 2017/3429* (2013.01)

(58) Field of Classification Search
None
See application file for complete search history.

(56) References Cited

U.S. PATENT DOCUMENTS

3,817,251 A    6/1974  Hasson
4,699,616 A *  10/1987 Nowak ................. A61M 25/02
                                              128/DIG. 26

(Continued)

FOREIGN PATENT DOCUMENTS

AU    702882 B2    11/1993
CN    109069797 A  12/2018

(Continued)

OTHER PUBLICATIONS

U.S. Appl. No. 17/213,304.

(Continued)

*Primary Examiner* — Jan Christopher L Merene
(74) *Attorney, Agent, or Firm* — Frost Brown Todd LLC

(57) ABSTRACT

A depth limiter that is configured to couple with a cannula of a surgical access device. The depth limiter includes first and second user contact portions and first and second biasing features. The first biasing feature includes a first resilient portion and a first gripping surface. The second biasing feature includes a second resilient portion and a second gripping surface. The first and second resilient portions are configured to move the respective first and second gripping surfaces from a fixed configuration to a movable configuration when the respective first and second user contact portions are actuated. In the fixed configuration, the first and second gripping surfaces collectively restrict axial movement of the depth limiter by directly contacting the cannula. In the movable configuration, the first and second gripping (Continued)

surfaces extend parallel to a longitudinal axis and allow for axial movement of the depth limiter relative to the cannula.

20 Claims, 34 Drawing Sheets

(56) References Cited

U.S. PATENT DOCUMENTS

| | | |
|---|---|---|
| 5,002,557 A | 3/1991 | Hasson |
| 5,147,316 A | 9/1992 | Castillenti |
| 5,215,531 A | 6/1993 | Maxson et al. |
| D338,270 S | 8/1993 | Stephens et al. |
| 5,256,147 A | 10/1993 | Vidal et al. |
| 5,257,975 A | 11/1993 | Foshee |
| 5,263,939 A | 11/1993 | Wortrich |
| 5,267,970 A | 12/1993 | Chin et al. |
| 5,290,249 A | 3/1994 | Foster et al. |
| 5,364,372 A | 11/1994 | Danks et al. |
| D354,562 S | 1/1995 | Medema |
| 5,540,675 A | 7/1996 | Hasson |
| 5,697,913 A | 12/1997 | Sierocuk et al. |
| 5,792,135 A | 8/1998 | Madhani et al. |
| 5,800,451 A | 9/1998 | Buess et al. |
| 5,817,061 A | 10/1998 | Goodwin et al. |
| 5,833,666 A | 11/1998 | Davis et al. |
| 5,836,913 A | 11/1998 | Orth et al. |
| 5,855,566 A | 1/1999 | Dunlap et al. |
| 5,951,588 A | 9/1999 | Moenning |
| 5,957,888 A | 9/1999 | Hinchcliffe |
| 6,432,085 B1 | 8/2002 | Stellon et al. |
| 6,451,041 B1 | 9/2002 | Moenning et al. |
| 6,620,173 B2 | 9/2003 | Gerbi et al. |
| 6,632,197 B2 | 10/2003 | Lyon |
| 6,638,265 B1 | 10/2003 | Ternamian |
| 6,808,492 B2 | 10/2004 | Snyder |
| 7,235,064 B2 | 6/2007 | Hopper et al. |
| 7,473,220 B2 | 1/2009 | Francese et al. |
| 7,981,092 B2 | 7/2011 | Duke |
| 8,147,453 B2 | 4/2012 | Albrecht et al. |
| 8,226,553 B2 | 7/2012 | Shelton, IV et al. |
| 8,251,900 B2 | 8/2012 | Ortiz et al. |
| 8,287,503 B2 | 10/2012 | Albrecht et al. |
| 8,479,969 B2 | 7/2013 | Shelton, IV |
| 8,568,362 B2 | 10/2013 | Moreno, Jr. et al. |
| 8,573,465 B2 | 11/2013 | Shelton, IV |
| 8,579,807 B2 | 11/2013 | Moreno, Jr. et al. |
| 8,636,686 B2 | 1/2014 | Minnelli et al. |
| 8,690,831 B2 | 4/2014 | Duke |
| 8,783,541 B2 | 7/2014 | Shelton, IV et al. |
| 8,800,838 B2 | 8/2014 | Shelton, IV |
| 8,821,527 B2 | 9/2014 | Farnan et al. |
| 8,939,946 B2 | 1/2015 | Albrecht et al. |
| 9,259,238 B2 | 2/2016 | Albrecht et al. |
| 9,289,200 B2 | 3/2016 | Dang et al. |
| 9,522,265 B2 | 12/2016 | Pravong et al. |
| 9,675,379 B2 | 6/2017 | Kucklick |
| 10,327,805 B2 | 6/2019 | Hibner et al. |
| 10,327,809 B2 | 6/2019 | Buyda et al. |
| 10,792,069 B2 | 10/2020 | Hall et al. |
| 10,820,924 B2 | 11/2020 | Hall et al. |
| 11,633,211 B2 | 4/2023 | Muthuchidambaram et al. |
| 11,712,267 B2 | 8/2023 | Mclain |
| 2005/0113856 A1 | 5/2005 | Epstein |
| 2005/0165432 A1 | 7/2005 | Heinrich |
| 2007/0225643 A1 | 9/2007 | Hopper et al. |
| 2009/0182282 A1 | 7/2009 | Okihisa et al. |
| 2010/0010449 A1 | 1/2010 | Leibowitz et al. |
| 2010/0057010 A1 | 3/2010 | Göransson |
| 2012/0227221 A1 | 9/2012 | Whitaker et al. |
| 2013/0060084 A1 | 3/2013 | Fouts et al. |
| 2013/0204095 A1* | 8/2013 | Mark ............... A61B 17/0218 600/249 |
| 2014/0066953 A1* | 3/2014 | Keating ............. A61B 17/3439 606/130 |
| 2016/0015423 A1 | 1/2016 | Ravikumar et al. |
| 2017/0245888 A1* | 8/2017 | Buyda ............. A61B 17/3421 |
| 2017/0245889 A1 | 8/2017 | Herrell et al. |
| 2017/0311932 A1 | 11/2017 | Rebellino |
| 2018/0199959 A1 | 7/2018 | Lee |
| 2018/0206883 A1 | 7/2018 | McIntyre et al. |
| 2018/0214140 A1 | 8/2018 | Nock et al. |
| 2019/0000496 A1 | 1/2019 | Shelton, IV et al. |
| 2019/0083071 A1 | 3/2019 | Rebellino et al. |
| 2019/0150900 A1 | 5/2019 | Choung |
| 2019/0254703 A1 | 8/2019 | Ciampini et al. |
| 2019/0254704 A1 | 8/2019 | Buyda et al. |
| 2019/0282793 A1 | 9/2019 | Stafford |
| 2019/0380742 A1 | 12/2019 | Hall et al. |
| 2020/0080675 A1 | 3/2020 | White et al. |
| 2020/0205855 A1 | 7/2020 | Aravalli |
| 2021/0338269 A1 | 11/2021 | Scott et al. |
| 2021/0338272 A1 | 11/2021 | Muthuchidambaram et al. |
| 2021/0338274 A1 | 11/2021 | Scott et al. |
| 2021/0338275 A1 | 11/2021 | Vijayachandran |
| 2021/0338276 A1 | 11/2021 | Scott |
| 2021/0338278 A1 | 11/2021 | Scott et al. |
| 2021/0338281 A1 | 11/2021 | Mozloom, Jr. et al. |
| 2021/0338282 A1 | 11/2021 | Vijayachandran |
| 2021/0338283 A1 | 11/2021 | McLain |
| 2021/0338371 A1 | 11/2021 | Harris et al. |

FOREIGN PATENT DOCUMENTS

| | | |
|---|---|---|
| CN | 106344126 B | 2/2019 |
| DE | 202007001745 U1 | 4/2007 |
| EP | 2174602 A1 | 4/2010 |
| EP | 3210553 B1 | 10/2019 |
| WO | WO 1999/052457 A1 | 10/1999 |
| WO | WO 2004/032756 A2 | 4/2004 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

U.S. Appl. No. 17/213,401.
U.S. Appl. No. 17/213,409.
U.S. Appl. No. 17/213,415; and Muthuchidamaram et. al, Apr. 25, 2023.
U.S. Appl. No. 18/173,267, McLain, Aug. 1, 2023.
International Search Report and Written Opinion dated Jul. 22, 2021, for International Application No. PCT/EP2021/061421, 15 pages.
International Search Report and Written Opinion dated Aug. 3, 2021, for International Application No. PCT/EP2021/061428, 15 pages.
International Search Report and Written Opinion dated Jul. 16, 2021, for International Application No. PCT/EP2021/061442, 13 pages.
International Search Report and Written Opinion dated Jul. 8, 2021, for International Application No. PCT/EP2021/061447, 15 pages.
International Search Report and Written Opinion dated Jul. 27, 2021, for International Application No. PCT/EP2021/061456, 14 pages.
International Search Report and Written Opinion dated Jul. 13, 2021, for International Application No. PCT/EP2021/061459, 16 pages.
International Search Report and Written Opinion dated Jul. 20, 2021, for International Application No. PCT/EP2021/061466, 17 pages.
International Search Report and Written Opinion dated Jul. 15, 2021, for International Application No. PCT/EP2021/061468, 16 pages.
Chinese Office Action, The First Office Action and First Search, dated Mar. 21, 2025 for Application No. CN 202180032479.5, 15 pgs.

* cited by examiner

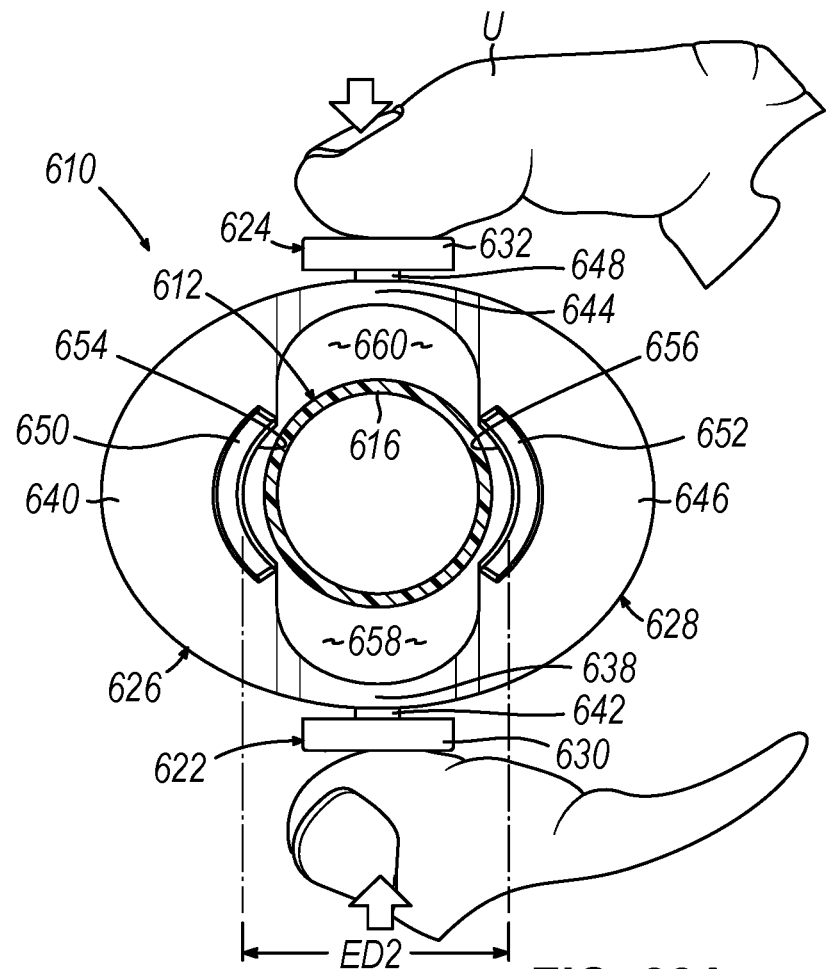
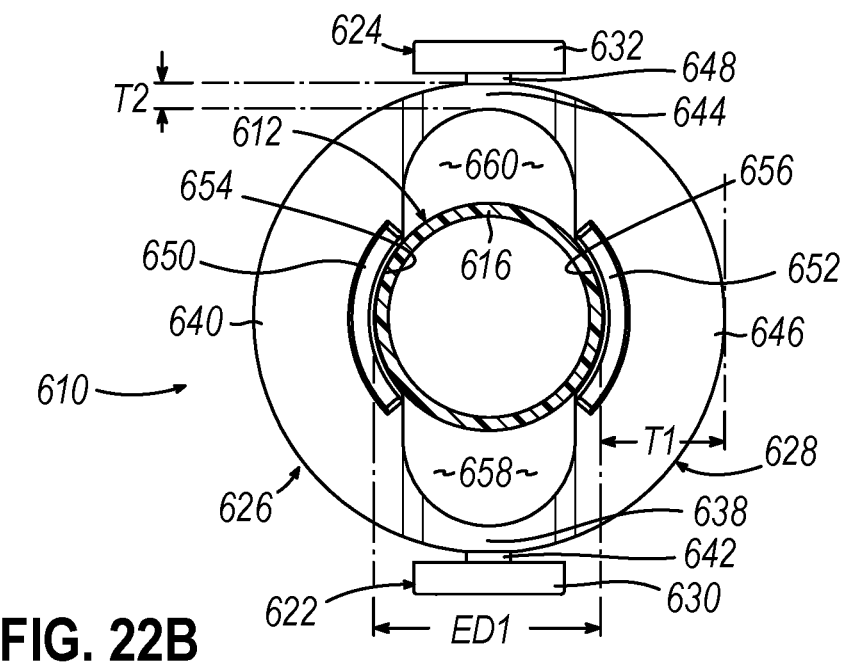
FIG. 22A
FIG. 22B

PINCH-TO-RELEASE CANNULA DEPTH LIMITER

PRIORITY

This application is a continuation of U.S. patent application Ser. No. 17/213,302 filed Mar. 26, 2021 and issued as U.S. Pat. No. 11,633,211 on Apr. 25, 2023, which claims priority to Indian Provisional Pat. App. No. 20/201,1018670, entitled "Pinch-to-Release Cannula Depth Limiter," filed on May 1, 2020.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Pre-defined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019, issued as U.S. Pat. No. 11,389,192 on Jul. 19, 2022. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 22A depicts a top plan view of the depth limiter and the cannula tube of FIG. 20 with the cannula tube being shown in cross-section, where the depth limiter is in a movable configuration that allows for axial movement of the depth limiter relative to the cannula tube when actuated by a user;

FIG. 22B depicts a top plan view of the depth limiter and cannula tube of FIG. 22A, but with the depth limiter in a fixed configuration of FIG. 19;

Figure 1:
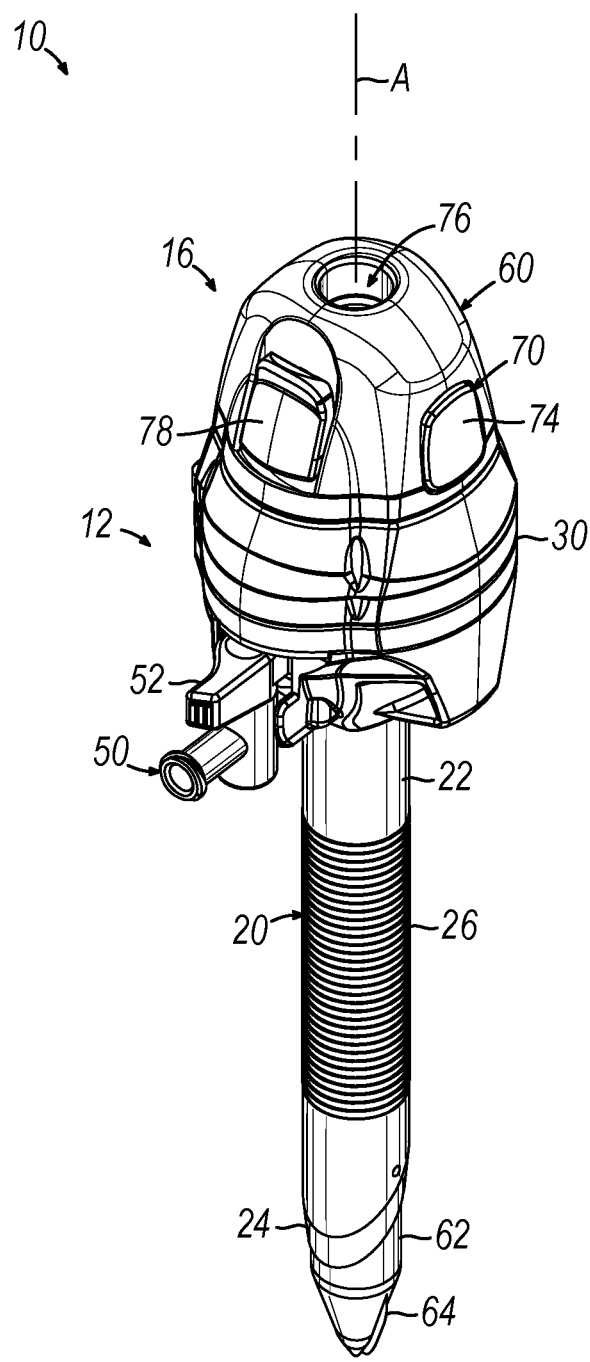
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
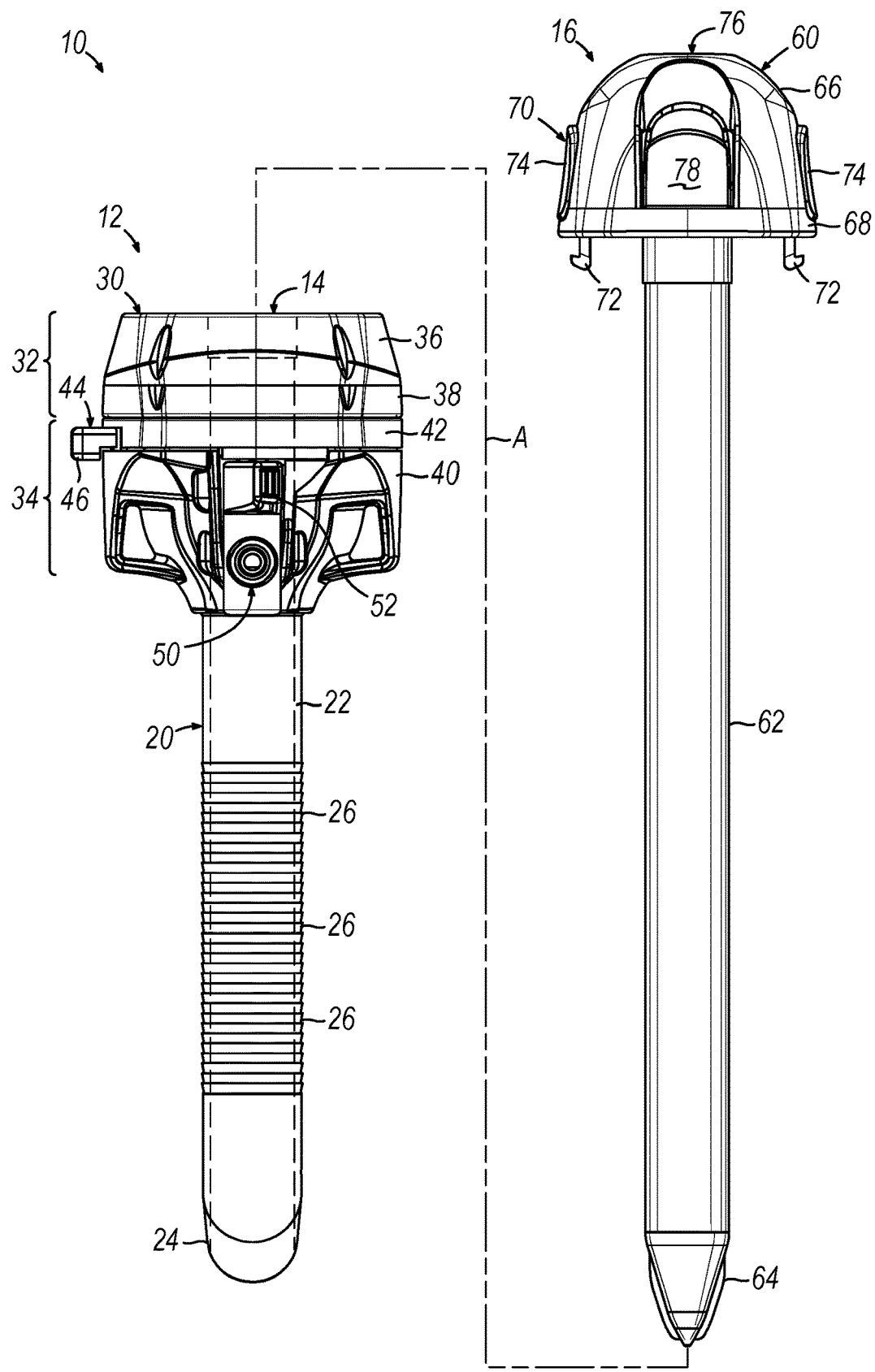
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
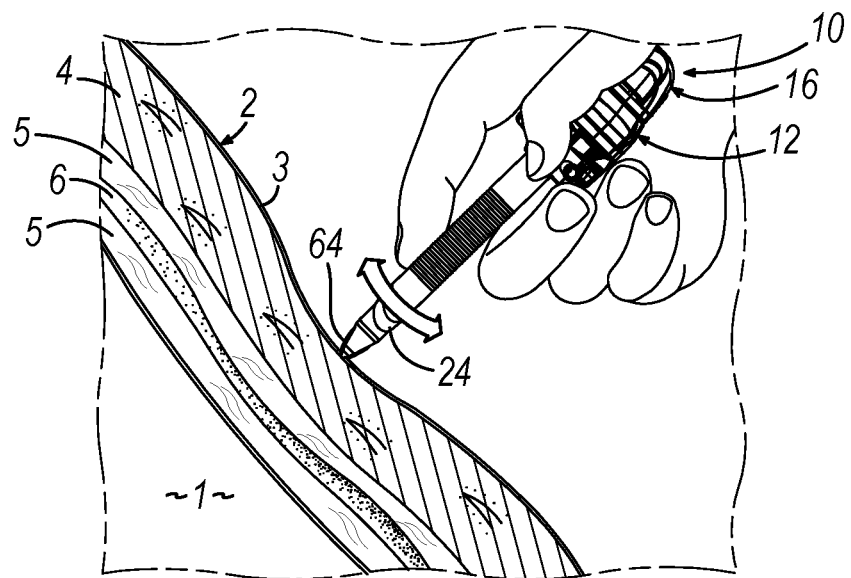
FIG. 3A depicts a side sectional view of the trocar of FIG. 1 being manipulated by a clinician through tissue layers of an abdominal wall.
Figure 3B:
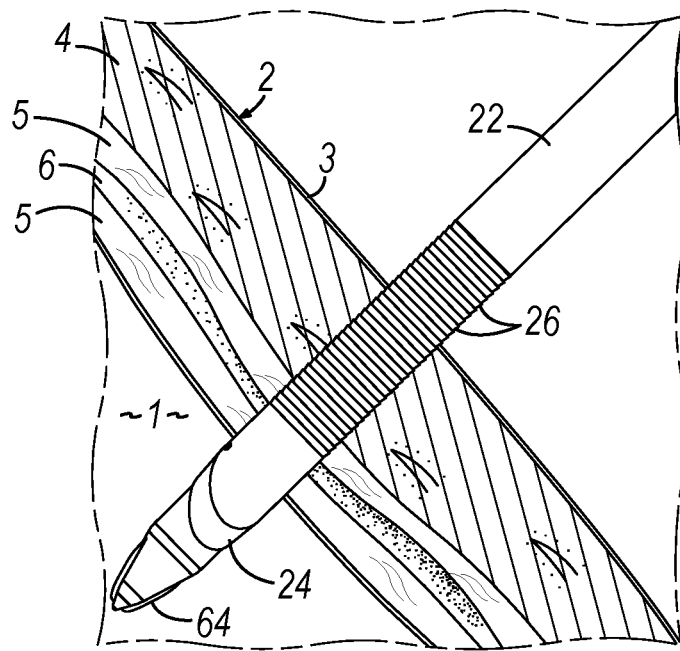
FIG. 3B depicts an enlarged side sectional view of the trocar of FIG. 1, showing a distal end of the trocar received within the abdominal cavity of FIG. 3A.
Figure 3C:
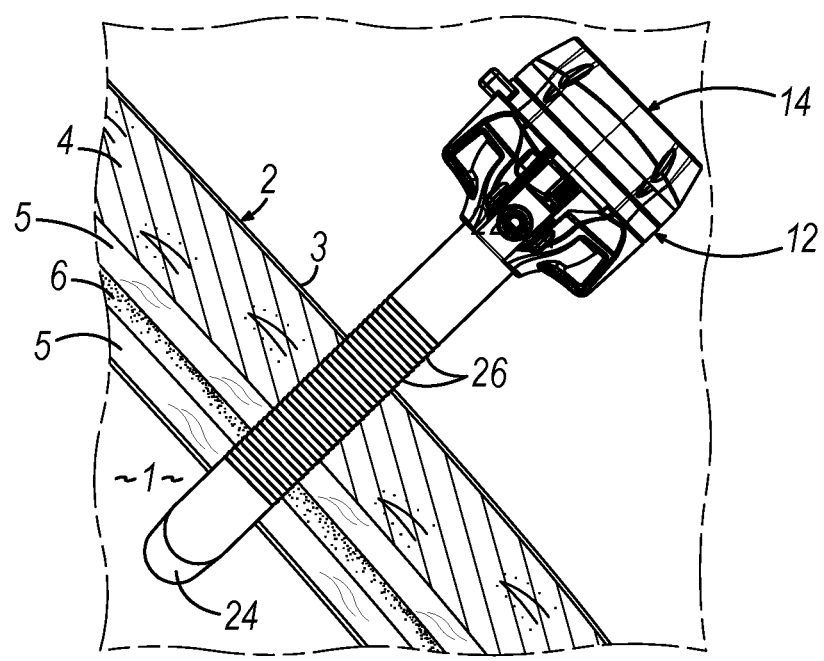
FIG. 3C depicts a side sectional view of the cannula assembly of FIG. 1, showing the cannula assembly remaining positioned within the abdominal wall of FIG. 3A following detachment and removal of the obturator.
Figure 3D:
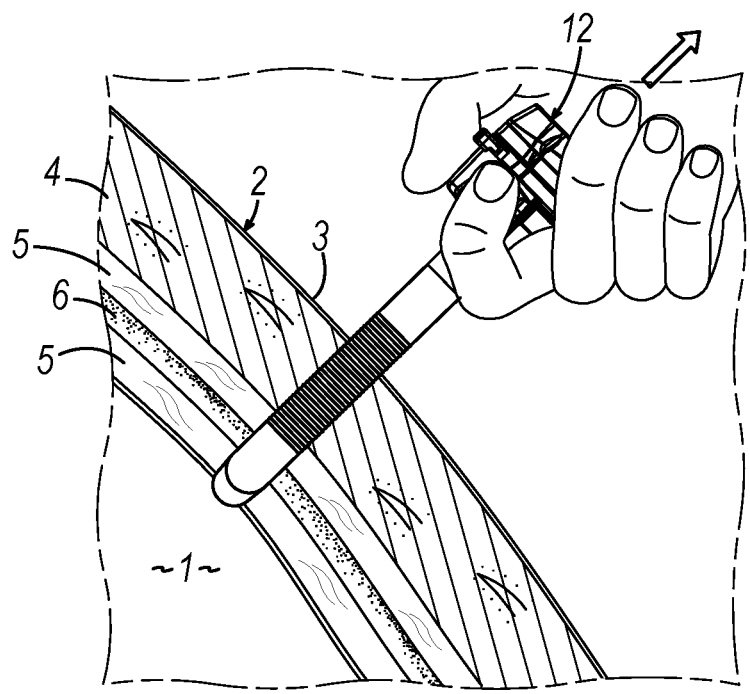
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
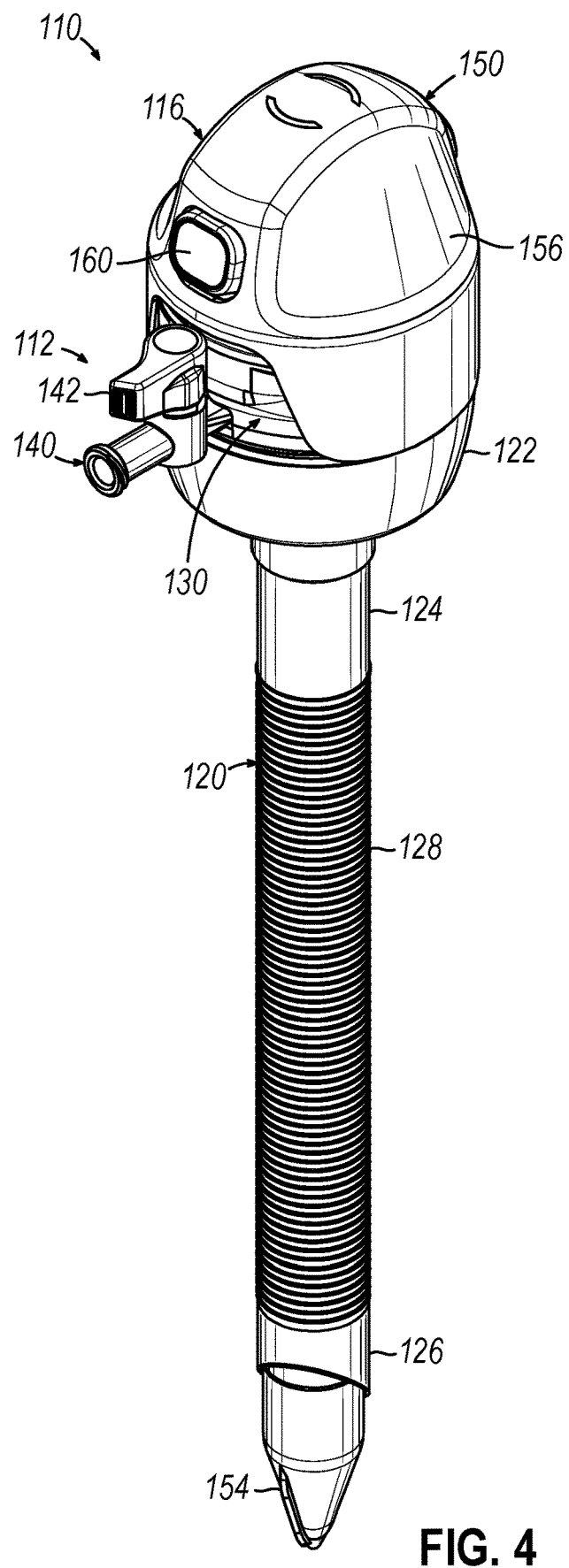
FIG. 4 depicts a perspective view of another exemplary trocar having a cannula assembly and an obturator shown in an assembled state, where the cannula assembly includes a cannula tube.
Figure 5:
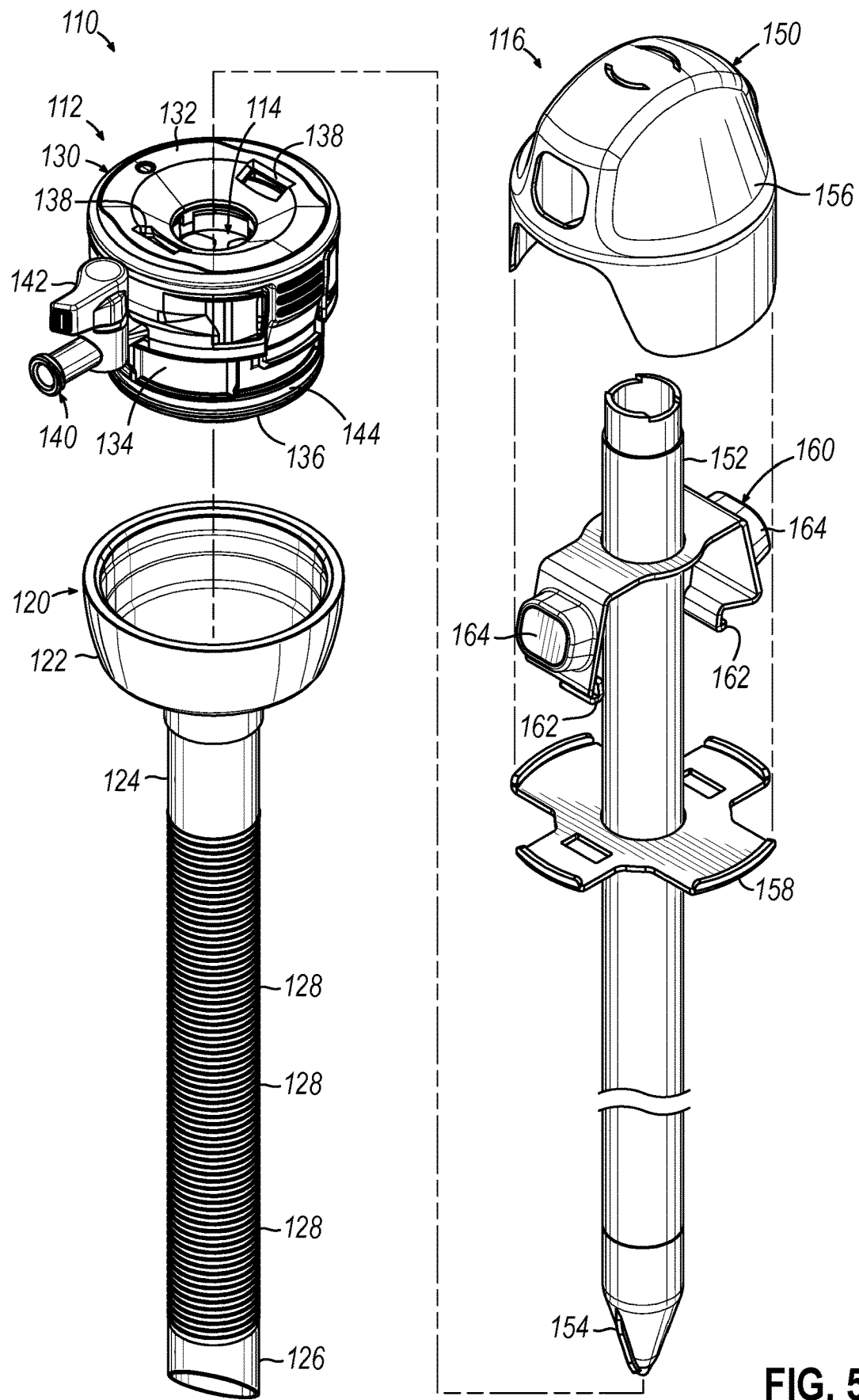
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, issued as U.S. Pat. No. 10,792,069 on Oct. 6, 2020, the disclosure of which is incorporated by reference herein; and/or U.S. Pat. Pub. No. 2019/0380742, entitled "Asymmetric Shaft Seal," published Dec. 19, 2019, issued as U.S. Pat. No. 10,820,924 on Nov. 3, 2020, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Depth Limiters and Associated Method

In some instances, a clinician may desire to limit the depth to which a single-use or reusable trocar (10, 110) may travel into abdominal wall (2) (e.g., after insertion of trocar (10, 110) to a desired position). Limiting the depth to which trocar (10, 110) may travel into abdominal wall (2) may assist in preventing distal tip (64, 154) of obturator (16, 116) and/or cannula tip (24, 126) of cannula assembly (12, 112) from inadvertently entering deeper than desired into abdominal cavity (1). Preventing over insertion of trocar (10, 110) may reduce undesirable contact of distal tip (64, 154) and/or cannula tip (24, 126) with anatomical structures contained within abdominal cavity (1).

Alternatively or in addition to limiting the depth to which single-use or reusable trocar (10, 110) may travel into abdominal wall (2), the clinician may desire to stabilize trocar (10, 110) relative to abdominal wall (2) (e.g., after insertion of trocar (10, 110) to a desired position in abdominal cavity (1)). The clinician may stabilize trocar (10, 110) relative to abdominal wall (2) by avoiding under insertion of trocar (10, 110). Stabilizing trocar (10, 110) relative to abdominal wall (2) after insertion into abdominal wall (2) may assist in preventing trocar (10, 110) from inadvertently pivoting about the insertion point in abdominal wall (2) after the clinician releases trocar (10, 110). Stabilizing trocar (10, 110) maintains cannula tip (24, 126), and thus, the entry point of surgical instruments into abdominal cavity (1)) in a desired position and/or orientation relative to abdominal cavity (1).

As described above with reference to FIGS. 1-5, obturators (16, 116) may be configured to be removably coupled with cannulas (20, 120) along a central axis (shown as trocar central axis (A) in FIGS. 1-2) to facilitate insertion of the surgical access device through a body cavity wall (shown as abdominal wall (2)) of the patient. Cannulas (20, 120) include working channels (14, 114) and tissue gripping features (shown as ribs 26, 128). Working channels (14, 114) are configured to guide a surgical instrument (not shown) along a central axis of cannulas (20, 120). Tissue gripping features are intended to include non-helical features (e.g., such as ridges and annular scallops) as well as helical threads (e.g., overlapping or non-overlapping threads). The tissue gripping features may extend along only a portion of the length of cannula tube (124). As previously described, ribs (26, 128) may be formed as annular scallops. Ribs (26, 128) may disposed along an outer surface of cannula (20, 120). As shown in FIGS. 3A-3D, ribs (26, 128) may be configured to stabilize cannula (20, 120) relative to abdominal wall (2) of the patient when cannula (20, 120) is inserted distally through abdominal wall (2).

To reduce over insertion and/or under insertion or trocar (10, 110), exemplary depth limiters (210, 310, 410, 510, 610, 710, 810, 910, 1010, 1110, 1210, 1310, 1410) may be selectively coupled with cannula tube (22, 124, 416, 914) of cannula (20, 120, 412, 912). Depth limiters (210, 310, 410, 510, 610, 710, 810, 910, 1010, 1110, 1210, 1310, 1410) are described in detail below with reference to FIGS. 6-39, and may be use alone or in combination with another depth limiter (210, 310, 410, 510, 610, 710, 810, 910, 1010, 1110, 1210, 1310, 1410) if desired. Depth limiters (210, 310, 410, 510, 610, 710, 810, 1010, 1110, 1210, 1310, 1410) may be scaled to fit a variety of different sized cannula tubes, including but not limited to those cannulas having a 5 mm diameter, a 8 mm diameter, a 10 mm diameter, and a 15 mm diameter.

Depth limiters (210, 310, 510, 610, 710, 810, 910, 1310, 1410) are shown with relation to trocar (110) of FIGS. 4-5. Similarly, depth limiter (410) is shown with relation to cannula (412) and cannula tube (416) of FIG. 14, and depth limiter (610) is shown with relation to cannula (612) of and cannula tube (616) FIG. 19. Additionally, depth limiters (1010, 1110, 1210) are shown with relation to trocar (10), cannula (20), and cannula tube (22) of FIGS. 1-3. However, it is envisioned that depth limiters (210, 310, 410, 510, 610, 710, 810, 910, 1010, 1110, 1210, 1310, 1410) may be used with a variety of other suitable trocars, cannula assemblies, and obturator, including trocars (10, 110) cannula tubes (22, 124, 416, 914) of cannulas (20, 120, 412, 912).

A. First Exemplary Depth Limiter

Figure 6:
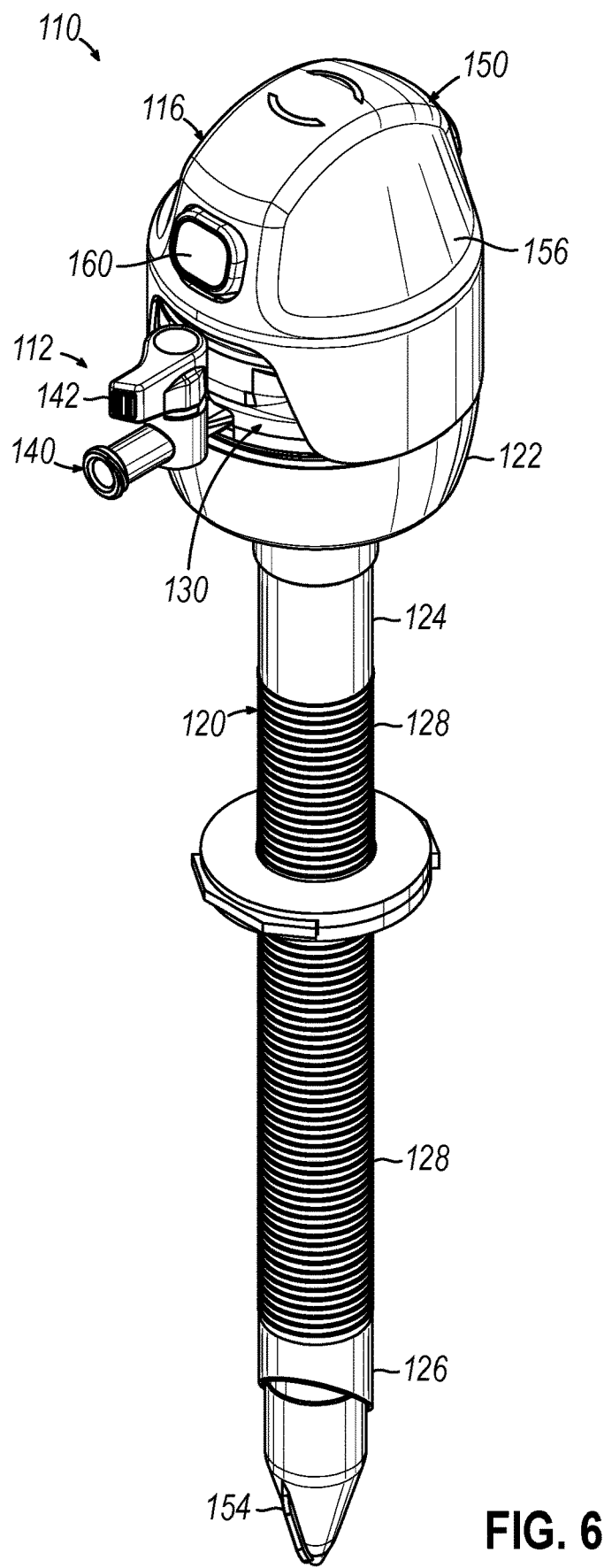
FIG. 6 depicts a perspective view of the trocar of FIG. 4 and a first exemplary depth limiter, where the depth limiter is in a fixed configuration that restricts axial movement of the depth limiter relative to the cannula tube of the cannula assembly of the trocar.
Figure 7:
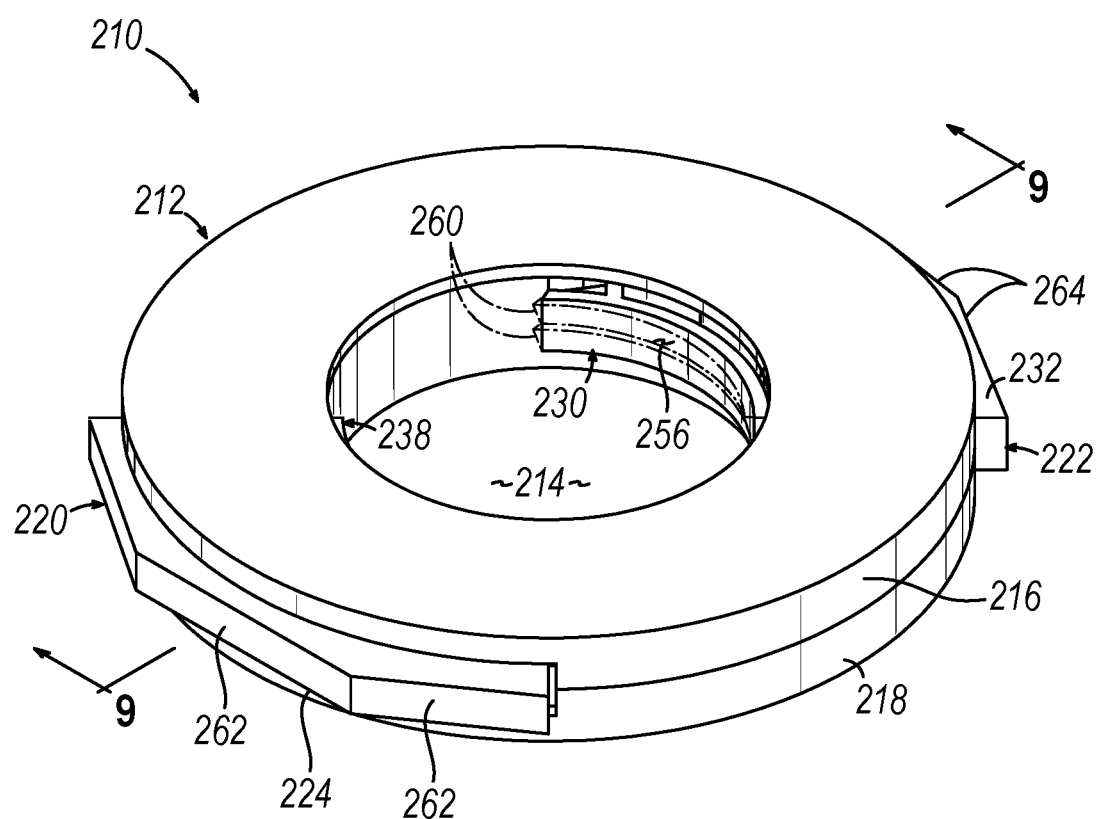
FIG. 7 depicts a perspective view of the depth limiter of FIG. 6, with engagement features shown in phantom.

FIGS. 6-10 show a first exemplary depth limiter (210) with relation to a surgical access device (shown as trocar (110)), which includes cannula assembly (112) and obturator (116) as described above. Particularly, FIG. 6 shows a perspective view of trocar (110) of FIG. 4, where depth limiter (210) is in a fixed configuration that restricts axial movement (along a longitudinal axis (A1)) of depth limiter (210) relative to cannula tube (124) of cannula assembly (112). FIG. 7 shows a perspective view of depth limiter (210) as including a housing (212) that may create central cavity (214). Housing (212) includes upper and lower housing portions (216, 218) that may be identical or different. Depth limiter (210) includes a first biasing feature (shown a ring member (220)) and a second biasing feature (shown as a ring member (222)). For example, ring members (220, 222) may be diametrically opposed spring members that may be compressed toward one another to release from cannula tube (124) as described below with reference to FIGS. 8A-8B.

Figure 8A:
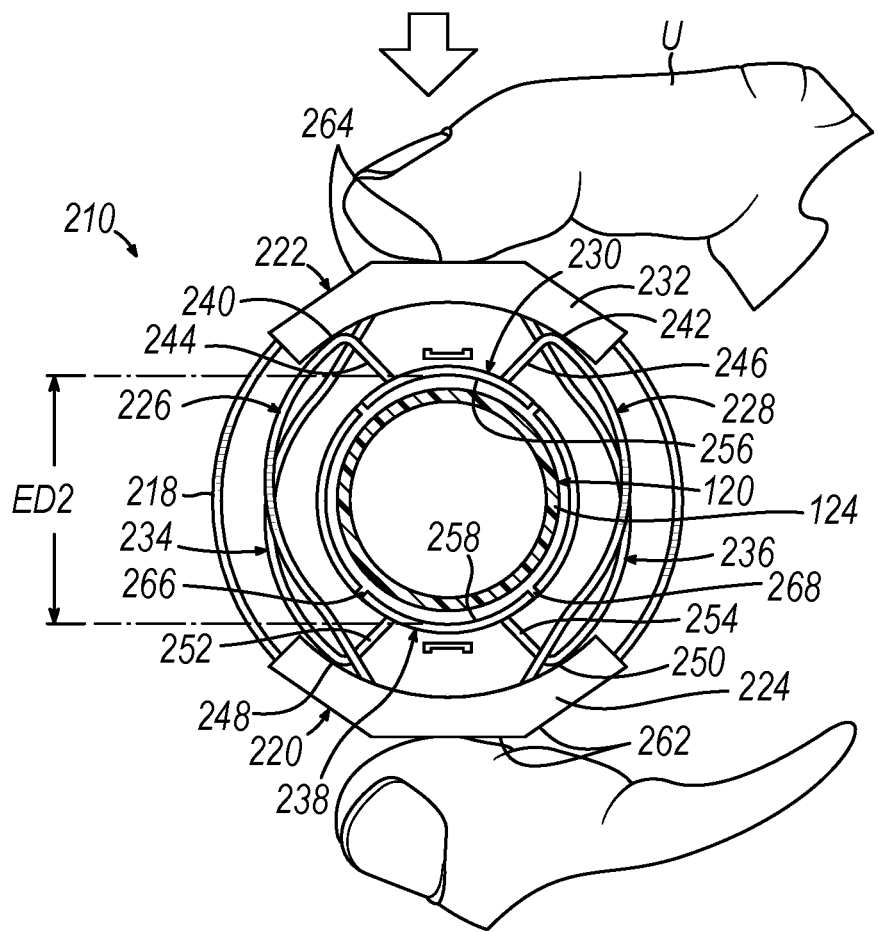
FIG. 8A depicts a top plan view of the depth limiter of FIG. 7 and the cannula tube of FIG. 6 shown in cross-section, where an upper housing portion of the depth limiter is removed to show the depth limiter in a movable configuration allowing for axial movement of the depth limiter relative to the cannula tube when actuated by a user.
Figure 8B:
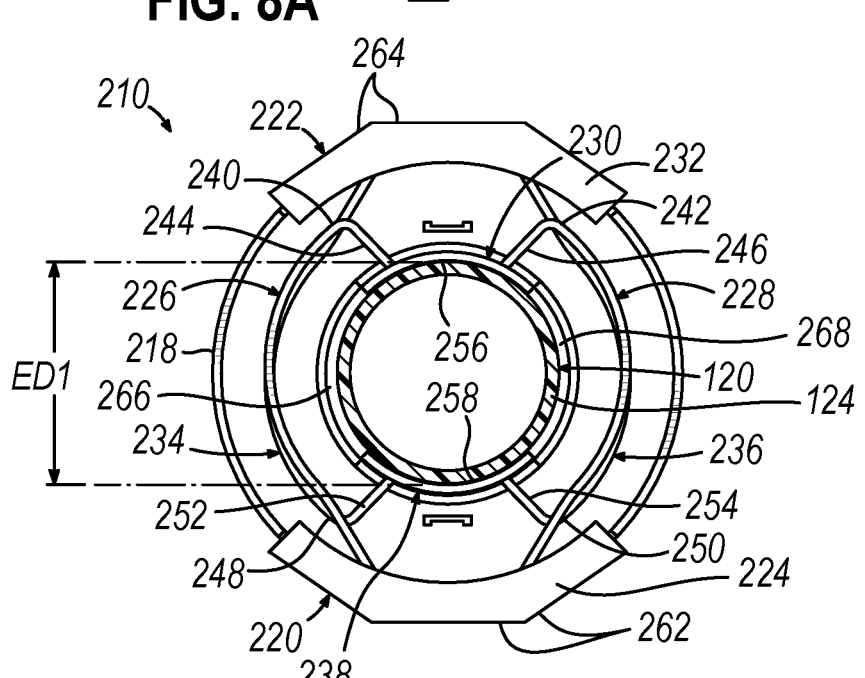
FIG. 8B depicts a top plan view of the depth limiter and the cannula tube of FIG. 8A, but with the depth limiter in the fixed configuration of FIG. 6.
Figure 9:
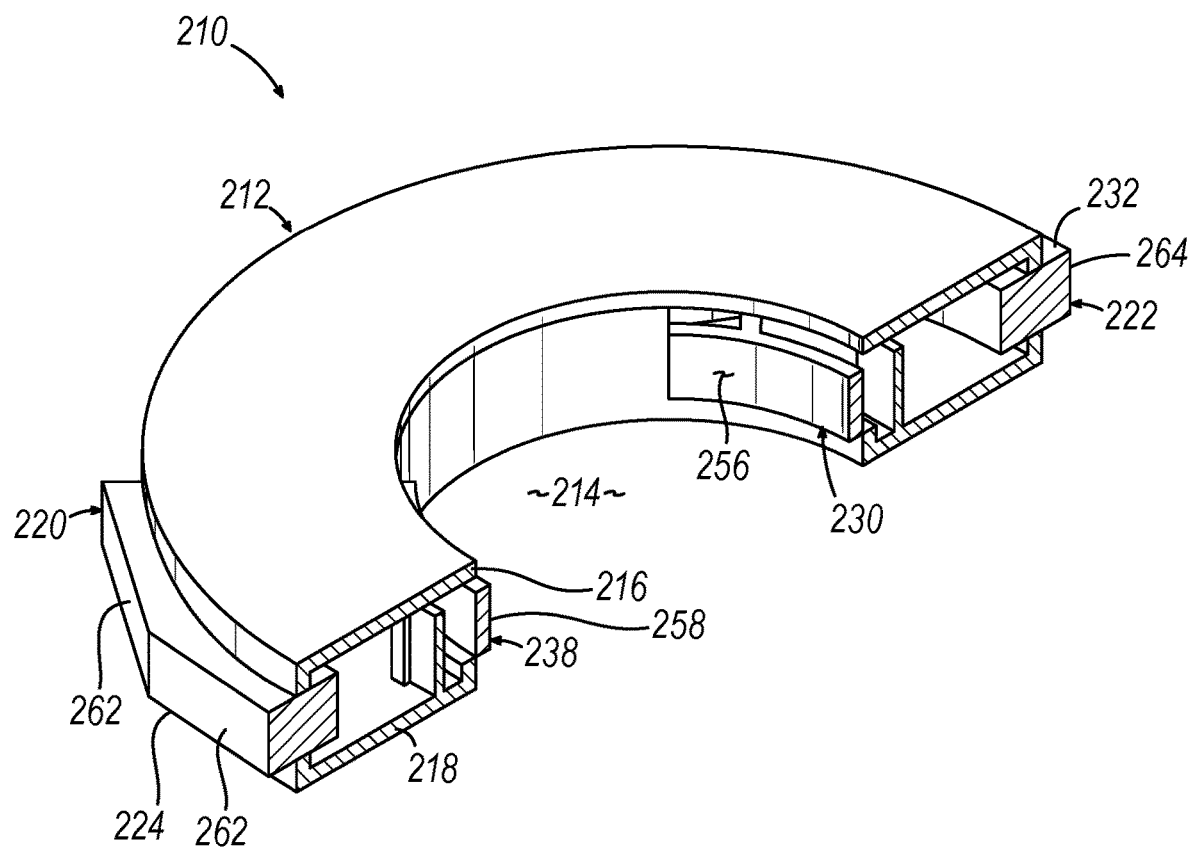
FIG. 9 depicts a cross-sectional view of the depth limiter of FIG. 7 taken along line 9-9 of FIG. 7.
Figure 10:
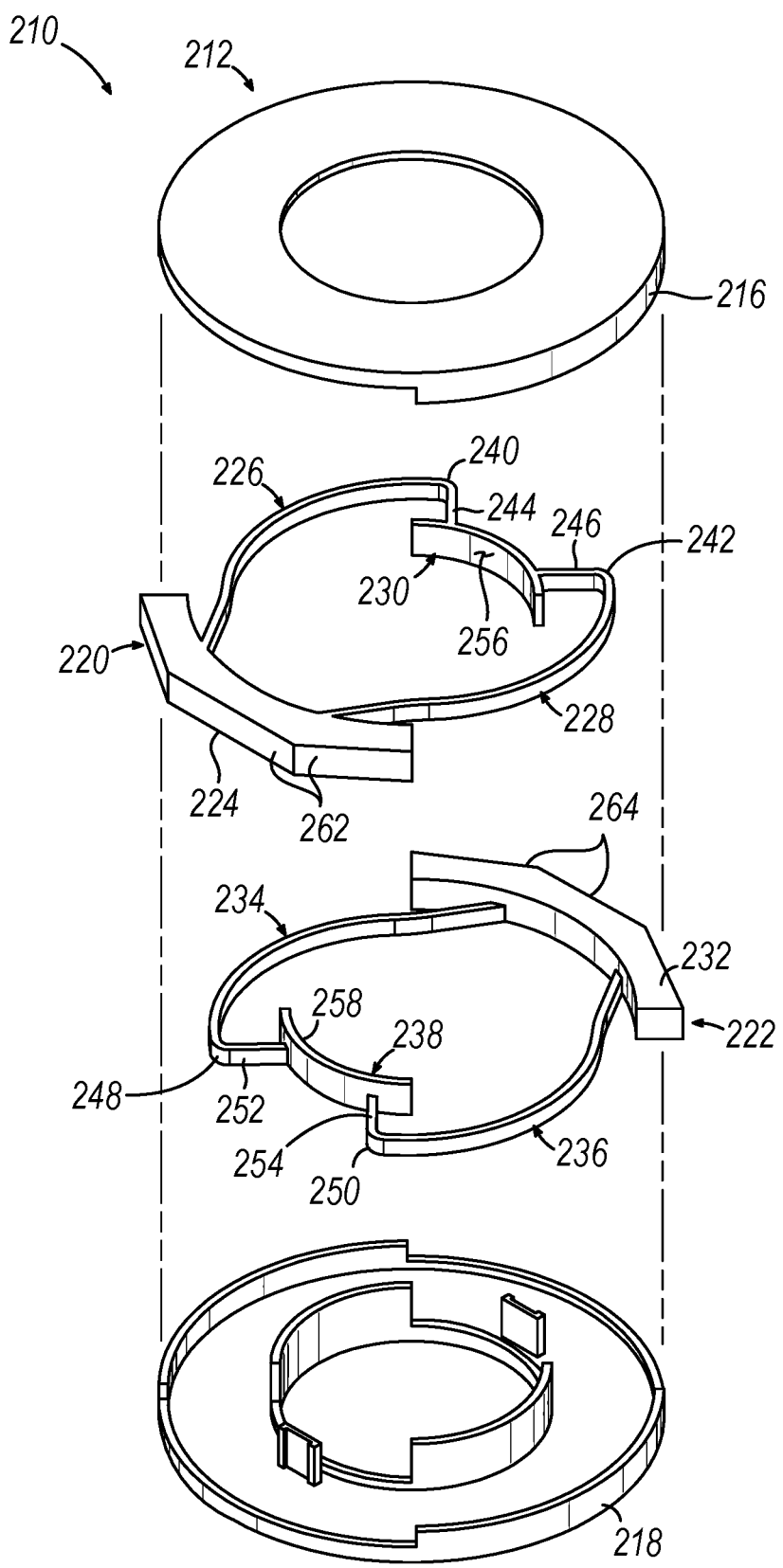
FIG. 10 depicts an exploded view of the depth limiter of FIG. 7.

As shown in FIGS. 7-10, ring member (220) includes a user contact portion (224), opposing biasing arms (226, 228), and a gripping member (230). Similarly, ring member (222) may include a user contact portion (232), opposing biasing arms (234, 236), and a gripping member (238). Biasing arms (226, 228) of ring member (220) may form a first resilient portion of ring member (220). Biasing arms (234, 236) of ring member (222) may form a second resilient portion of ring member (222). While FIGS. 8A-8B and 10 show ring members (220, 222) as being identical; ring members (220, 222) may be different if desired. Biasing arms (226, 228) of ring member (220) include apexes (240, 242) and bent back portions (244, 246) that are coupled with gripping member (230). Similarly, biasing arms (234, 236) of ring member (222) include apexes (248, 250) and bent back portions (252, 254) that are coupled with gripping member (238). Ring members (220, 222) may act as leaf springs. As shown in FIGS. 8A-9, ring members (220, 222) may be nested together.

FIG. 9 shows a cross-sectional view of depth limiter (210) of FIG. 7 taken along line 9-9 of FIG. 7, and FIG. 10 shows an exploded view of depth limiter (210) of FIG. 7. As shown, gripping member (230) of ring member (220) includes a gripping surface (256). Similarly, gripping member (238) of ring member (222) includes a gripping surface (258). As shown, gripping surfaces (256, 258) extend parallel to longitudinal axis (A1). Gripping surfaces (256, 258) may be smooth or non-smooth. For example, a non-smooth surface may include one or more features to lockingly engage cannula tube (124). As shown in FIGS. 8A-10, gripping surfaces (256, 258) may be smooth to frictionally engage ribs (128) of cannula (120) in the fixed configuration and not frictionally engage ribs (128) of cannula (120) in the movable configuration. Alternatively, at least one of gripping surfaces (256, 258) may include at least one tooth configured to lockingly engage with at least one of rib (128) of cannula (120) in the fixed configuration and not lockingly engage with rib (128) of cannula (120) in the movable configuration. Particularly, FIG. 7 shows gripping surface (258) including a plurality of engagement features (260) in phantom which are optional. Engagement features (260) may be configured to lockingly engage with ribs (128) disposed on an outer surface of cannula tube (124) of cannula (120) in the fixed configuration and not lockingly engage with ribs (128) disposed on the outer surface of cannula tube (124) in the movable configuration.

As shown in FIGS. 7-10, upper and lower housing portions (216, 218) may surround biasing arms (226, 228) of ring member (220, 222) and biasing arms (234, 236) of ring member (222). Upper and lower housing portions (216, 218) may expose user contact portions (224, 232) and gripping members (230, 238). As such, upper and lower housing portions (216, 218) may reduce or prevent the likelihood of depth limiter (210) inadvertently pinching the glove of a user (e.g., a surgeon or another medical professional) and/or reduce or prevent depth limiter (210) from pinching tissue of the patient. As shown, user contact portions (224, 232) are disposed circumferentially opposite one another (i.e., diametrically opposed); however, other arrangements of user contact portions (224, 232) are also envisioned.

Depth limiter (210) is movable by user (U) between a movable configuration shown in FIG. 8A and a fixed configuration shown in FIG. 8B. In other words, depth limiter (210) may be selectively actuated from the fixed configuration having a first effective diameter (ED1) to the movable configuration having a second effective diameter (ED2) to couple depth limiter (210) with cannula tube (124). Additionally, depth limiter (210) may be selectively actuated again from the fixed configuration to the movable configuration to decouple depth limiter (210) from cannula tube (124). As shown, first effective diameter (ED1) is smaller than second effective diameter (ED2). FIG. 8A shows a top plan view of depth limiter (210) of FIG. 7 with cannula tube (124) of FIG. 6 being shown in cross-section. Upper housing portion (216) of depth limiter (210) is removed in FIGS. 8A-8B to reveal depth limiter (210) in the movable configuration allowing for axial movement of depth limiter (210) relative to cannula tube (124) when actuated by the user.

Particularly, gripping surface (256) is movably coupled with biasing arms (226, 228) and gripping surface (258) is movably coupled with biasing arms (234, 236) from the fixed configuration to the movable configuration when respective user contact portions (224, 232) are actuated by user. For example, in the movable configuration of FIG. 8A, gripping surfaces (256, 258) collectively form the second effective diameter (ED2) that allows for axial movement of depth limiter (210) relative to an outer diameter of cannula tube (124) of cannula (120). In other words, actuation of user contact portions (224, 232) is configured to respectively cause biasing arms (226, 228) of ring member (220) and biasing arms (234, 236) of ring member (222) to move gripping surfaces (256, 258) radially outward to selectively engage and disengage cannula tube (124) of cannula (120) while in the movable configuration.

For example, the user (U) may pinch two points (user contact portions (224, 232)) to increase the effective diameter between opposing gripping surface (256, 258) of depth limiter (210), and then release user contact portions (224, 232) to decrease the effective diameter between opposing gripping surface (256, 258) of depth limiter (210) in the fixed configuration to fix or clamp depth limiter (210) axially relative to cannula tube (124). As shown, user contact portions (224, 232) are configured to be actuated by the user (U) using thumb and index fingers. However, the user (U) may depress user contact portions (224, 232) in other ways (e.g., using one or more fingers and the palm). By pinching outer surfaces (262, 264) of user contact portions (224, 232), ring members (220, 222) slide and open up opposing gripping surface (256, 258) for disengagement. In the movable configuration, the virtual diameter defined by opposing gripping surface (256, 258) is larger than that of cannula tube (124), allowing for free movement of depth limiter (210) to any user-specified depth along cannula tube (124). As shown, gripping surface (256) is radially offset from the user contact portion (224) by approximately 180 degrees, and gripping surface (258) is radially offset from the user contact portion (232) by approximately 180 degrees.

FIG. 8B shows a top plan view of depth limiter (210) and cannula tube (124) of cannula (120) of FIG. 8A, but with depth limiter (210) in the fixed configuration of FIG. 6. The user (U) may release gripping surfaces (256, 258) from FIG. 8A from the outer surface of cannula tube (124), so that ring members (220, 222) return to the fixed configuration. Gripping surfaces (256, 258) may be disposed circumferentially opposite one another and may be configured to directly contact circumferentially opposite sides of cannula (120) in the fixed configuration. In the fixed configuration, gripping surfaces (256, 258) collectively form a first effective diameter (ED1) that restricts axial movement of depth limiter (210) relative to cannula (120) by directly contacting cannula (120). As shown, the first effective diameter (ED1) defined by gripping surfaces (256, 258) is smaller than the outer diameter cannula tube (124) when ring members (220, 222) are in the fixed configuration. The fixed configuration may also be considered the resting configuration. As shown, gripping surfaces (256, 258) do not completely (or entirely) surround cannula tube (124) of cannula (120) in either the fixed configuration or the movable configuration. Instead, gripping surfaces (256, 258) are spaced apart from one another in both of the fixed and movable configurations and separated by gaps (266, 268). In the fixed configuration of FIG. 8B, gripping surfaces (256, 258) are shown to grip less than half of the circumference of cannula tube (124) at discrete regions; however, this may vary.

As shown in FIGS. 7-10, user contact portion (224) is disposed between and fixably coupled to biasing arms (226, 228). In some versions, user contact portion (224) may be integrally formed together as a unitary piece together with biasing arms (226, 228). In some versions, gripping member (230) may be integrally formed together as a unitary piece together with biasing arms (226, 228). Similarly, user contact portion (232) is disposed between and fixably coupled to biasing arms (234, 236). In some versions, user contact portion (232) may be integrally formed together as a unitary piece together with biasing arms (234, 236). In some versions, gripping member (238) may be integrally formed together as a unitary piece together with biasing arms (234, 236).

Depth limiter (210) is shown to have a low-profile form. Depth limiter (210) may nest onto proximal end of cannula tube (124) for transport and/or storage. Depth limiter (210) may include simple to operate pinch-to release controls. Depth limiter (210) may be reusable or disposable. For example, depth limiter (210) may be injection molded for a disposable model. Alternatively, depth limiter (210) may be and stamped, machined, and/or metal-injection molded for a re-usable model. In some versions, depth limiter (210) may be completely formed of metal. Depth limiter (210) may fit robotic and laparoscopic instruments, which may provide less medical waste for medical facilities (e.g., hospitals).

B. Second Exemplary Depth Limiter

Figure 11:
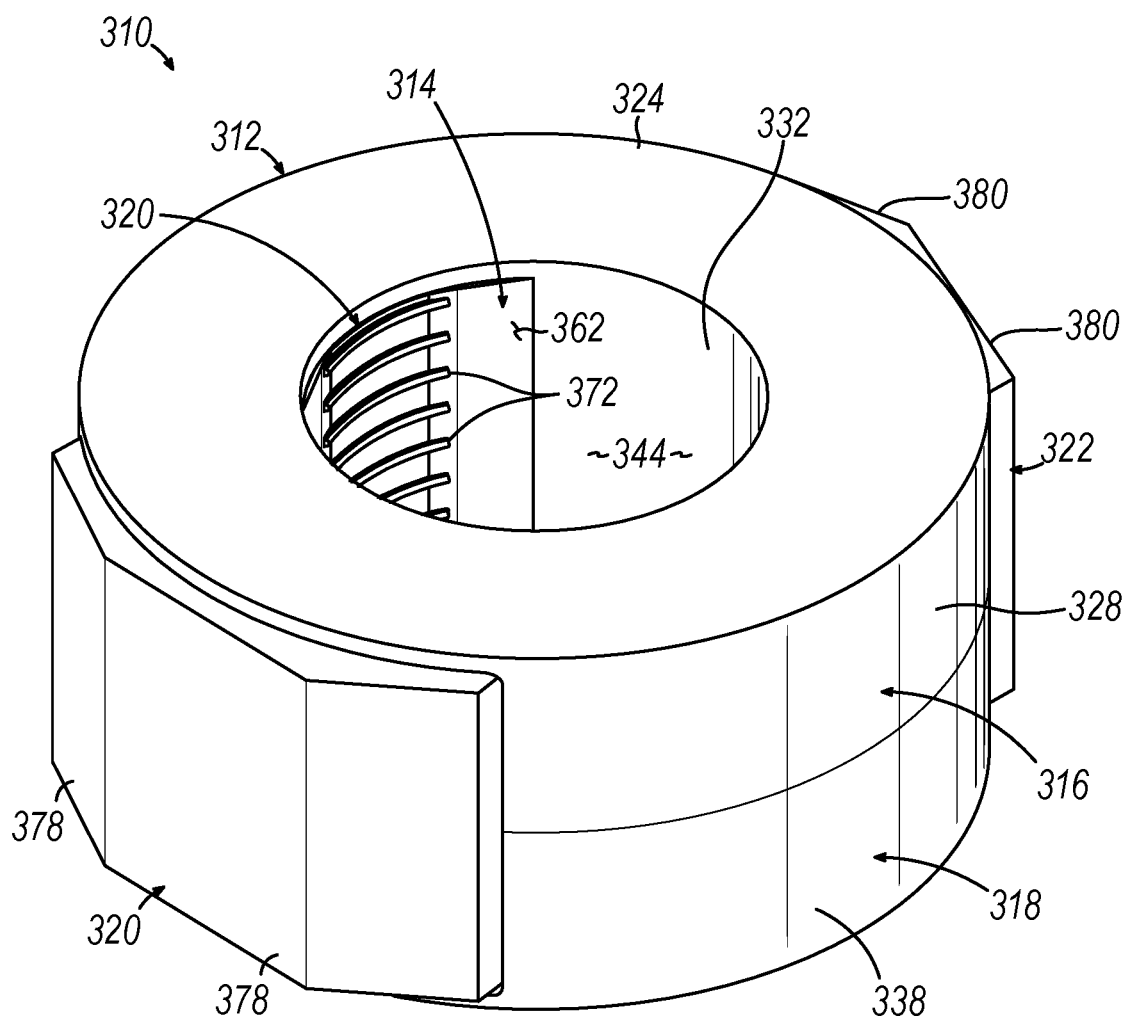
FIG. 11 depicts a perspective view of a second exemplary depth limiter.
Figure 12A:
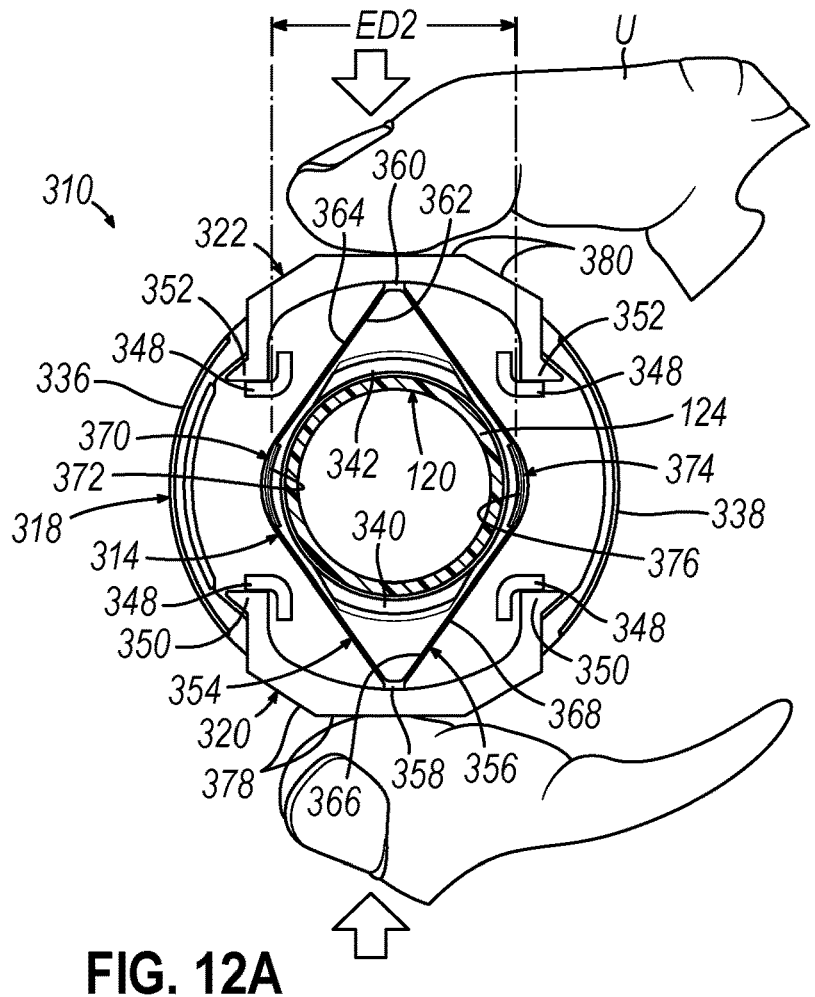
FIG. 12A depicts a top plan view of the depth limiter of FIG. 11 coupled with the cannula tube of FIG. 5 which is shown in cross-section, where an upper housing portion of the depth limiter is removed to show the depth limiter in a movable configuration allowing for axial movement of the depth limiter relative to the cannula tube when actuated by a user.
Figure 12B:
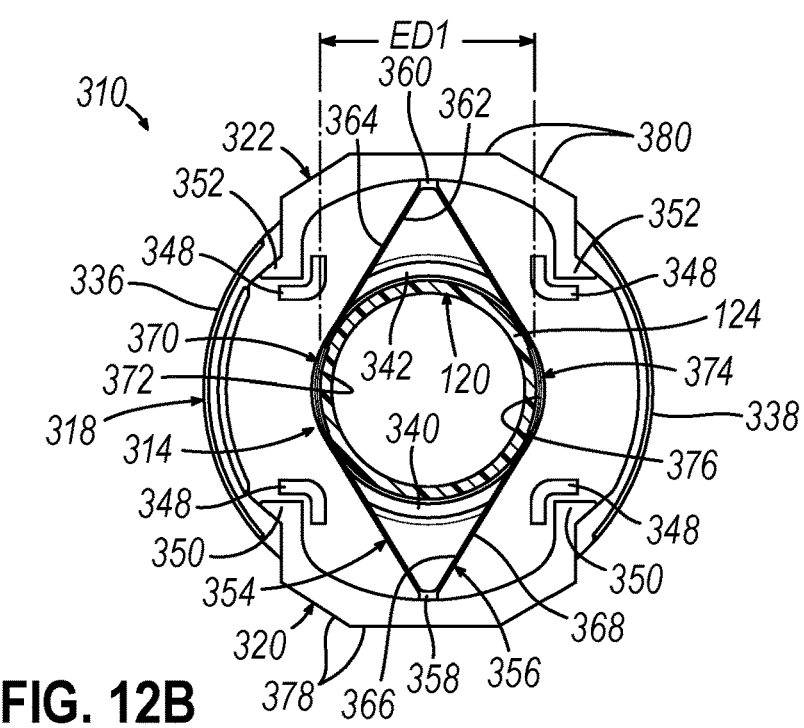
FIG. 12B depicts a top plan view of the depth limiter and cannula tube of FIG. 12A, but with the depth limiter in a fixed configuration that restricts axial movement of the depth limiter relative to the cannula tube.
Figure 13:
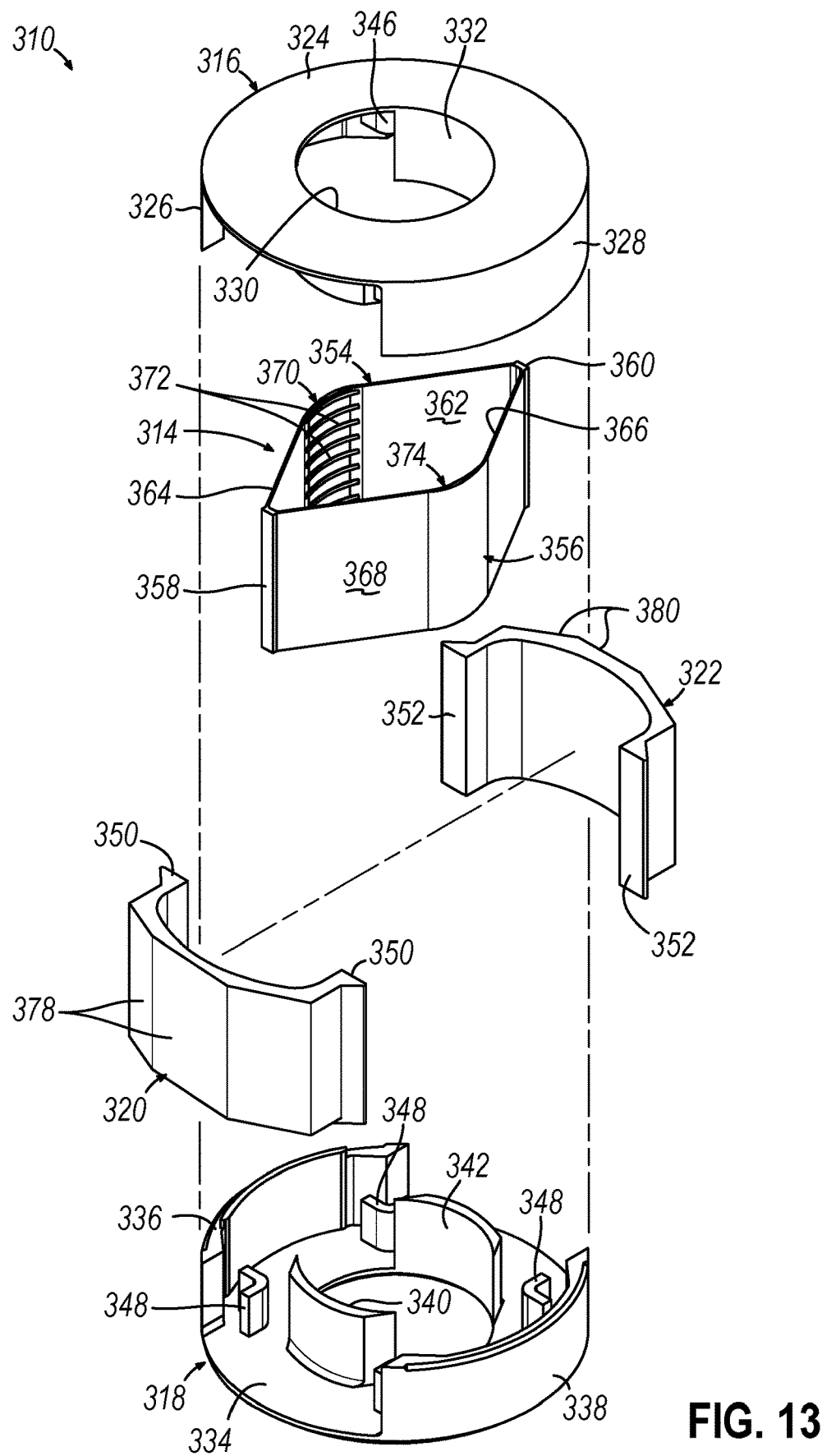
FIG. 13 depicts an exploded view of the depth limiter of FIG. 11.

FIGS. 11-13 show a second exemplary depth limiter (310) which is configured to be used with trocar (10, 110) shown and described with reference to FIGS. 1-5. Particularly, FIG. 11 shows a perspective view of depth limiter (310), and FIG. 13 shows an exploded view of depth limiter (310) of FIG. 11. As shown, depth limiter (310) includes a housing (312) and a biasing feature (314). Housing (312) includes upper and lower housing portions (316, 318) and user contact portions (320, 322). As such, upper and lower housing portions (316, 318) may be welded at the seam and may reduce or prevent depth limiter (310) from pinching the glove of the user (U) and/or reduce or prevent depth limiter (310) from pinching tissue of the patient. Upper and lower housing portions (316, 318) are shown as being identical. However, upper and lower housing portions (316, 318) may be different if desired. Upper housing portion (316) may include a top wall (324), sides (326, 328), and inner walls (330, 332). As shown, sides (326, 328) and inner walls (330, 332) extend downwardly toward lower housing portion (318).

Lower housing portion (318) may include a bottom wall (334), sides (336, 338), and inner walls (340, 342). Sides (336, 338) and inner walls (340, 342) may extend upwardly toward upper housing portion (316). Top and bottom walls (324, 334) are shown as being generally planer and opposing one another to collectively form a cavity (344) together with inner walls (330, 332) of upper housing portion (316) and inner walls (340, 342) of lower housing portion (318). Cavity (344) is configured to house biasing feature (314) as described in detail below with reference to FIGS. 12A-12B. As shown in FIGS. 12A-13, inner surfaces of top and bottom walls (324, 334) may include a plurality of stop features (346, 348) that are configured to prevent inward movement of user contact portions (320, 322) beyond a desired amount. Additionally, user contact portions (320, 322) includes a plurality of projections (350, 352) configured to interact with inner surfaces of sides (326, 328) of upper housing portion (316) and inner surfaces of sides (336, 338) of lower housing portion (318) to prevent outward movement of user contact portions (320, 322) beyond a desired amount.

As shown in FIGS. 12A-13, biasing feature (314) includes resilient portions, shown as biasing arms (354, 356) that are disposed generally opposite to one another. Biasing arms (354, 356) are shown as being generally thin flexible members; however, other versions of biasing arms (354, 356) are also envisioned. As shown, biasing arms (354, 356) may be coupled to each other at terminal ends (358, 360). Biasing arm (354) includes an inner surface (362) and an outer surface (364). Similarly, biasing arm (356) includes an inner surface (366) and an outer surface (368). Inner surface (362) of biasing arm (354) includes a gripping surface (370). Inner surface (366) of biasing arm (356) includes a gripping surface (374). Gripping surfaces (370, 374) may extend parallel to a longitudinal axis defined by cannula tube (124) of cannula (120).

Gripping surfaces (370, 374) may be smooth or non-smooth. For example, a non-smooth surface may include one or more features to lockingly engage cannula tube (124). At least one of gripping surfaces (370, 374) may include at least one tooth configured to lockingly engage with at least one of rib (128) of cannula (120) in the fixed configuration and not lockingly engage with rib (128) of cannula (120) in the movable configuration. As shown in FIGS. 11-13, gripping surface (370, 374) include a plurality of engagement features (372, 376) configured to lockingly engage with ribs (128) disposed on an outer surface of cannula tube (124) of cannula (120) in the fixed configuration and not lockingly engage with ribs (128) disposed on the outer surface of cannula tube (124) in the movable configuration. Alternatively, gripping surfaces (370, 374) may include a smooth surface (not shown) that is configured to frictionally engage ribs (128) of cannula (120) in the fixed configuration and not frictionally engage ribs (128) of cannula (120) in the movable configuration.

Depth limiter (310) is movable by the user (U) between a movable configuration shown in FIG. 12A and a fixed configuration shown in FIG. 12B. In other words, depth limiter (310) may be selectively actuated from the fixed configuration having a first effective diameter (ED1) to the movable configuration having a second effective diameter (ED2) to couple depth limiter (310) from cannula tube (124). Additionally, depth limiter (310) may be selectively actuated from the fixed configuration to the movable configuration to decouple depth limiter (310) from cannula tube (124). As shown, first effective diameter (ED1) is smaller than second effective diameter (ED2). FIG. 12A shows a top plan view of depth limiter (310) of FIG. 11 coupled with cannula tube (124) of FIG. 5 which is shown in cross-section. Upper housing portion (316) of depth limiter (310) is removed in FIGS. 12A-12B to reveal depth limiter (310) in the movable configuration allowing for axial movement of depth limiter (310) relative to cannula tube (124) when actuated by the user (U).

Particularly, gripping surface (370) may be movably coupled with biasing arm (354) and gripping surface (374) may be movably coupled with biasing arm (356) from the fixed configuration to the movable configuration when respective user contact portions (320, 322) are actuated by user. For example, in the movable configuration of FIG. 12A, gripping surfaces (370, 374) collectively form the second effective diameter (ED2) that allows for axial movement of depth limiter (310) relative to an outer diameter of cannula tube (124) of cannula (120). In other words, actuation of user contact portions (320, 322) is configured to respectively cause biasing arms (354, 356) to move gripping surfaces (370, 374) radially outward to selectively disengage cannula (120) in the movable configuration. As shown, gripping surface (370) is radially offset from the user contact portions (320, 322) by approximately 90 degrees, and gripping surface (374) is radially offset from the user contact portion (320, 322) by approximately 90 degrees.

As shown, user contact portions (320, 322) may be actuated by the user (U) using thumb and index fingers. However, the user (U) may depress user contact portions (320, 322) in other ways (e.g., using one or more fingers and the palm). By pinching surfaces (378, 380) of user contact portions (320, 322), gripping surfaces (370, 374) spread apart for disengagement. In the movable configuration, the virtual diameter defined by opposing gripping surfaces (370, 374) is larger than that of cannula tube (124), allowing for free movement of depth limiter (310) to any user-specified depth along cannula tube (124). As shown, user contact portions (320, 322) are disposed circumferentially opposite one another; however, other arrangements of user contact portions (320, 322) are also envisioned. As shown, user contact portions (320, 322) include surfaces (378, 380) for enhanced gripping by the user (U). Surfaces (378, 380) may include features (not shown) to allow for more thorough sterilization, should depth limiter (310) be reusable.

FIG. 12B shows a top plan view of depth limiter (310) and cannula tube (124) of FIG. 12A, but with depth limiter (310) in a fixed configuration that restricts axial movement of depth limiter (310) relative to cannula tube (124). The user (U) may release gripping surfaces (370, 374) from FIG. 12A from the outer surface of cannula tube (124), so that biasing arms (354, 356) return to the fixed configuration. Gripping surfaces (370, 374) are disposed circumferentially opposite one another and are configured to directly contact circumferentially opposite sides of cannula (120) in the fixed configuration. In the fixed configuration, gripping surfaces (370, 374) collectively form a first effective diameter (ED1) that restricts axial movement of depth limiter (310) relative to cannula (120) by directly contacting cannula (120) at discrete regions. As shown, the first effective diameter (ED1) defined by gripping surfaces (370, 374) is smaller than the outer diameter cannula tube (124) when biasing arms (354, 356) of biasing feature (314) are in the fixed configuration. The fixed configuration is the resting configuration. As shown, gripping surfaces (370, 374) do not completely (or entirely) surround cannula tube (124) of cannula (120) in either the fixed configuration or the movable configuration. Instead, gripping surfaces (370, 374) are spaced apart from one another in both of the fixed and movable configurations and separated by gaps (266, 268).

Depth limiter (310) is shown to have a low-profile form. Depth limiter (310) may nest onto proximal end of cannula tube (124) for transport and/or storage. Depth limiter (310) also includes simple to operate pinch-to release controls. Depth limiter (310) may be reusable or disposable. For example, depth limiter (310) may be injection molded for a disposable model. Alternatively, depth limiter (310) may be and stamped, machined, and/or metal-injection molded for a re-usable model. In some versions, depth limiter (310) is completely formed of metal. Depth limiter (310) may fit robotic and laparoscopic instruments, which provides less throw away medical trash and medical facilities (e.g., hospitals) do not have to stock as many different SKUs.

C. Third Exemplary Depth Limiter

Figure 14:
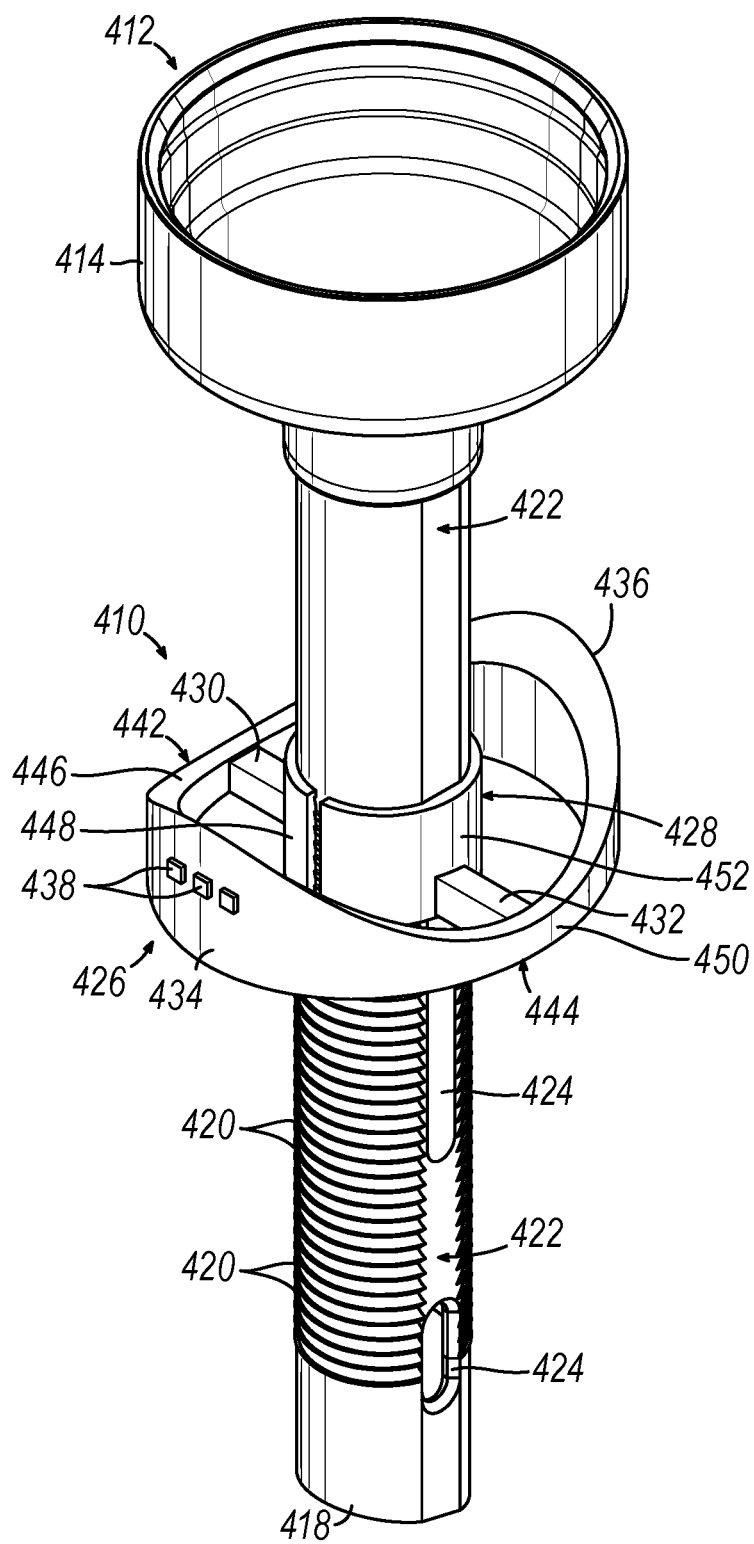
FIG. 14 depicts a perspective view of another exemplary cannula coupled with a third exemplary depth limiter, where the depth limiter is in a fixed configuration that restricts axial movement of the depth limiter relative to a cannula tube of the cannula.
Figure 15:
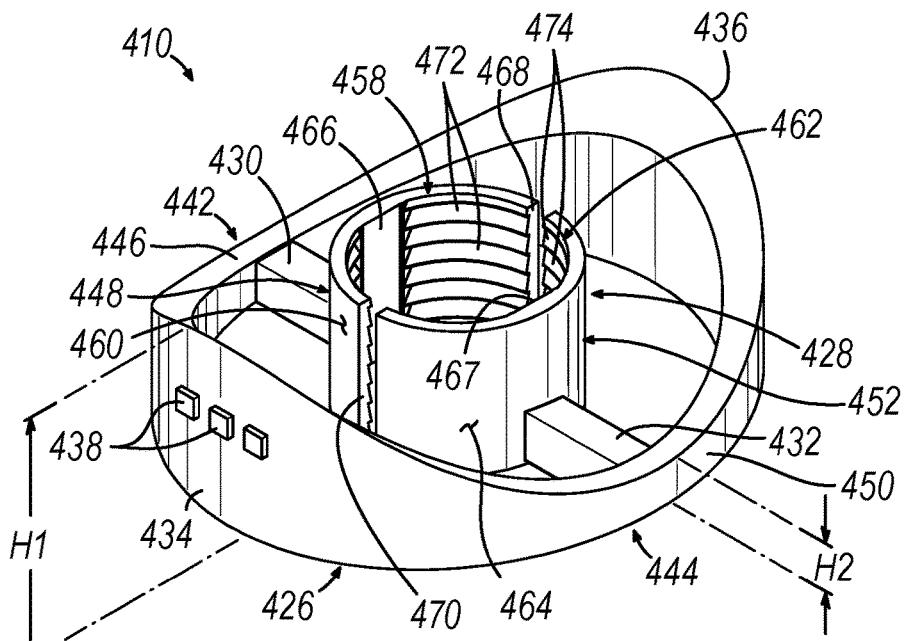
FIG. 15 depicts a perspective view of the depth limiter of FIG. 14.
Figure 16A:
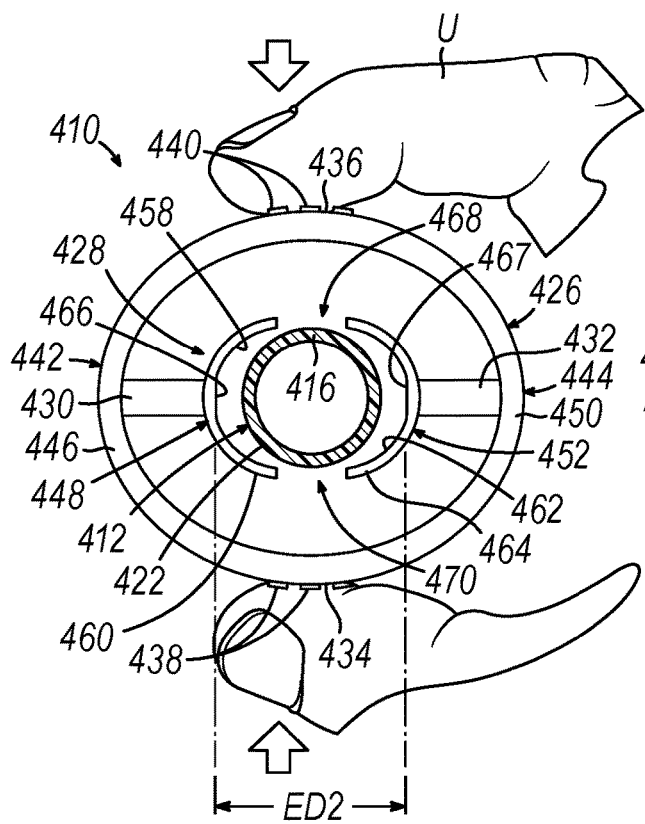
FIG. 16A depicts a top plan view of the depth limiter and the cannula tube of FIG. 14 with the cannula tube being shown in cross-section, where the depth limiter is in a movable configuration allowing for axial movement of the depth limiter relative to the cannula tube when actuated by a user.
Figure 16B:
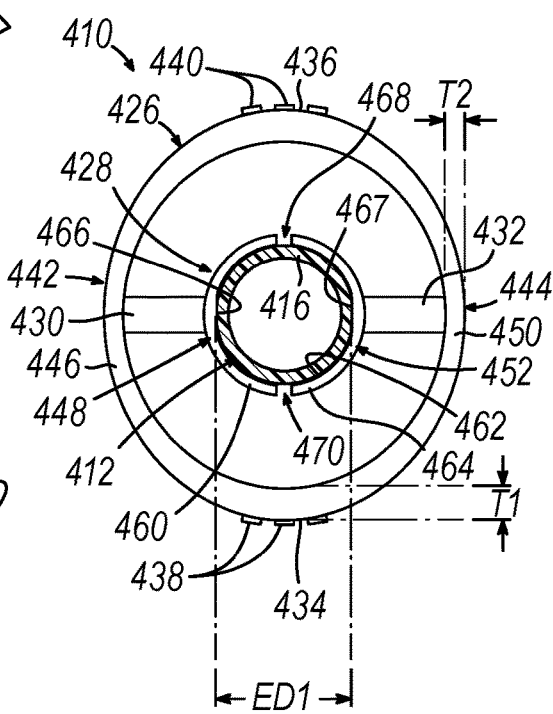
FIG. 16B depicts a top plan view of the depth limiter and the cannula tube of FIG. 16A, but with the depth limiter in the fixed configuration of FIG. 14.

FIGS. 14-16B show a third exemplary depth limiter (410) coupled with an exemplary cannula (412). Particularly, FIG. 14 shows a perspective view of depth limiter (410) in a fixed configuration that restricts axial movement of depth limiter (410) relative to cannula (412). FIG. 15 shows a perspective view of depth limiter (410) of FIG. 14. Similar to cannula (120), cannula (412) may have a bell-shaped hub (414) at a proximal end thereof, and an elongate cannula tube (416) extending distally from hub (414) and terminating at an angled cannula tip (418). An outer surface of cannula tube (416) includes a plurality of tissue gripping features in the form of ribs (420) arranged axially along a medial portion of cannula tube (416). As shown in FIGS. 14 and 16A-16B, cannula tube (416) includes slotted portions (422) formed opposite one another. Slotted portions (422) extend longitudinally along cannula tube (416). Slotted portions (422) have a reduced outer diameter as compared the remainder of cannula tube (416). Slotted portions (422) include apertures or features (424) disposed on a distal portion of cannula tube (416) and is generally adjacent to cannula tip (418). As shown, slotted portions (422) extend along the complete axial length of cannula tube (416); however, slotted portions (422) may extend only along a portion of the axial length of cannula tube (416) in some versions.

Depth limiter (410) may include an outer portion (426), an inner portion (428), and arms (430, 432) that that are disposed between outer and inner portions (426, 428). As shown in FIG. 16B, outer portion (426) may be generally oval in shape when in the fixed configuration (i.e., the resting configuration). Outer portion (426) includes user contact portions (434, 436) that may be disposed circumferentially opposite from one another. User contact portions (434, 436) are configured to be actuated by the user (U). As shown, user contact portions (434, 436) include raised protuberances (438, 440) that are configured to enhance the gripping of respective user contact portions (434, 436) and/or allow the user to tactilely locate user contact portions (434, 436) without visualization.

Depth limiter (410) includes biasing features (442, 444) that are disposed opposite one another. Biasing feature (442) includes a resilient portion (446), arm (430), and a gripping member (448). Similarly, biasing feature (444) includes a resilient portion (450), arm (432), and a gripping member (452). Resilient portions (446, 450) may be configured to flex as shown in FIG. 16A when respective user contact features (434, 436) are actuated by the user (U). This flexibility may be due in part to the geometry of depth limiter (410), such that the relative cross-sectional thickness of resilient portions (446, 450) is less than the relative cross-sectional thickness of the outer portion (426) that includes user contact portions (434, 436). For example, as shown in FIG. 15, the height (H1) of user contact portions (434, 436) is greater than the height (H2) of resilient portions (446, 450). Similarly, as shown in FIG. 16B, the thickness (T1) of user contact portions (434, 436) is greater than the thickness (T2) of resilient portions (446, 450).

Gripping member (448) includes a gripping surface (458) and an outer surface (460). Gripping surface (458) is movably coupled with resilient portion (446) from the fixed configuration to the movable configuration when user contact portion (434) is actuated by the user (U). Similarly, gripping member (452) includes a gripping surface (462) and an outer surface (464). Gripping surfaces (458, 462) are sized and configured to receive cannula tube (416) at discrete regions. Gripping surfaces (458, 462) may extend parallel to a longitudinal axis defined by cannula tube (416) of cannula (412). Gripping surface (462) is movably coupled with resilient portion (446) from the fixed configuration to the movable configuration when user contact portion (434) is actuated by the user (U). Gripping surfaces (458, 462) include respective slotted portions (466, 467) that are configured to align with slotted portions (422) of cannula tube (416) in the fixed configuration. Gripping surfaces (458, 462) of gripping members (448, 452) are spaced apart from one another in both of the closed and movable configurations by gaps (468, 470).

Gripping surfaces (458, 462) may be smooth or non-smooth. For example, a non-smooth surface may include one or more features to lockingly engage cannula tube (416). At least one of gripping surfaces (458, 462) may include at least one engagement feature configured to lockingly engage with at least one of rib (420) of cannula (412) in the fixed configuration and not lockingly engage with rib (420) of cannula (412) in the movable configuration. As shown in FIG. 15, gripping surfaces (458, 462) include a plurality of engagement features, shown as teeth (472, 474), configured to lockingly engage with ribs (420) disposed on an outer surface of cannula tube (416) of cannula (412) in the fixed configuration and not lockingly engage with ribs (420) disposed on the outer surface of cannula tube (416) in the movable configuration. Alternatively, gripping surfaces (458, 462) may include a smooth surface (not shown) that is configured to frictionally engage ribs (420) of cannula tube (416) of cannula (412) in the fixed configuration and not frictionally engage ribs (420) of cannula (412) in the movable configuration.

Depth limiter (410) is movable by the user (U) between a movable configuration shown in FIG. 16A and a fixed configuration shown in FIG. 16B. In other words, depth limiter (410) may be selectively actuated from the fixed configuration having a first effective diameter (ED1) to the movable configuration having a second effective diameter (ED2) to decouple depth limiter (410) from cannula tube (416), and from the movable configuration to the fixed configuration to couple depth limiter (410) to cannula tube (416). As shown, first effective diameter (ED1) is smaller than second effective diameter (ED2). FIG. 16A shows a top plan view of depth limiter (410) and cannula tube (416) of FIG. 14 with cannula tube (416) being shown in cross-section, where depth limiter (410) is in a movable configuration allowing for axial movement of depth limiter (410) relative to cannula tube (416) when actuated by the user (U). In the movable configuration of FIG. 16A, gripping surfaces (458, 462) collectively form second effective diameter (ED2) that allows for axial movement of depth limiter (410) relative to an outer diameter of cannula tube (416) of cannula (412). In other words, actuation of user contact portions (434, 436) is configured to respectively cause arms (430, 432) to move gripping surfaces (458, 462) outwardly to selectively disengage cannula (412) in the movable configuration.

As shown, user contact portions (434, 436) are configured to be actuated by the user (U) using thumb and index fingers. However, the user (U) may depress user contact portions (434, 436) in other ways (e.g., using one or more fingers and the palm). By pinching user contact portions (434, 436), gripping surfaces (458, 462) spread apart for disengagement. In the movable configuration, the virtual diameter defined by opposing gripping surfaces (458, 462) is larger than that of cannula tube (416), allowing for free movement of depth limiter (410) to any user-specified depth along cannula tube (416). As shown, gripping surface (458) is radially offset from the user contact portions (434, 436) by approximately 90 degrees, and gripping surface (462) is radially offset from the user contact portions (434, 436) by approximately 90 degrees.

FIG. 16B shows a top plan view of depth limiter (410) and cannula tube (416) of FIG. 16A, but with depth limiter (410) in the fixed configuration of FIG. 14. The user (U) may release gripping surfaces (458, 462) from FIG. 16A from the outer surface of cannula tube (124), so that arms (430, 432) return to the fixed configuration. Gripping surfaces (458, 462) are disposed circumferentially opposite one another and are configured to directly contact circumferentially opposite sides of cannula (412) in the fixed configuration. In the fixed configuration, gripping surfaces (458, 462) collectively form a first effective diameter (ED1) that restricts axial movement of depth limiter (410) relative to cannula (412) by directly contacting cannula (412).

As shown, the first effective diameter (ED1), defined by gripping surfaces (458, 462), is smaller than the outer diameter of cannula tube (416) when arms (430, 432) are in the fixed configuration. The fixed configuration may be considered the resting configuration. As shown, gripping surfaces (458, 462) do not completely (or entirely) surround cannula tube (416) of cannula (412) in either the fixed configuration or the movable configuration. Instead, gripping surfaces (458, 462) are spaced apart from one another in both of the fixed and movable configurations and separated by gaps (468, 470). In the fixed configuration of FIG. 16B, gripping surfaces (458, 462) are shown to grip less than half of the circumference of cannula tube (416) at discrete regions; however, this may vary.

Depth limiter (410) may be reusable or disposable. For example, depth limiter (410) may be injection molded for an inexpensive disposable model. Depth limiter (410) may be integrally formed together as a unitary piece. For example, depth limiter (410) may be formed from a polymeric material (e.g., plastic). Alternatively, depth limiter (410) may be and stamped, machined, and/or metal-injection molded for a re-usable model.

D. Fourth Exemplary Depth Limiter

Figure 17:
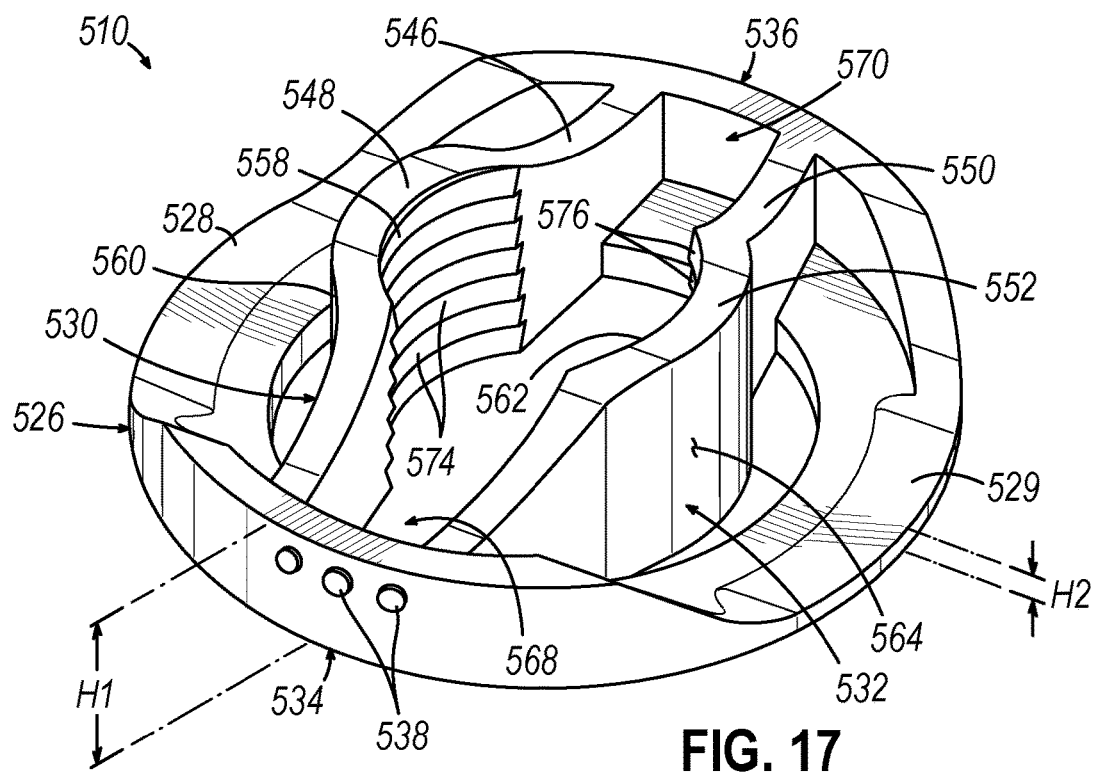
FIG. 17 depicts a perspective view of a fourth exemplary depth limiter.
Figure 18A:
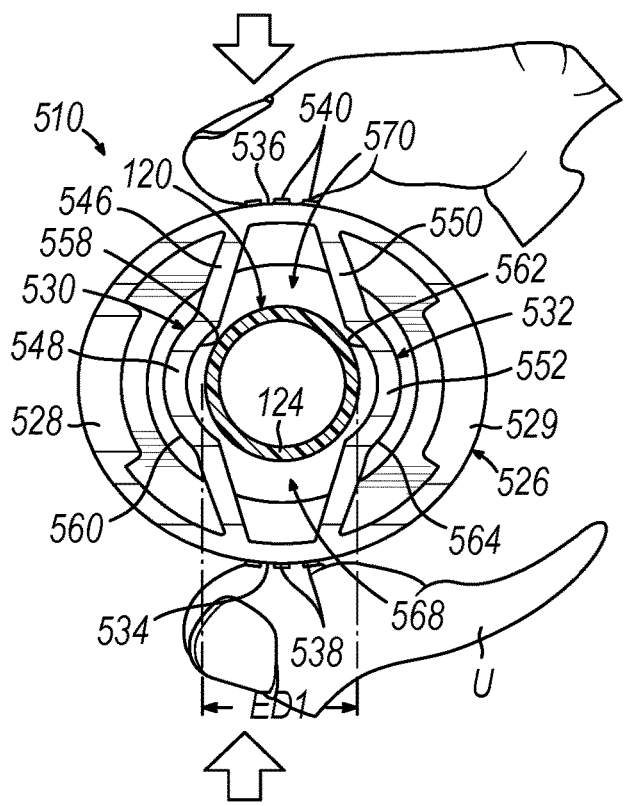
FIG. 18A depicts a top plan view of the depth limiter of FIG. 17 coupled with the cannula tube of FIG. 6 that is shown in cross-section, where the depth limiter is in a movable configuration that allows for axial movement of the depth limiter relative to the cannula tube when actuated by a user.
Figure 18B:
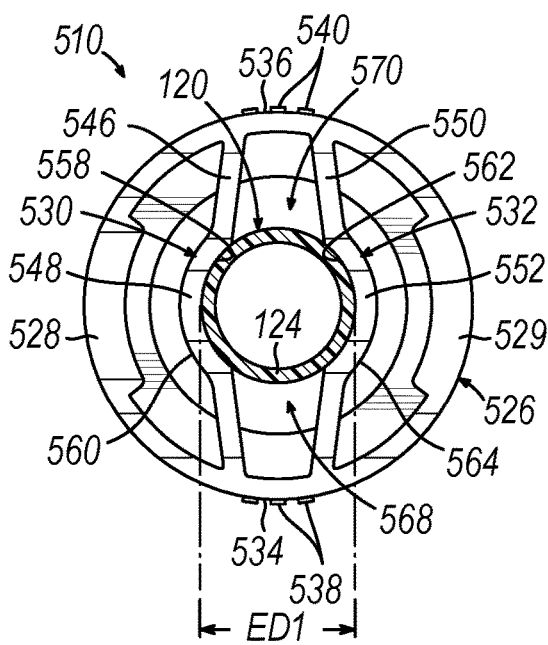
FIG. 18B depicts a top plan view of the depth limiter and the cannula tube of FIG. 18A, but with the depth limiter in a fixed configuration that restricts axial movement of the depth limiter relative to the cannula tube.

FIGS. 17-18B show a fourth exemplary depth limiter (510) coupled with cannula (120). Similar to depth limiter (410) that includes an outer portion (426), depth limiter (510) includes an outer portion (526) as well as biasing features (530, 532) that that are disposed within outer portion (526). Outer portion (526) includes user contact portions (534, 536), similar to user contact portions (434, 436), that are disposed opposite from one another. User contact portions (534, 536) are configured to be actuated by the user (U). As shown, user contact portions (534, 536) include raised protuberances (538, 540) that are configured to enhance the gripping of respective user contact portions (534, 536) and/or allow the user to tactilely locate user contact portions (534, 536) without visualization. Outer portion (526) may include thin portions (528, 529) that are disposed opposite one another and between user contact portions (534, 536).

Biasing features (530, 532) are disposed opposite one another. Biasing feature (530) includes a resilient portion (546) and a gripping feature (548). Similarly, biasing feature (532) includes a resilient portion (550), and a gripping feature (552). Resilient portions (546, 550) may be configured to outwardly flex as shown in FIG. 18A when respective user contact features (534, 536) are actuated by user (U). This flexibility may be due in part to the geometry of depth limiter (510), such that the relative cross-sectional thickness of resilient portions (546, 550) is less than the relative cross-sectional thickness of outer portion (526) that includes user contact portions (534,436) and thin portions (528, 529). For example, as shown in FIG. 17, the height (H1) of user contact portions (534,436) is greater than the height (H2) of thin portions (528, 529). Thin portions (528, 5292) may be shorter than gripping features (548, 552) to affect the magnitude of outward flexing of biasing features (530, 532).

Gripping feature (548) includes a gripping surface (558) and an outer surface (560). Similarly, gripping feature (552) includes a gripping surface (562) and an outer surface (564). Gripping surfaces (558, 562) may be movably coupled with resilient portions (546, 550) from the fixed configuration to the movable configuration when user contact portion (534, 536) are actuated by the user (U). Gripping surfaces (558, 562) may be sized and configured to receive cannula tube (124) of cannula (120) at discrete regions. Gripping surfaces (558, 562) may extend parallel to a longitudinal axis defined by cannula tube (124) of cannula (120). Gripping surfaces (558, 562) of gripping features (548, 552) are spaced apart from one another in both of the fixed and movable configurations by gaps (568, 570).

Gripping surfaces (558, 562) may be smooth or non-smooth. For example, a non-smooth surface may include one or more features to lockingly engage cannula tube (124). At least one of gripping surfaces (558, 562) may include at least one engagement feature configured to lockingly engage with at least one of rib (128) of cannula (120) in the fixed configuration and not lockingly engage with rib (128) of cannula (120) in the movable configuration. As shown in FIGS. 18A-18B, gripping surface (558, 562) include a plurality of engagement features, shown as teeth (574, 576), configured to lockingly engage with ribs (128) disposed on an outer surface of cannula tube (124) of cannula (120) in the fixed configuration and not lockingly engage with ribs (128) disposed on the outer surface of cannula tube (124) in the movable configuration. Alternatively, while not shown, gripping surfaces (558, 562) may include a smooth surface (not shown) that is configured to frictionally engage ribs (128) of cannula tube (124) of cannula (120) in the fixed configuration and not frictionally engage ribs (128) of cannula (120) in the movable configuration.

Depth limiter (510) is movable by the user (U) between a movable configuration shown in FIG. 18A and a fixed configuration shown in FIG. 18B. In other words, depth limiter (510) may be selectively actuated from the fixed configuration having a first effective diameter (ED1) to the movable configuration having a second effective diameter (ED2) to couple depth limiter (510) with cannula tube (124). Depth limiter (510) may be selectively actuated from fixed configuration to the movable configuration to decouple depth limiter (510) to cannula tube (124). As shown, first effective diameter (ED1) is smaller than second effective diameter (ED2). FIG. 18A shows a top plan view of depth limiter (510) and cannula tube (124) of FIG. 5 with cannula tube (124) being shown in cross-section, where depth limiter (510) is in a movable configuration allowing for axial movement of depth limiter (510) relative to cannula tube (124) when actuated by the user (U). In the movable configuration of FIG. 18A, gripping surfaces (558, 562) collectively form the second effective diameter (ED2) that allows for axial movement of depth limiter (510) relative to an outer diameter of cannula tube (124) of cannula (120). As shown in FIG. 18B, outer portion (526) may be generally oval in shape when in the fixed configuration also considered the resting configuration.

As shown, user contact portions (534, 536) are configured to be actuated by the user (U) using thumb and index fingers. However, the user (U) may depress user contact portions (534, 536) in other ways (e.g., using one or more fingers and the palm). By pinching user contact portions (534, 536), gripping surfaces (558, 562) may spread apart for disengagement. In the movable configuration, the virtual diameter defined by opposing gripping surfaces (558, 562) is larger than that of cannula tube (124), allowing for free movement of depth limiter (510) to any user-specified depth along cannula tube (124). As shown, gripping surface (558) is radially offset from the user contact portions (534, 536) by approximately 90 degrees, and gripping surface (562) is radially offset from the user contact portions (534, 536) by approximately 90 degrees.

FIG. 18B shows a top plan view of depth limiter (510) and cannula tube (124) of FIG. 18A, but with depth limiter (510) in the fixed configuration of FIG. 14. As shown in FIG. 18B, outer portion (526) is generally circular in shape when in the fixed configuration also considered the resting configuration. The user (U) may release gripping surfaces (558, 562) from FIG. 18A from the outer surface of cannula tube (124), so that biasing features (530, 532) return to the fixed configuration. Gripping surfaces (558, 562) are disposed circumferentially opposite one another and are configured to directly contact circumferentially opposite sides of cannula (120) in the fixed configuration. In the fixed configuration, gripping surfaces (558, 562) collectively form a first effective diameter (ED1) that restricts axial movement of depth limiter (510) relative to cannula (120) by directly contacting cannula (120). First effective diameter (ED1) defined by gripping surfaces (558, 562) is smaller than the outer diameter cannula tube (124) when biasing features (530, 532) are in the fixed configuration. As shown, gripping surfaces (558, 562) do not completely (or entirely) surround cannula tube (124) of cannula (120) in either the fixed configuration or the movable configuration. Instead, gripping surfaces (558, 562) are spaced apart from one another in both of the fixed and movable configurations and separated by gaps (568, 570). In the fixed configuration of FIG. 18B, gripping surfaces (558, 562) are shown to collectively grip less than half of the circumference of cannula tube (124); however, this may vary.

Depth limiter (510) may be reusable or disposable. For example, depth limiter (510) may be injection molded for an inexpensive disposable model. Depth limiter (510) may be integrally formed together as a unitary piece. For example, depth limiter (510) may be formed from a polymeric material (e.g., plastic). Alternatively, depth limiter (510) may be metal-injection molded for a re-usable model.

E. Fifth Exemplary Depth Limiter

Figure 19:
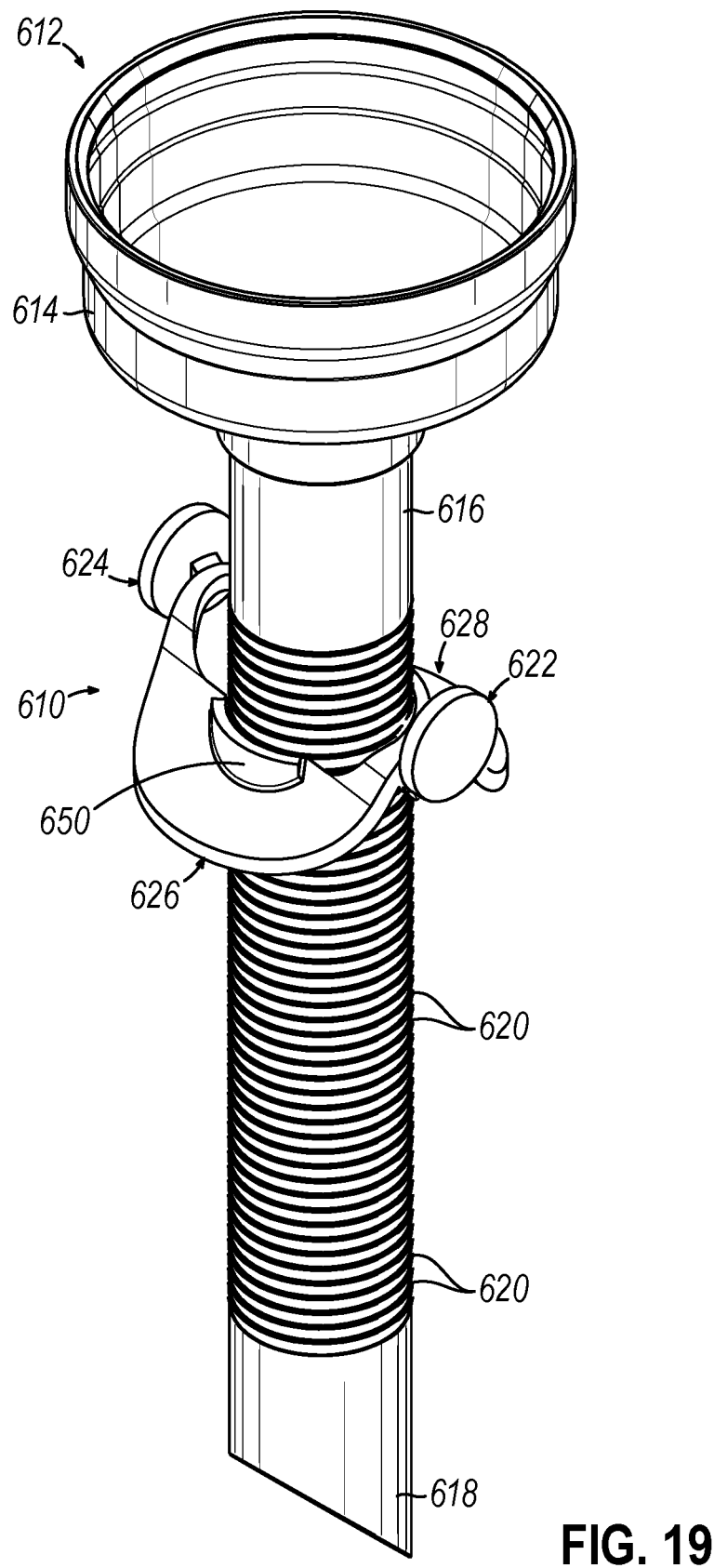
FIG. 19 depicts a perspective view of another exemplary cannula coupled with a fifth exemplary depth limiter, where the depth limiter is in a fixed configuration that restricts axial movement of the depth limiter relative to a cannula tube of the cannula.

FIGS. 19-22B show a fifth exemplary depth limiter (610) coupled with an exemplary cannula (612). Particularly, FIG. 19 shows a perspective view of depth limiter (610) in a fixed configuration that restricts axial movement of depth limiter (610) relative to cannula (612). Similar to cannula (120), cannula (612) includes a bell-shaped hub (614) at a proximal end thereof, and an elongate cannula tube (616) extending distally from hub (414) and terminating at an angled cannula tip (618). An outer surface of cannula tube (616) includes a plurality of tissue gripping features in the form of ribs (620) arranged axially along a medial portion of cannula tube (616).

Figure 20:
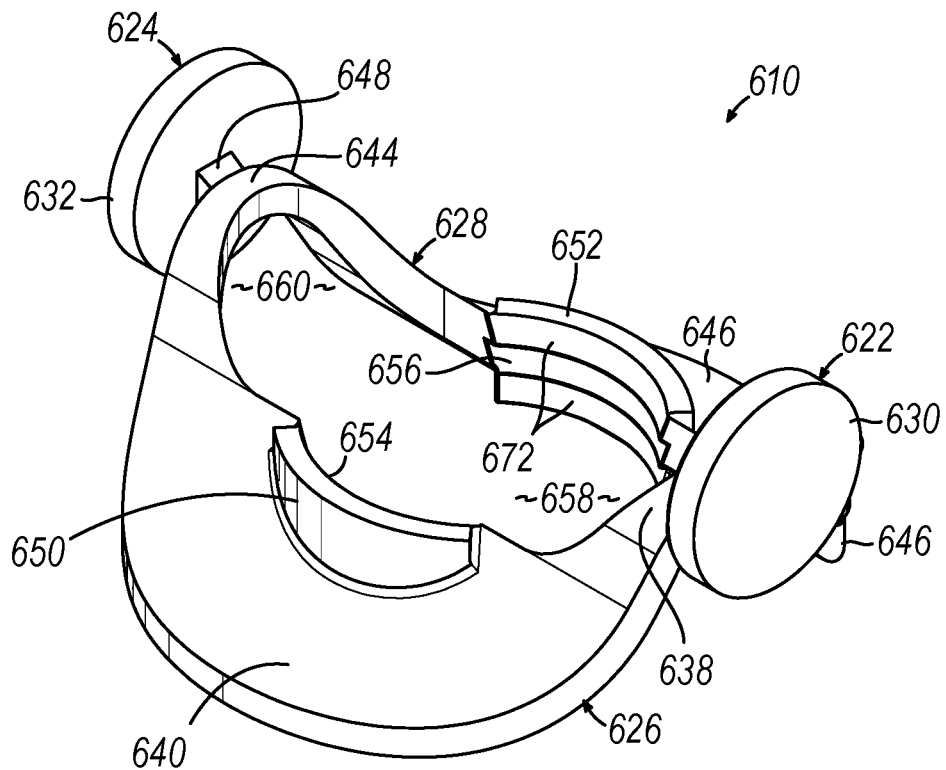
FIG. 20 depicts a perspective view of the depth limiter of FIG. 19.
Figure 21:
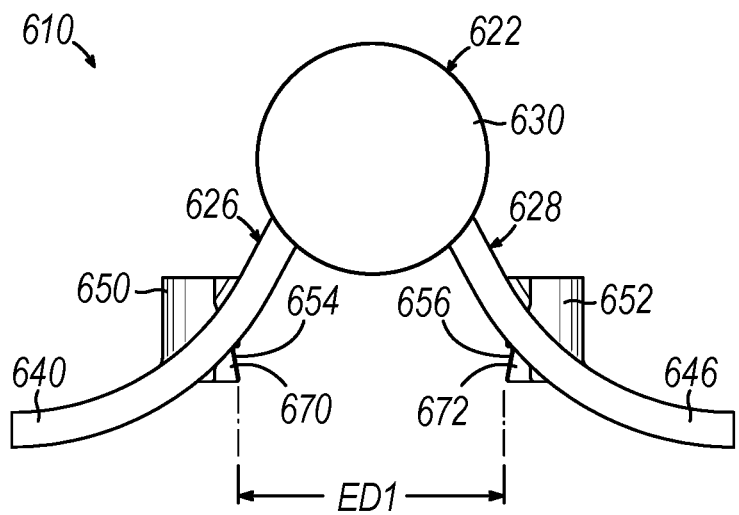
FIG. 21 depicts a side elevational view of the depth limiter of FIG. 20.

FIG. 20 shows a perspective view of depth limiter (610) of FIG. 19, and FIG. 21 shows a side elevational view of depth limiter (610) of FIG. 20. Depth limiter (610) includes user contact portions (622, 624) and biasing features (626, 628). User contact portions (622, 624) may be disposed opposite from one another, and are configured to be actuated by the user (U). As shown, user contact portions (622, 624) include buttons (630, 632). Buttons (630, 632) may include gripping features that are configured to enhance the gripping of respective user contact portions (622, 624) and/or allow the user (U) to locate user contact portions (622, 624) without visualization.

Biasing features (626, 628) may be disposed opposite one another. Biasing feature (626) includes a resilient portion (shown as thin portion (638)) and a thick portion (640). Thin portion (638) is coupled with user contact portion (622) using a connecting portion (642). Similarly, biasing feature (628) includes a resilient portion (shown as thin portion (644)) and a thick portion (646). Thin portion (644) is coupled with user contact portion (624) using a connecting portion (648). Thick portion (640) includes a gripping feature (650). Similarly, thick portion (646) includes a gripping feature (652). Gripping features (650, 652) are configured to flex outwardly as shown in FIG. 22A when respective user contact features (622, 624) are actuated by the user (U). This flexibility may be due in part to the geometry of depth limiter (610), such that the relative cross-sectional thickness of thin portions (638, 644) is less than the relative cross-sectional thickness of thick portions (640, 646). As shown in FIG. 22B, thickness (T1) of thick portions (640, 646) is greater than thickness (T2) of thin portions (638, 644).

Gripping feature (650) includes a gripping surface (654) that is movably coupled with thin portion (638) from the fixed configuration to the movable configuration when user contact portion (622) is actuated by the user (U). Similarly, gripping feature (652) includes a gripping surface (656) that is movably coupled with thin portion (644) from the fixed configuration to the movable configuration when user contact portion (622) is actuated by the user (U). Gripping surfaces (654, 656) are sized and configured to receive cannula tube (616) at discrete regions. Gripping surfaces (654, 656) of gripping features (650, 652) are spaced apart from one another by gaps (658, 660) in both of the fixed and movable configurations. Gripping surfaces (654, 656) may extend parallel to a longitudinal axis defined by cannula tube (616) of cannula (612).

Gripping surfaces (654, 656) may be smooth or non-smooth. For example, a non-smooth surface may include one or more features to lockingly engage cannula tube (616). At least one of gripping surfaces (654, 656) may include at least one engagement feature configured to lockingly engage with at least one of ribs (620) of cannula (612) in the fixed configuration and not lockingly engage with ribs (620) of cannula (612) in the movable configuration. As shown in FIGS. 22A-22B, gripping surfaces (654, 656) each include a plurality of engagement features, shown as teeth (670, 672), configured to lockingly engage with ribs (620) disposed on an outer surface of cannula tube (616) of cannula (612) in the fixed configuration and not lockingly engage with ribs (620) disposed on the outer surface of cannula tube (616) in the movable configuration. Three individual teeth (670, 672) are shown, and are arranged mimic the shape of scallops of cannula (612). Alternatively, while not shown, gripping surfaces (654, 656) may include a smooth surface (not shown) that is configured to frictionally engage ribs (620) of cannula tube (616) of cannula (612) in the fixed configuration and not frictionally engage ribs (620) of cannula (612) in the movable configuration.

Depth limiter (610) may be movable by the user (U) between the movable configuration shown in FIG. 22A and the fixed configuration shown in FIG. 22B. In other words, depth limiter (610) may be selectively actuated from the fixed configuration having a first effective diameter (ED1) to the movable configuration having a second effective diameter (ED2) to couple depth limiter (610) with cannula tube (616). Additionally, depth limiter (610) is movable by the user (U) from the fixed configuration to the movable configuration to decouple depth limiter (610) from cannula tube (616). Particularly, FIG. 22A shows a top plan view of depth limiter (610) and cannula tube (124) of FIG. 5 with cannula tube (616) being shown in cross-section, where depth limiter (610) is in the movable configuration allowing for axial movement of depth limiter (610) relative to cannula tube (616) when actuated by the user (U).

In the movable configuration of FIG. 22A, gripping surfaces (654, 656) collectively form the second effective diameter (ED2) that allows for axial movement of depth limiter (610) relative to an outer diameter of cannula tube (616) of cannula (612). In other words, actuation of user contact portions (622, 624) is configured to respectively cause biasing features (626, 628) to move gripping surfaces (654, 656) outwardly to selectively disengage cannula (612) in the movable configuration. As shown in FIGS. 22A-22B, the first effective diameter (ED1) is smaller than the second effective diameter (ED2). As shown, user contact portions (622, 624) are configured to be actuated by the user (U) using thumb and index fingers. However, the user (U) may depress user contact portions (622, 624) in other ways (e.g., using one or more fingers and the palm). In the movable configuration, the virtual diameter defined by opposing gripping surfaces (654, 656) is larger than that of cannula tube (616), allowing for free movement of depth limiter (610) to any user-specified depth along cannula tube (616). In other words, the thickness of thin portions (638, 644) cause the effective diameter to expand from the first effective diameter (ED1) to the second effective diameter (ED2) due to bi-axial stresses induced caused by pinching user contact features (622, 624). As shown, gripping surface (654) is radially offset from the user contact portions (622, 624) by approximately 90 degrees, and gripping surface (656) is radially offset from the user contact portions (622, 624) by approximately 90 degrees.

Pushing user contact portions (622, 624) along first axis causes gripping features (650, 652) to expand along a perpendicular second axis (push in one direction with the effect being in a perpendicular direction). User pinch force deflects perpendicular surfaces inward, causing gripping surfaces (654, 656) to move outwardly and up to unlatch. Depth limiter (610) has a biaxially curved shape to induce desired flexing in the perpendicular direction when pinched or pulled in the other direction. Perpendicular to these features, at the more proximal end, are thin portions (638, 644) (i.e., a slot, oval, or other curved shape removes more material from the inner surfaces here). This thinning causes flexibility, such that when the user pinches from buttons (630, 632), the stresses induced in the part cause gripping features (650, 652) to rotate up and away from the cannula (e.g., in a gull-wing motion). The dimensions of thin portions (638, 644) may be manipulated to allow for easier actuation forces versus higher clamp forces and/or to account for different material characteristics.

FIG. 22B shows a top plan view of depth limiter (610) and cannula tube (616) of FIG. 22A, but with depth limiter (610) in a fixed configuration that restricts axial movement of depth limiter (610) relative to cannula tube (616). In the fixed configuration, gripping surfaces (654, 656) collectively form a first effective diameter (ED1) that restricts axial movement of depth limiter (610) relative to cannula (612) by directly contacting cannula (612). The user (U) may release gripping surfaces (654, 656) from FIG. 22A from the outer surface of cannula tube (616), so that biasing features (626, 628) return to the fixed configuration. Gripping surfaces (654, 656) may be disposed circumferentially opposite one another and may be configured to directly contact circumferentially opposite sides of cannula (612) in the fixed configuration.

First effective diameter (ED1) defined by gripping surfaces (654, 656) is smaller than the outer diameter cannula tube (616) when biasing features (626, 628) are in the fixed configuration. The fixed configuration may be considered the resting configuration. As shown, gripping surfaces (654, 656) do not completely (or entirely) surround cannula tube (616) of cannula (612) in either the fixed configuration or the movable configuration. Instead, gripping surfaces (654, 656) may be spaced apart from one another in both of the fixed and movable configurations and separated by gaps (658, 660). In the fixed configuration of FIG. 18B, gripping surfaces (654, 656) are shown to collectively grip less than half of the circumference of cannula tube (616); however, this may vary. As shown, depth limiter (610) is generally circular in shape when in the fixed configuration (i.e., the resting configuration).

Depth limiter (610) may be reusable or disposable. For example, depth limiter (610) may be injection molded for an inexpensive disposable model. Depth limiter (610) may be integrally formed together as a unitary piece. For example, depth limiter (610) may be singular injection molded component would enable very low cost of goods and a relatively high clamping force versus relatively low user-actuated declamping force. For example, depth limiter (610) may be formed from a polymeric material (e.g., plastic). Alternatively, depth limiter (610) may be metal-injection molded for a re-usable model. Additionally, in some versions, depth limiter (610) may be modified for more effective stamping, machining, and welding processes.

F. Sixth Exemplary Depth Limiter

Figure 23:
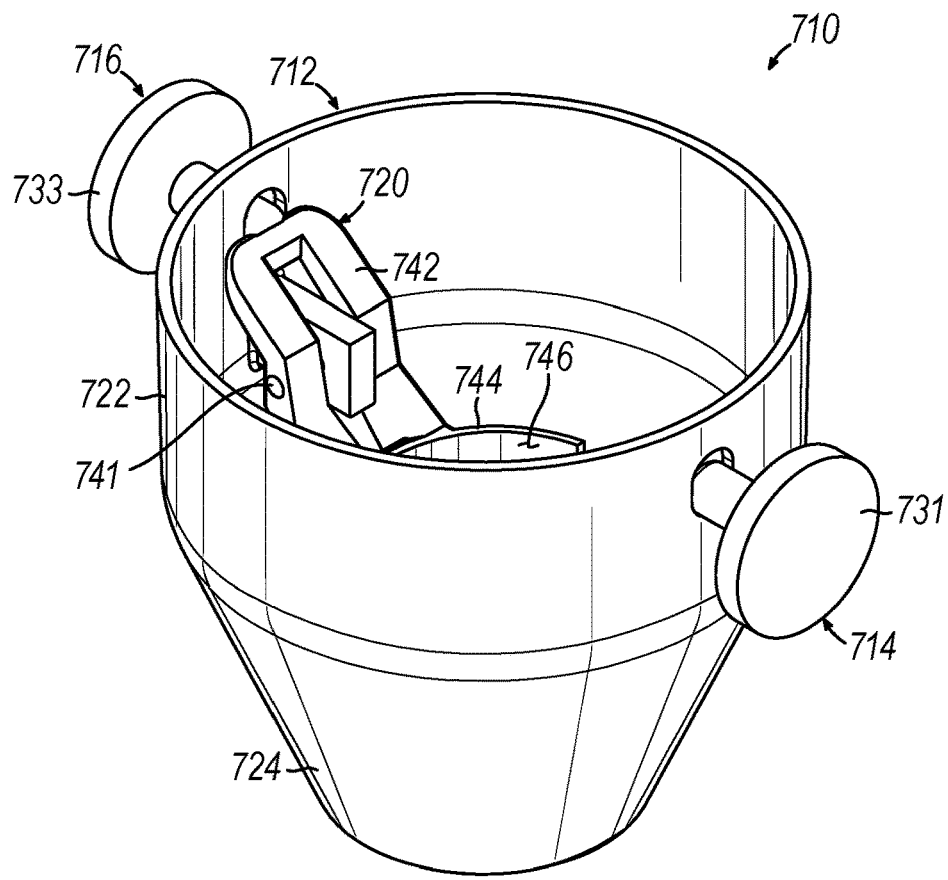
FIG. 23 depicts a perspective view of a sixth exemplary depth limiter.
Figure 24:
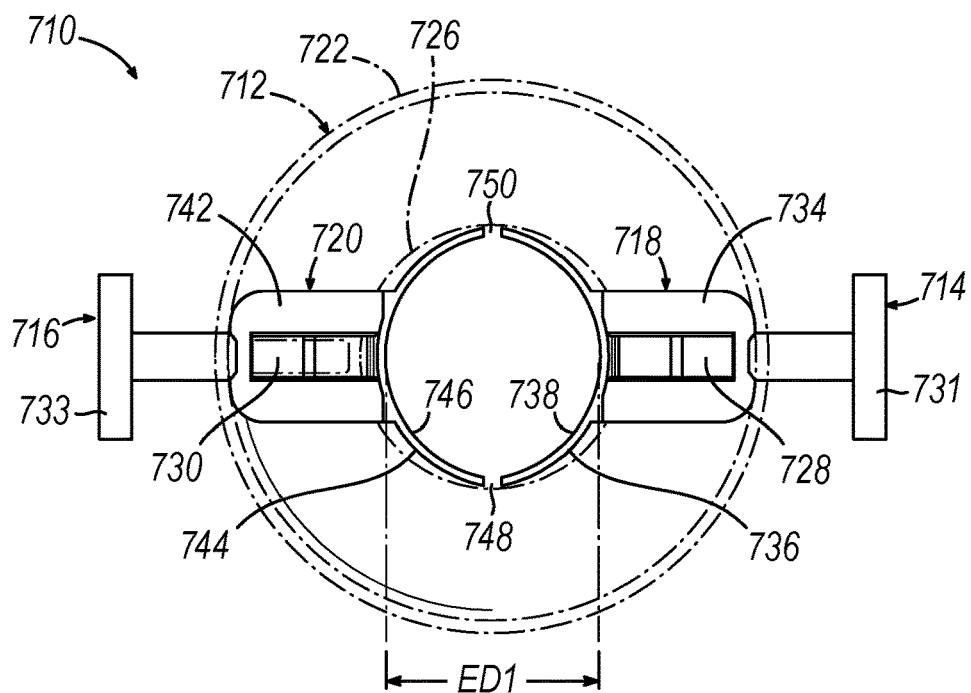
FIG. 24 depicts a top plan view of the depth limiter of FIG. 23, with the housing being shown in phantom to expose biasing features.

FIGS. 23-25B show a sixth exemplary depth limiter (710). Particularly, FIG. 23 shows a perspective view of depth limiter (710), and FIG. 24 shows a top plan view of depth limiter (710) of FIG. 23. As shown, depth limiter (710) includes a housing (712), user contact portions (714, 716), and biasing features (718, 720). Housing (712) may include a cylindrical portion (722) and a truncated cone portion (724) with an aperture (726) extending therethrough configured to receive cannula tube (124) of cannula (120). In some versions, truncated cone portion (724) may be shorter, such that the overall height of depth limiter (710) may be shorter and more compact. As shown, cylindrical portion (722) includes projections (728, 730) that are project radially inward. User contact portions (714, 716), which may be in the form of buttons, may be disposed opposite from one another, and may be configured to be actuated by the user (U). User contact portions (714, 716) include outer surfaces (731, 733) that are shown as being generally circular. While not shown, outer surfaces (731, 733) may include gripping features that are configured to enhance the gripping of respective user contact portions (714, 716) and/or allow the user (U) to locate user contact portions (714, 716) without visualization.

Biasing features (718, 720) may be disposed opposite one another, and may act as opposing spring-retained levers. As shown, biasing feature (718) includes a resilient portion (shown as a spring (732) in FIGS. 25A-25B) and a biasing arm (734). Spring (732) is coiled around a pin (735) and is received by projection (728) to bias biasing arm (734). Biasing arm (734) includes a gripping member (736) that includes a gripping surface (738) configured to receive cannula tube (124). Similarly, biasing feature (720) includes a resilient portion (shown as a spring (740) in FIGS. 25A-25B) and a biasing arm (742). Spring (740) is coiled around a pin (741) and is received by projection (730) to bias biasing arm (742). Biasing arm (742) includes a gripping member (744) that includes a gripping surface (746) configured to receive another portion of cannula tube (124). In FIG. 24, housing (712) is shown in phantom to expose biasing arms (734, 742) of biasing features (718, 720).

Gripping surfaces (738, 746) are sized and configured to receive cannula tube (124) at discrete regions. Gripping surfaces (738, 746) may extend parallel to a longitudinal axis defined by cannula tube (124) of cannula (120). Gripping surfaces (738, 746) of gripping members (736, 744) are spaced apart from one another by gaps (748, 750) in both of the fixed and movable configurations. Gripping surfaces (738, 746) are shown as cylindrical clamping surfaces that interfere with cannula (120) and provide clamping pressure. Gripping surfaces (738, 746) may be smooth or non-smooth. As shown, gripping surfaces (738, 746) may include a smooth arcuate surface that is configured to frictionally engage ribs (128) of cannula tube (124) of cannula (120) in the fixed configuration and not frictionally engage ribs (128) of cannula (120) in the movable configuration. Alternatively, while not shown, a non-smooth surface may include one or more features to lockingly engage cannula tube (124). For example, at least one of gripping surfaces (738, 746) may include at least one engagement feature (e.g., teeth) configured to lockingly engage with at least one of rib (128) of cannula (120) in the fixed configuration and not lockingly engage with rib (128) of cannula (120) in the movable configuration.

Figure 25A:
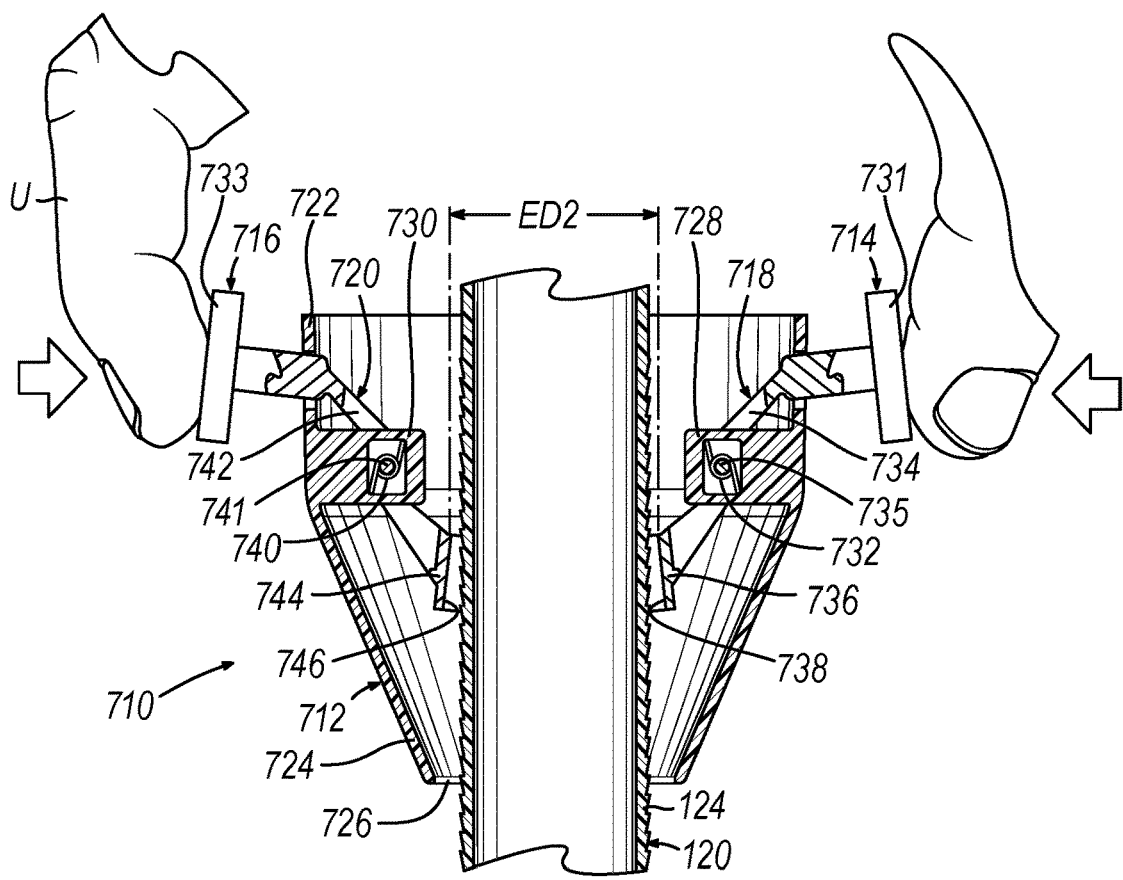
FIG. 25A depicts a side partial cross-sectional view of the depth limiter of FIG. 23 coupled with the cannula tube of FIG. 5, where the depth limiter is in a movable configuration that allows for axial movement of the depth limiter relative to the cannula tube when actuated by a user.
Figure 25B:
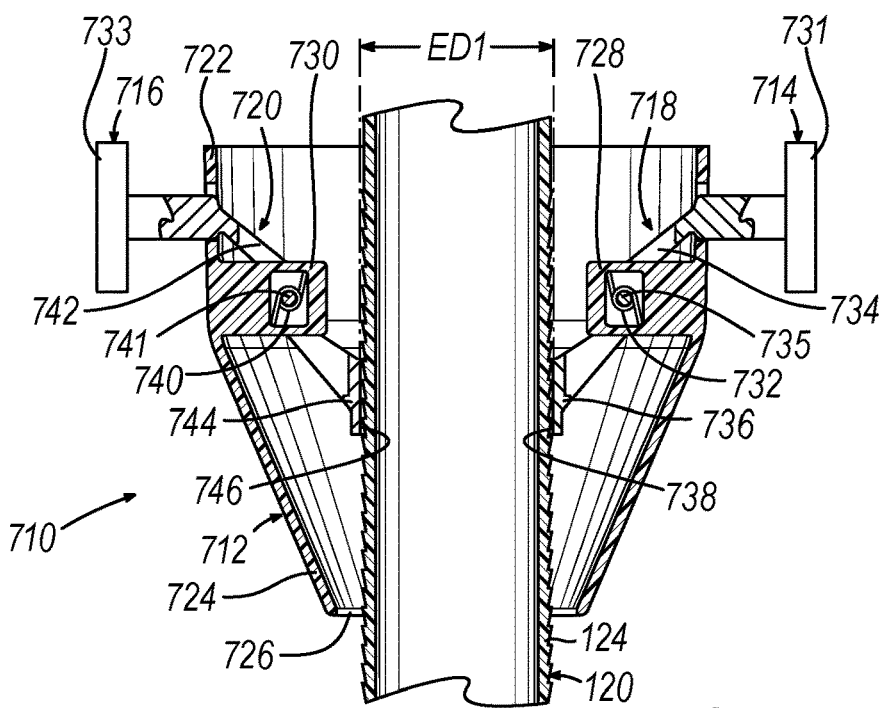
FIG. 25B depicts a side partial cross-sectional plan view of the depth limiter and the cannula tube of FIG. 25A, but with the depth limiter in a fixed configuration that restricts axial movement of the depth limiter relative to the cannula tube.

Depth limiter (710) is movable by the user (U) between a movable configuration shown in FIG. 25A and a fixed configuration shown in FIG. 25B. In other words, depth limiter (710) may be selectively actuated from the fixed configuration having a first effective diameter (ED1) to the movable configuration having a second effective diameter (ED2) to decouple depth limiter (710) from cannula tube (124). Additionally, depth limiter (710) is movable by the user (U) from the movable configuration to the fixed configuration to couple depth limiter (710) to cannula tube (124). Particularly, FIG. 25A shows a side partial cross-sectional view of depth limiter (710) of FIG. 23 coupled with cannula tube (124) of FIG. 5, where depth limiter (710) is in a movable configuration that allows for axial movement of depth limiter relative (710) to cannula tube (124) when actuated by the user (U).

In the movable configuration of FIG. 25A, gripping surfaces (738, 746) collectively form the second effective diameter (ED2) that allows for axial movement of depth limiter (710) relative to an outer diameter of cannula tube (124) of cannula (120). In other words, actuation of user contact portions (714, 716) is configured to respectively cause biasing features (718, 720) to move gripping surfaces (738, 746) radially outward to selectively disengage cannula (120) in the movable configuration. As shown in FIGS. 25A-25B, the first effective diameter (ED1) is smaller than the second effective diameter (ED2). As shown, user contact portions (714, 716) are configured to be actuated by the user (U) using thumb and index fingers. However, the user (U) may depress user contact portions (714, 716) in other ways (e.g., using one or more fingers and the palm).

As shown in FIG. 25A, biasing arms (734, 742) are pivotably mounted within housing (712) to clamp onto cannula (120) using gripping members (736, 744). Biasing arms (734, 742) clamp passively, engaged by springs (732, 740), and the user unclamps biasing arms (734, 742) by pushing on user contact portions (714, 716) which tilts the levers (shown as biasing arms (734, 742)). This interference is passively biased by the force of springs (732, 740) which push biasing arms (734, 742) to be in the fixed configuration, thereby clamping onto outer surface of cannula tube (124). The user unclamps biasing arms (734, 742) by pushing on user contact portions (714, 716), thus rotating the biasing arms (734, 742), and pushing against springs (732, 740), allowing depth limiter (710) to be repositioned. Springs (732, 740) may be torsion springs and/or axial springs to push biasing arms (734, 742) passively towards the fixed configuration.

FIG. 25B shows a side partial cross-sectional plan view of depth limiter (710) and cannula tube (124) of FIG. 25A, but with depth limiter (710) in the fixed configuration that restricts axial movement of depth limiter (710) relative to cannula tube (124). In the fixed configuration, gripping surfaces (738, 746) collectively form a first effective diameter (ED1) that restricts axial movement of depth limiter (710) relative to cannula (120) by directly contacting cannula (120). First effective diameter (ED1) defined by gripping surfaces (738, 746) is smaller than the outer diameter cannula tube (124) when biasing features (718, 720) are in the fixed configuration. The fixed configuration is the resting configuration. Gripping surfaces (738, 746) are disposed circumferentially opposite one another and are configured to directly contact circumferentially opposite sides of cannula (120) in the fixed configuration. As shown, gripping surfaces (738, 746) do not completely (or entirely) surround cannula tube (124) of cannula (120) in either the fixed configuration or the movable configuration. Instead, gripping surfaces (738, 746) are spaced apart from one another in both of the fixed and movable configurations and separated by gaps (748, 750).

Depth limiter (710) may be reusable or disposable. For example, depth limiter (710) may be injection molded for an inexpensive disposable model. For example, depth limiter (710) may be formed from a polymeric material (e.g., plastic). Alternatively, depth limiter (710) may be metal-injection molded for a re-usable model. Additionally, in some versions, depth limiter (710) may be modified for more effective stamping, machining, and welding processes. In some versions, depth limiter (710) may be completely formed of metal.

G. Seventh Exemplary Depth Limiter

Figure 26:
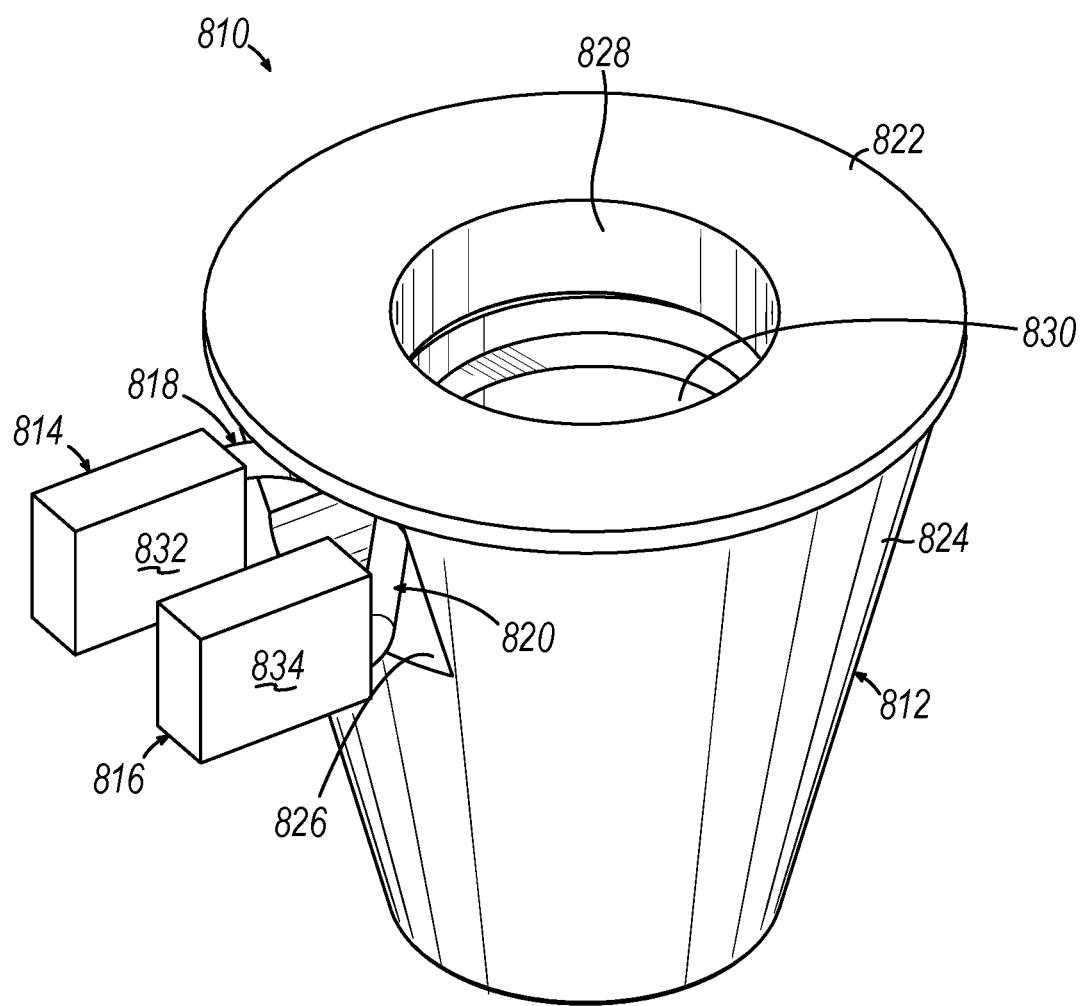
FIG. 26 depicts a perspective view of a seventh exemplary depth limiter.
Figure 27A:
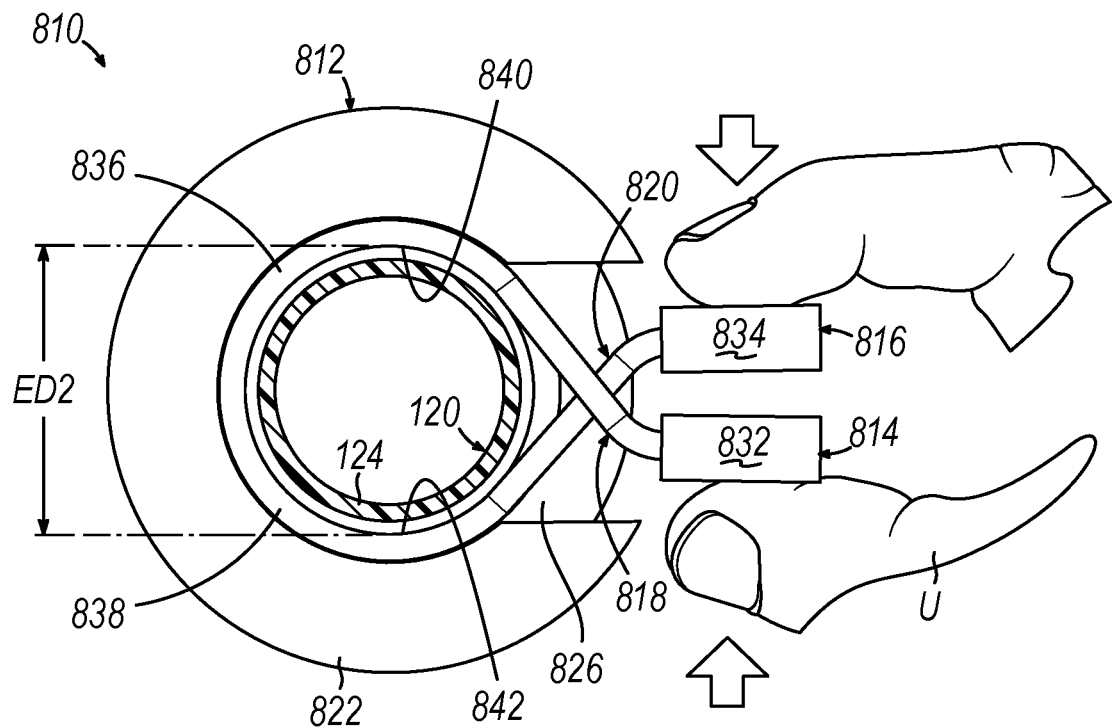
FIG. 27A depicts a top plan view of the depth limiter of FIG. 26 coupled with the cannula tube of FIG. 6 shown in cross-section, where an upper housing portion of the depth limiter is partially removed to show the depth limiter in a movable configuration allowing for axial movement of the depth limiter relative to the cannula tube when actuated by a user.
Figure 27B:
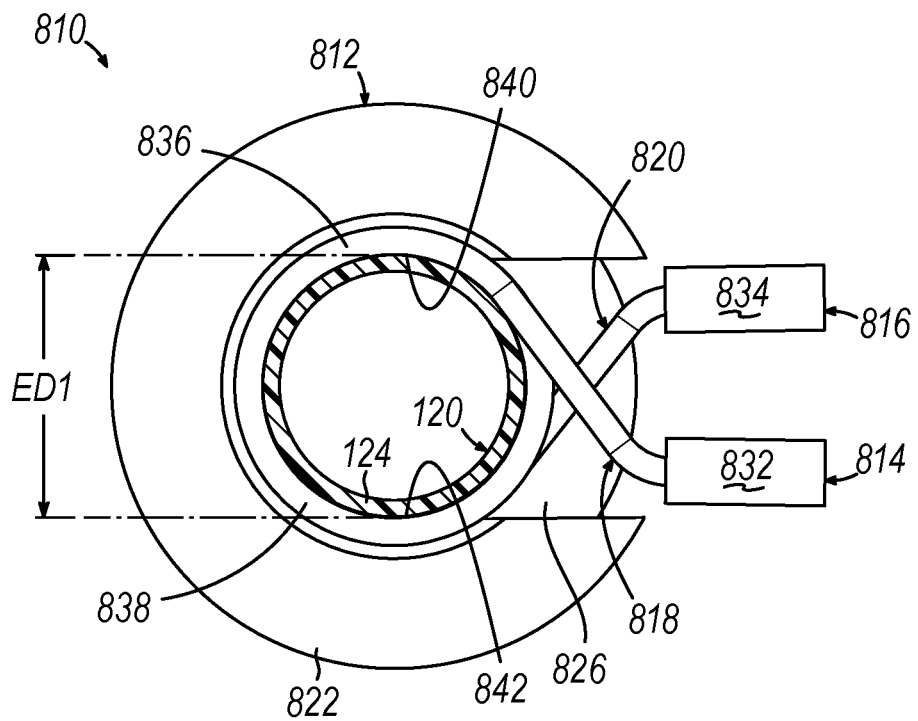
FIG. 27B depicts a top plan view of the depth limiter and the cannula tube of FIG. 27A, but with the depth limiter in a fixed configuration that restricts axial movement of the depth limiter relative to the cannula tube.
Figure 28:
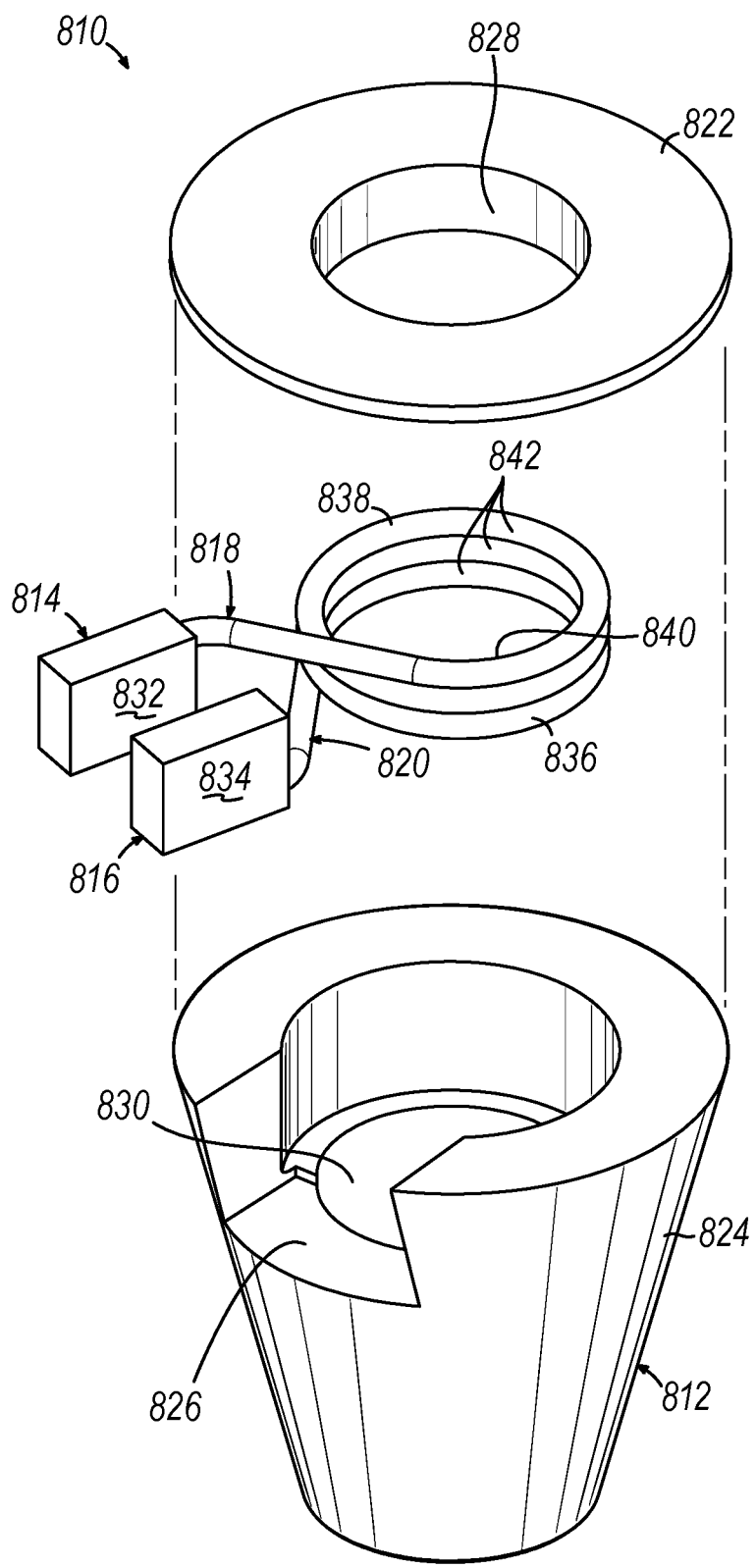
FIG. 28 depicts an exploded view of the depth limiter of FIG. 26.

FIGS. 26-28 show a seventh exemplary depth limiter (810). Particularly, FIG. 26 shows a perspective view of depth limiter (810) and FIG. 28 shows an exploded view of depth limiter (810) of FIG. 26. As shown, depth limiter (810) includes a housing (812), user contact portions (814, 816), and biasing features (818, 820). Housing (812) may include a cylindrical top (822) and a truncated cone portion (824) that includes a side aperture (826). In some versions, truncated cone portion (824) may be shorter, such that the overall height of depth limiter (810) is shorter and more compact. As shown, cylindrical top (822) includes an aperture (828) and truncated cone portion (824) includes an aperture (830). Apertures (828, 830) are configured to receive cannula tube (124) of cannula (120) therethrough. As shown, biasing features (818, 820) collectively form a torsion spring. Biasing features (818, 820) are housed within housing (812) to prevent tissue pinching between biasing features (818, 820) and act as an abutment surface against the abdominal wall (2) shown in FIG. 3A-3D.

User contact portions (814, 816) may be disposed generally adjacent one another (e.g., on the same side of cannula tube (124)), and are configured to be actuated by the user (U). For example, user contact portions (814, 816) may include overmold on the ends, and/or any other ergonomically suitable end-treatments. As shown, user contact portions (814, 816) are disposed on the same side of depth limiter (810), and are not disposed directly opposite one another. User contact portions (814, 816) include outer surfaces (832, 834) that are shown as being generally rectangular. While not shown, outer surfaces (832, 834) may include gripping features that are configured to enhance the gripping of respective user contact portions (814, 816) and/or allow the user to locate user contact portions (814, 816) without visualization.

Biasing feature (818) includes a resilient portion (shown as a coil portion (836)). Similarly, biasing feature (820) includes a resilient portion (shown as a coil portion (838)). Coil portions (836, 838) respectively include gripping surfaces (840, 842). Gripping surfaces (840, 842) are sized and configured to receive cannula tube (124). Gripping surfaces (840, 842) may extend parallel to a longitudinal axis defined by cannula tube (124) of cannula (120). Gripping surfaces (840, 842) of coil portions (836, 838) completely surround cannula tube (124) in both of the fixed and movable configurations. Gripping surfaces (840, 842) may be smooth or non-smooth. As shown, gripping surfaces (840, 842) may include a smooth arcuate surface that is configured to frictionally engage ribs (128) of cannula tube (124) of cannula (120) in the fixed configuration and not frictionally engage ribs (128) of cannula (120) in the movable configuration. Alternatively, while not shown, a non-smooth surface may include one or more features to lockingly engage cannula tube (124). For example, at least one of gripping surfaces (840, 842) may include at least one engagement feature (e.g. teeth) configured to lockingly engage with at least one of rib (128) of cannula (120) in the fixed configuration and not lockingly engage with rib (128) of cannula (120) in the movable configuration. Gripping surfaces (840, 842) may nestle onto the outer surface on cannula (120) to increase retention force.

Depth limiter (810) is movable by the user (U) between a movable configuration shown in FIG. 27A and a fixed configuration shown in FIG. 27B. In other words, depth limiter (810) may be selectively actuated from the fixed configuration having a first effective diameter (ED1) to the movable configuration having a second effective diameter (ED2) to couple depth limiter (810) from cannula tube (124). Additionally, depth limiter (810) is movable by the user (U) from the fixed configuration to the movable configuration to decouple depth limiter (810) from cannula tube (124). Particularly, FIG. 27A shows a top plan view of depth limiter (810) of FIG. 26 coupled with cannula tube (124) of FIG. 6 shown in cross-section, where the upper housing (shown as cylindrical top (822)) of depth limiter (810) is removed to show depth limiter (810) in the movable configuration.

In the movable configuration of FIG. 27A, gripping surfaces (840, 842) collectively form second effective diameter (ED2) that allows for axial movement of depth limiter (810) relative to an outer diameter of cannula tube (124) of cannula (120). In other words, actuation of user contact portions (814, 816) is configured to respectively cause biasing features (818, 820) to expand gripping surfaces (840, 842) radially outward to selectively disengage cannula (120) in the movable configuration. As shown, user contact portions (814, 816) are configured to be actuated by the user (U) using thumb and index fingers. However, the user (U) may depress user contact portions (814, 816) in other ways (e.g., using one or more fingers and the palm). The user (U) may increase the inner diameter of gripping surfaces (840, 842) by pinching outer surfaces (832, 834) of user contact portions (814, 816) together. Biasing features (818, 820) are passively engaged to the cannula (120) via spring-force, and are disengaged from cannula (120) by squeezing together two handles (814, 816) attached to its terminal ends, which opens up biasing features (818, 820). Biasing features (818, 820), collectively forming a torsion spring, are sized and configured to provide an interference/compression fit with the cannula (120) in the fixed configuration.

FIG. 27B shows a top plan view of depth limiter (810) and cannula tube (124) of FIG. 27A, but with depth limiter (810) in the fixed configuration that restricts axial movement of depth limiter (810) relative to cannula tube (124). In the fixed configuration, gripping surfaces (840, 842) collectively form a first effective diameter (ED1) that restricts axial movement of depth limiter (810) relative to cannula (120) by directly contacting cannula (120). First effective diameter (ED1) defined by gripping surfaces (840, 842) is smaller than the outer diameter cannula tube (124) when biasing features (818, 820) are in the fixed configuration. The fixed configuration is the resting configuration.

Depth limiter (810) may be reusable or disposable. For example, depth limiter (810) may be injection molded for an inexpensive disposable model. For example, depth limiter (810) may be formed from a polymeric material (e.g., plastic). Alternatively, depth limiter (810) may be metal-injection molded for a re-usable model. Additionally, in some versions, depth limiter (810) may be modified for more effective stamping, machining, and welding processes. In some versions, depth limiter (810) may be completely formed of metal. Depth limiter (810) may provide a high clamping force depending on torsion spring selection. Additionally, as shown, depth limiter (810) includes simple pinch-to-release controls using user contact portions (814, 816).

H. Eighth Exemplary Depth Limiter

Figure 29:
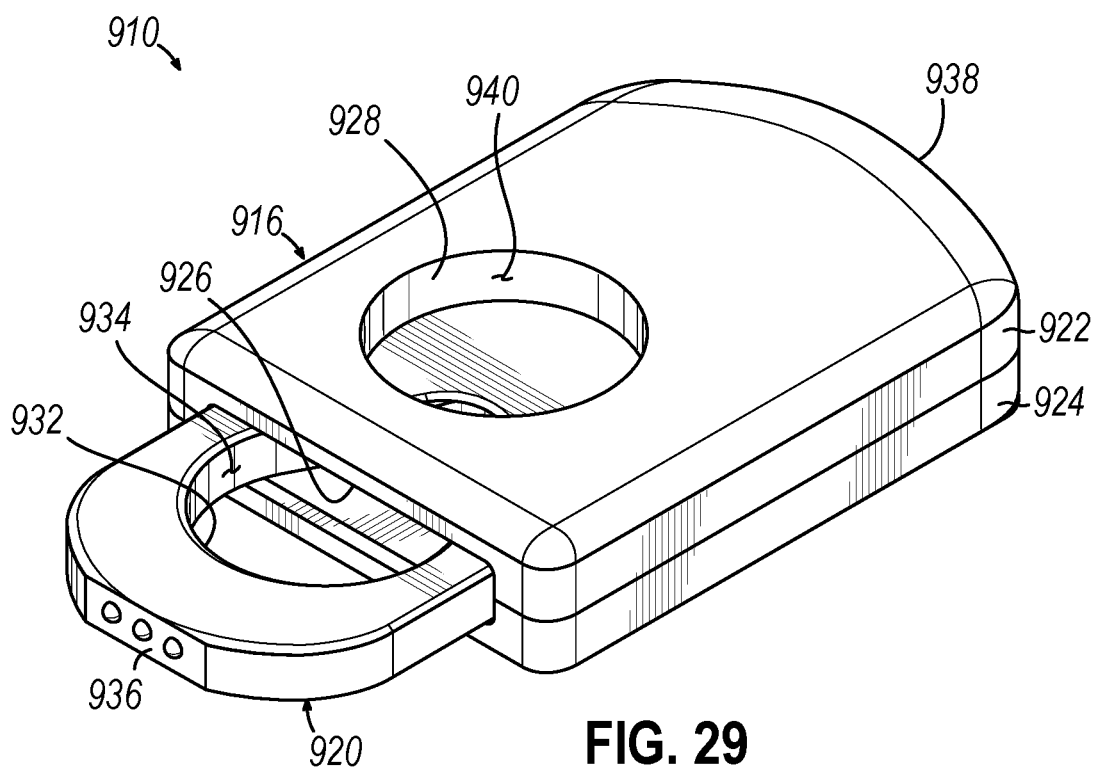
FIG. 29 depicts a perspective view of an eighth exemplary depth limiter.
Figure 30:
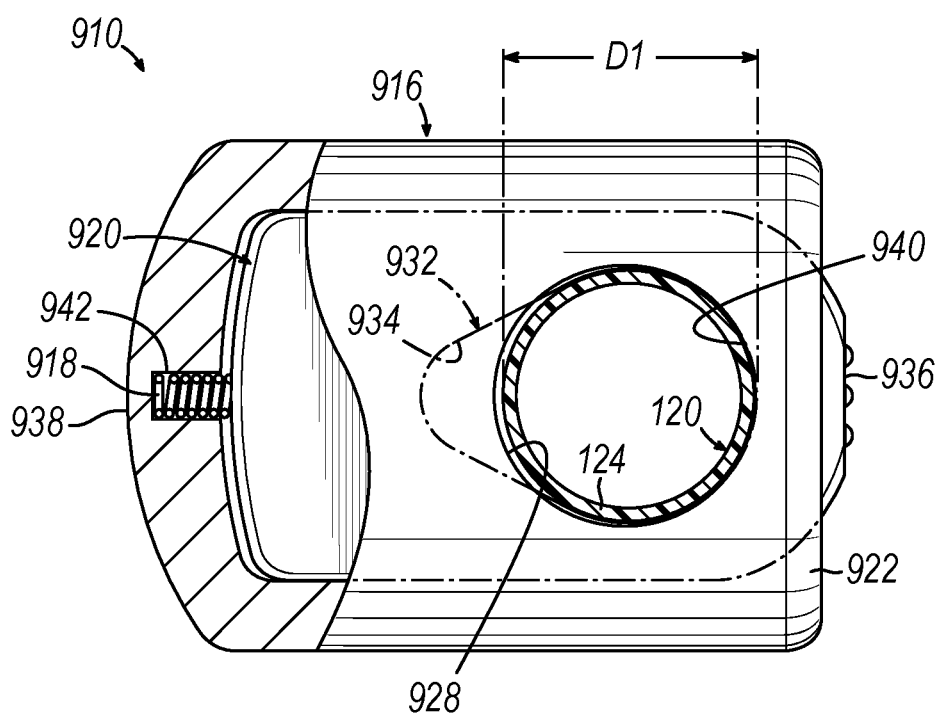
FIG. 30 depicts a partial top sectional view of the depth limiter of FIG. 30 and a cannula tube having a first diameter, where a housing of the depth limiter is partially removed to expose a biasing feature, a slot, and a slidable member, where the cannula tube is positioned between apertures of the housing and the slidable member in a fixed configuration that restricts axial movement of the depth limiter relative to the cannula tube.

FIGS. 29-31B show an eighth exemplary depth limiter (910). Particularly, FIG. 29 shows a perspective view of depth limiter (910) of a surgical access device, and FIG. 30 shows a partial top sectional view of depth limiter (910) of FIG. 29 and a cannula (912). As shown in FIG. 30, cannula (912) includes a cannula tube (914) having a first diameter (D1) configured to be selectively coupled with depth limiter (910).

Depth limiter (910) may include a housing (916), a biasing feature (918), and a slidable member (920). Housing (916) may include opposing upper and lower housing portions (922, 924). Upper and lower housing portions (922, 924) may form a slot (926) configured to receive slidable member (920). Upper housing portion (922) includes an aperture (928) that communicates with slot (926). As show, aperture (928) opens to slot (926) and which may be sized and configured to receive cannula tube (124). Similarly, lower housing portion (924) may include an aperture or a void (not shown) that opens to slot (926), such that upper and lower housing portions (922, 924) may receive collectively cannula tube (124) therethrough. Aperture (928) may extend along a longitudinal axis that is transverse to a length of housing (916). As shown in FIG. 30, housing (916) is partially removed to expose biasing feature (918), slot (926), and slidable member (920). While biasing feature (918) is shown as a single coil spring, a variety of suitable biasing features are envisioned, including the use of multiple biasing features (918), if desired. As shown in FIGS. 30 and 31A, biasing feature (918) is disposed at least partially within slot (926) collectively formed by upper and lower housing portions (922, 924). For example, biasing feature (918) may be at least partially housed within a recess (942).

Slidable member (920) may be disposed at least partially within slot (926). Slidable member (920) includes an aperture (932) extending therethrough. Slidable member (920) may be movably coupled with biasing feature (918) between a fixed configuration and a movable configuration. In the fixed configuration, aperture (928) of upper housing portion (922) and aperture (932) of slidable member (920) are at least partially aligned to restrict axial movement of depth limiter (910) relative to cannula (912). As shown, aperture (932) of slidable member (920) may include a gripping surface (934). Gripping surface (934) is shown as having a tapered oblong shape that is configured to accommodate cannulas (120, 912) having different diameters (D1, D2) in the closed and movable configurations. The tapered oblong interior shape of aperture (932) of slidable member (920) permits use with various sizes of cannulas (120, 912), such that tapered oblong shape allows biasing feature (918) (e.g., a spring) to close down on gripping surface (934) to accommodate different sized cannula tubes (124, 914). In other words, depth limiter (910) may couple with cannula (120) having a smaller diameter and cannula (912) having a larger diameter with a squeeze by the user (U). The squeeze from the user (U) may also release cannula (120, 912) from depth limiter (910) allowing for quick adjustment or removal. As described above, depth limiter (910) may also be used with cannula tube (22) of cannula (20), cannula tube (416) of cannula (412), or other suitable cannulas having a range of outer diameters.

As shown, a terminal end of slidable member (920) includes a user contact portion (936). A side of housing (916) opposite slot (926) acts as a user contact portion (938). As such, user contact portions (936, 938) are disposed generally opposite one another, and are configured to be actuated by the user (U). One or both of user contact portions (936, 938) may include gripping features that are configured to enhance the gripping of respective user contact portions (936, 938) and/or allow the user to locate user contact portions (936, 938) without visualization.

A least a portion of aperture (928) of upper housing portion (922) form gripping surfaces (940). Gripping surfaces (934, 940) are configured to restrict axial movement of depth limiter (910) relative to cannula (912) at discrete regions. Gripping surfaces (934, 940) may extend parallel to a longitudinal axis defined by cannula tube (124) of cannula (120). As shown, gripping surfaces (934, 940) may be smooth arcuate surface that is configured to frictionally engage ribs (not shown) of cannula tube (124) of cannula (120) in the fixed configuration and not frictionally engage ribs (128) of cannula (120) in the movable configuration. Alternatively, while not shown, a non-smooth surface may include one or more features to lockingly engage cannula tube (124). For example, at least one of gripping surfaces (934, 940) may include at least one engagement feature (e.g. teeth) configured to lockingly engage with at least one of rib (128) of cannula (120) in the fixed configuration and not lockingly engage with rib (128) of cannula (120) in the movable configuration. Gripping surfaces (934, 940) may nestle onto an outer surface on cannula (120) to increase retention force. Gripping surfaces (934, 940) form a central aperture that is configured to extend along a central surgical access device axis (A).

Figure 31B:
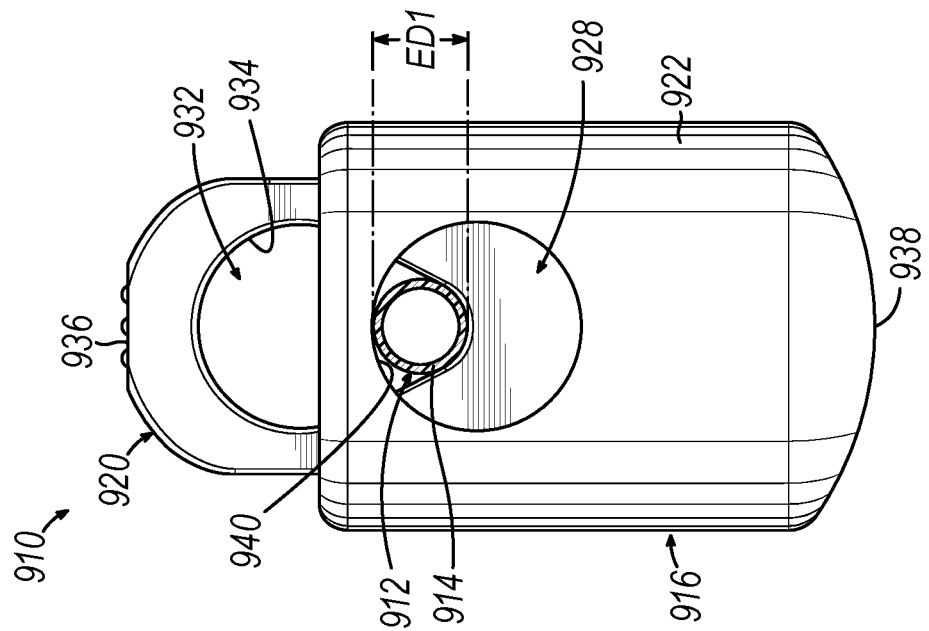
FIG. 31B depicts a top plan view of the depth limiter and the cannula tube of FIG. 31A with the cannula tube shown in cross-section, but with the depth limiter in the fixed configuration similar to FIG. 30.
Figure 31A:
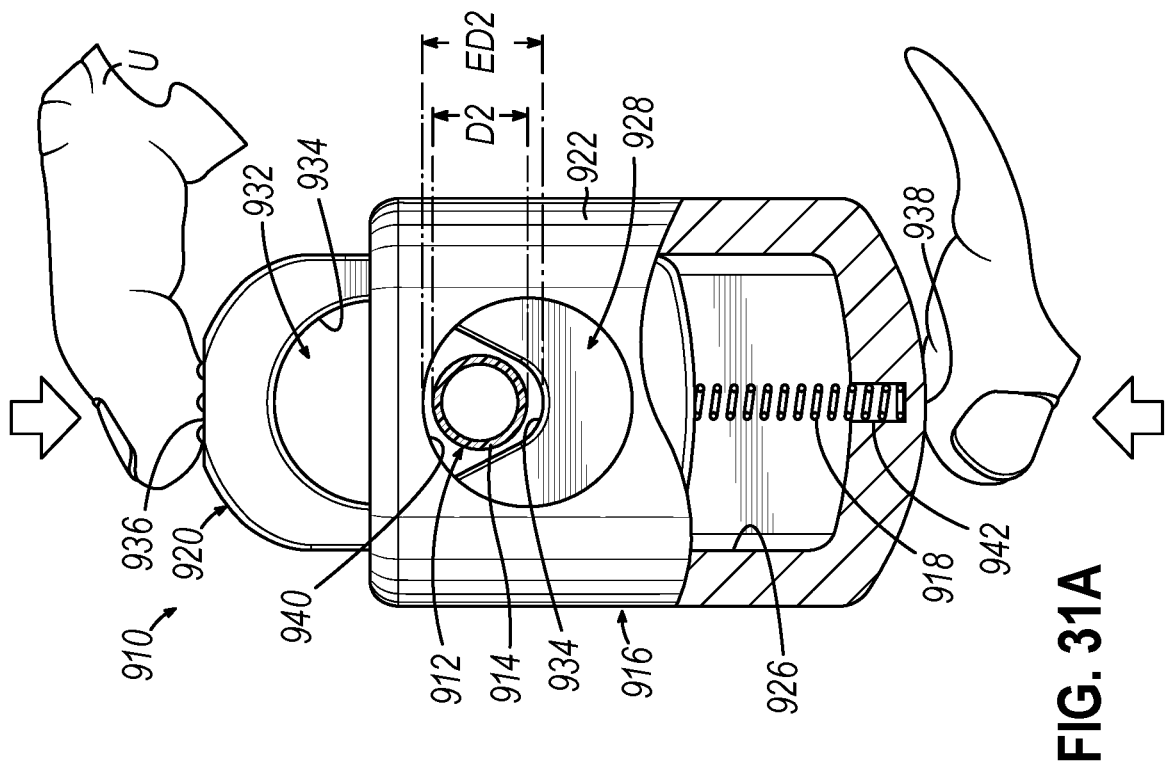
FIG. 31A depicts a partial top sectional view of the depth limiter of FIG. 29 coupled with a cannula tube having a second diameter shown in cross-section, where the depth limiter is in a movable configuration that allows for axial movement of the depth limiter relative to the cannula tube when actuated by a user.

Depth limiter (910) may be movable by the user (U) between a movable configuration shown in FIG. 31A and a fixed configuration shown in FIG. 31B. In other words, depth limiter (910) may be selectively actuated from the fixed configuration having a first effective diameter (ED1) to the movable configuration having a second effective diameter (ED2) to decouple depth limiter (910) from cannula tube (124). Additionally, depth limiter (910) may be movable by the user (U) from the movable configuration to the fixed configuration to couple depth limiter (910) to cannula tube (124). Particularly, FIG. 31A shows a partial top sectional view of depth limiter (910) of FIG. 29 coupled with a cannula tube (124) having a second diameter (D2) shown in cross-section, where depth limiter (910) is in the movable configuration.

In the movable configuration, aperture (930) of upper housing portion (922) and aperture (932) of slidable member (920) collectively form second effective diameter (ED2) that allows for axial movement of depth limiter (910) relative to cannula (912). In other words, in the movable configuration of FIG. 31A, gripping surfaces (934, 940) collectively form the second effective diameter (ED2) that allows for axial movement of depth limiter (910) relative to an outer diameter of cannula tube (124) of cannula (120). In other words, actuation of user contact portions (936, 938) is configured to respectively cause biasing features (918, 820) to bias gripping surfaces (934, 940) radially outward to selectively disengage cannula (120) in the movable configuration. As shown, user contact portions (936, 938) are configured to be actuated by the user (U) using thumb and index fingers. However, the user (U) may depress user contact portions (936, 938) in other ways (e.g., using one or more fingers and the palm).

FIG. 31B shows a top plan view of depth limiter (910) and cannula tube (124) of FIG. 31A with cannula tube (124) shown in cross-section, but with depth limiter (910) in the fixed configuration similar to FIG. 30. In the fixed configuration, gripping surfaces (934, 940) collectively form a first effective diameter (ED1) that restricts axial movement of depth limiter (910) relative to cannula (120) by directly contacting cannula (120). First effective diameter (ED1) defined by gripping surfaces (934, 940) is smaller than the outer diameter of cannula tube (124) when biasing feature (918) is in the fixed configuration. The fixed configuration may be considered the resting configuration.

Depth limiter (910) may be reusable or disposable. For example, depth limiter (910) may be injection molded for an inexpensive disposable model. For example, depth limiter (910) may be formed from a polymeric material (e.g., plastic). Alternatively, depth limiter (910) may be metal-injection molded for a re-usable model. Depth limiter (910) may sterilized using an autoclave, so that steam may enter depth limiter (910) or by completely sealing the depth limiter (910). Additionally, in some versions, depth limiter (910) may be modified for more effective stamping, machining, and welding processes. In some versions, depth limiter (910) may be completely formed of metal. Depth limiter (910) may be made from four components, shown as biasing feature (918), and slidable member (920), upper housing portion (922), and lower housing portion (924).

I. Ninth Exemplary Depth Limiter

Figure 32:
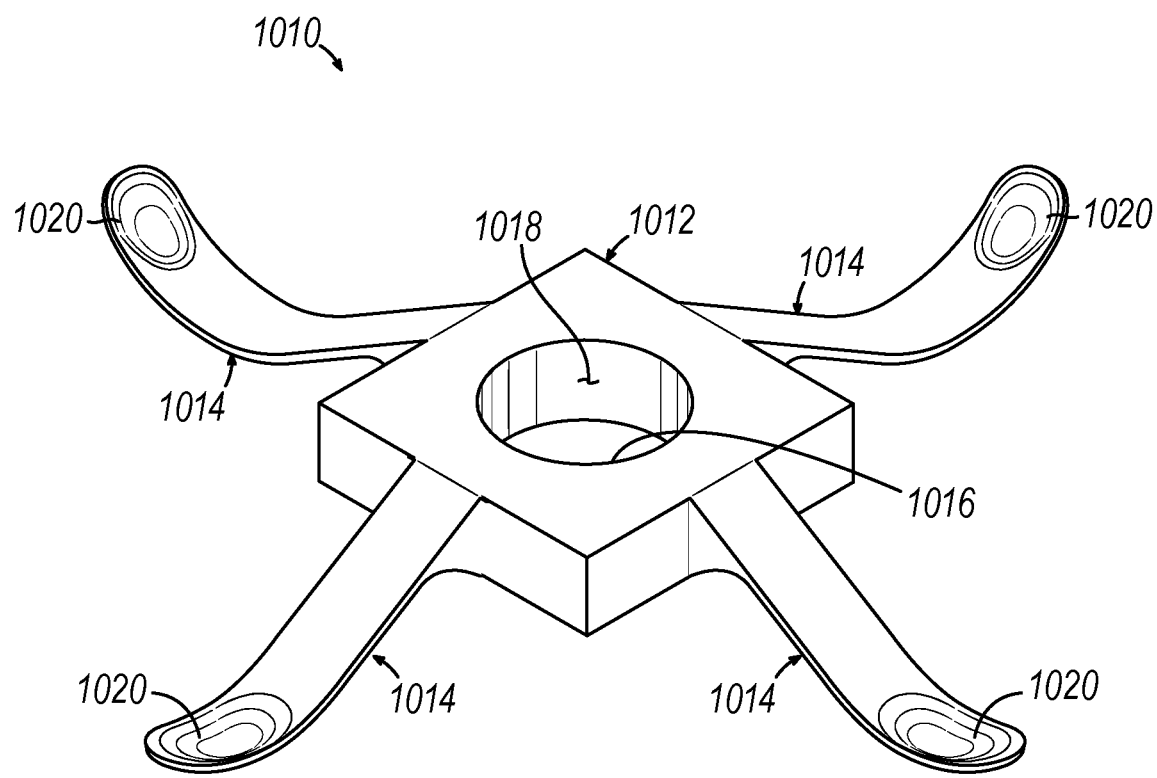
FIG. 32 depicts a perspective view of a ninth exemplary depth limiter that includes four legs.

FIG. 32 shows a perspective view of a ninth exemplary depth limiter (1010). Depth limiter (1010) includes a hub (1012) and a plurality of legs (1014). Depth limiter (1010) may be used in combination with depth limiters (210, 310, 410, 510, 610, 710, 810, 910) described above. While hub (1012) is shown as being generally square shaped, other shapes of hub (1012) are also envisioned. While FIGS. 32-33B describe depth limiter (1010) with reference to cannula tube (22) of trocar (10) of FIG. 1, cannula tube (124, 416, 616) of cannula (120, 412, 612) may also be used. As shown, hub (1012) includes an aperture (1016) extending completely therethrough. Aperture (1016) may include a gripping surface (1018). Gripping surface (1018) may extend parallel to a longitudinal axis defined by cannula tube (22) of cannula (20). Gripping surface (1018) may be smooth or non-smooth. As shown in FIG. 32, gripping surface (1018) includes a smooth surface that may frictionally engage a portion of cannula (20), such as ribs (26). Alternatively, gripping surface (1018) may include a non-smooth surface may include one or more features to lockingly engage cannula tube (22). In other words, depth limiter (1010) may be secured to cannula (20) with mating threads (like a nut) or secured to a scalloped cannula with an appropriate amount of interference fit. Such threads of depth limiter (1010) may be helical or non-helical (e.g., scallops). For example, gripping surface (1018) may include at least one tooth configured to lockingly engage with at least one of rib (26) of cannula (20).

Legs (1014) may have a generally constant cross-sectional area moving radially away from hub (1012); however, legs (1014) may have a non-uniform cross-section. For example, one or more ends of legs (1014) may include cupped portions (1020) to distribute the downward force. As shown, legs (1014) are separated by approximately 90 degrees. More or fewer legs (1014) are also envisioned.

Depth limiter (1010) may provide additional stability to the trocar (10) for anti-tip resistance. Depth limiter (1010) may be configured to restrict sudden tilting using legs (1014), thereby stabilizing cannula (20). Depth limiter (1010) is configured to prevent accidental over-insertion into body, while also restricting the displacement and/or velocity of off-axis tilting of trocar (10) to stabilize trocar (10, 110). This stabilization may be achieved using mechanical spring effects of each leg (1014). Legs (1014) may have a reduced mass allowing legs (1014) to flex outwardly, causing a variable amount of spring-resistance in each direction trocar (10) attempts to tilt. For example, legs (1014) may have reduced mass portions (e.g., living hinge portions), and/or may rely on inherent spring force of legs (1014). Legs (1014) may contact the patient's body wall to prevent or at least decelerate tip over of cannula (20).

Figure 33A:
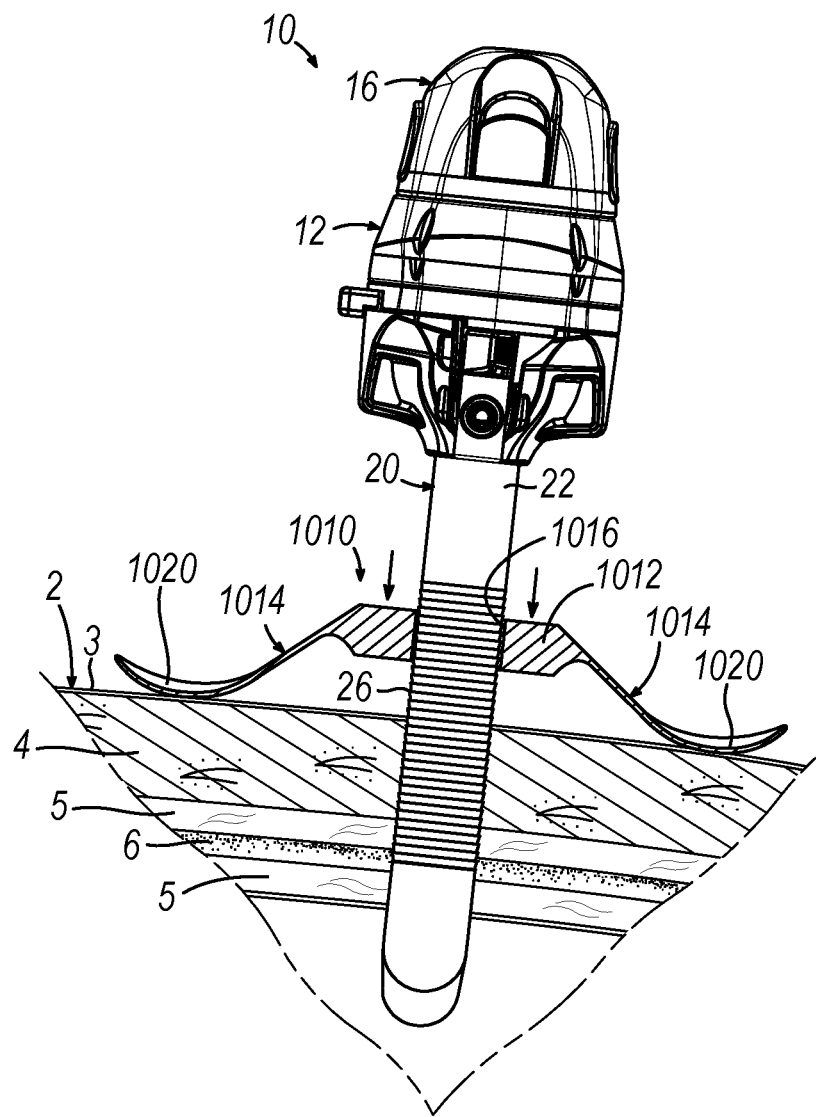
FIG. 33A depicts a partial side sectional view of the depth limiter of FIG. 32 coupled with the cannula tube of the cannula assembly of the trocar of FIG. 1, where the legs of the depth limiter are in a non-deployed configuration when the distal end of the trocar received within the abdominal cavity.
Figure 33B:
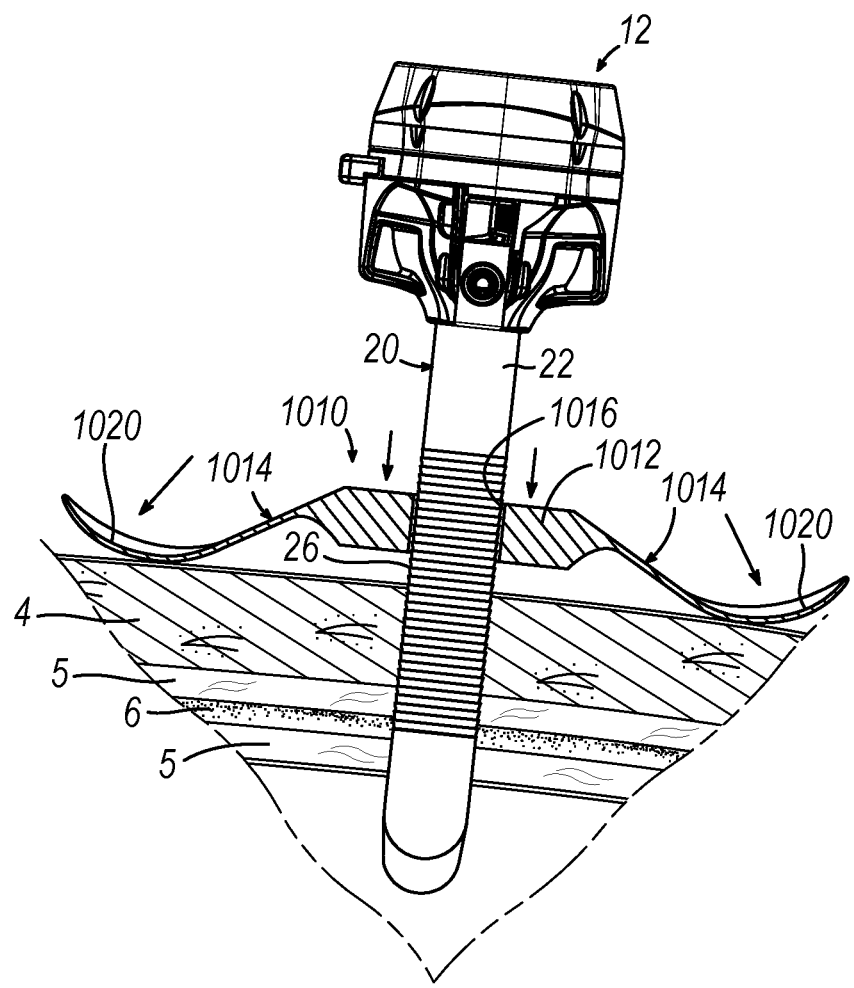
FIG. 33B depicts a partial side sectional view of the depth limiter of FIG. 32 coupled with the cannula tube of the cannula assembly of FIG. 1 following detachment and removal of the obturator, where the legs of the depth limiter are in a deployed configuration with a distal end of the cannula tube received within the abdominal cavity.

FIGS. 33A-33B show depth limiter (1010); however, the teachings of FIGS. 33A-33B may also apply to depth limiters (1110, 1210) described in detail below. FIG. 33A shows a partial side sectional view of depth limiter (1010) of FIG. 32 coupled with cannula tube (22) of cannula assembly (12) of trocar (10) of FIG. 1, where legs (1014) of depth limiter (1010) are in a non-deployed configuration when distal end of trocar (10) is received within abdominal cavity (1). In the non-deployed configuration (e.g., the resting configuration) of FIG. 33A, legs (1014) may be curved downwardly. As depth limiter (1010) is pushed against abdominal wall (2), legs (1014) bend flatter and provide reaction spring-forces against abdominal wall (2) and cannula (20). The degree at which legs (1014) bend flatter may be controlled by the user. For example, additional force (e.g., downward hand pressure by the user) may cause legs (1014) to bend flatter until depth limiter (1010) is disposed adjacent to abdominal wall (2). As the flatness of legs (1014) increases, the amount of reactive forces on cannula (20) may also increase, which increases the locking force. For example, when the user has depressed depth limiter (1010) to a partially (but not fully) deployed configuration, legs (1014) may have some degree of deployment. Additionally, if the user then applies an off-axis loading, one or more of legs (1014) may depress further than the other legs (1014), but upon removal of the off-axis load, legs (1014) may be equalized and return in a controlled manner to a centered home position.

FIG. 33B shows a partial side sectional view of depth limiter (1010) of FIG. 32 coupled with cannula tube (22) of cannula assembly (12) of FIG. 1 following detachment and removal of obturator (16), where legs (1014) of depth limiter (1010) are in a deployed configuration with a distal end of cannula tube (22) received within abdominal cavity (1). In the deployed configuration, legs (1014) may reduce the amount of rotational displacement/tilt that trocar (10) may achieve, and may also reduce the velocity that trocar (10) may achieve that tilt (i.e., preventing sudden accidental moves within the body). To completely undeploy depth limiter (1010) from cannula (12), the user may retract cannula tube (22) out of abdominal wall (2) to sufficiently reduce the compressive/clamping forces of depth limiter (1010) on the abdominal wall (2), such that the user may pull the depth limiter (1010) back using their hand. Depth limiter (1010) may be disposable or re-usable.

J. Tenth Exemplary Depth Limiter

Figure 34:
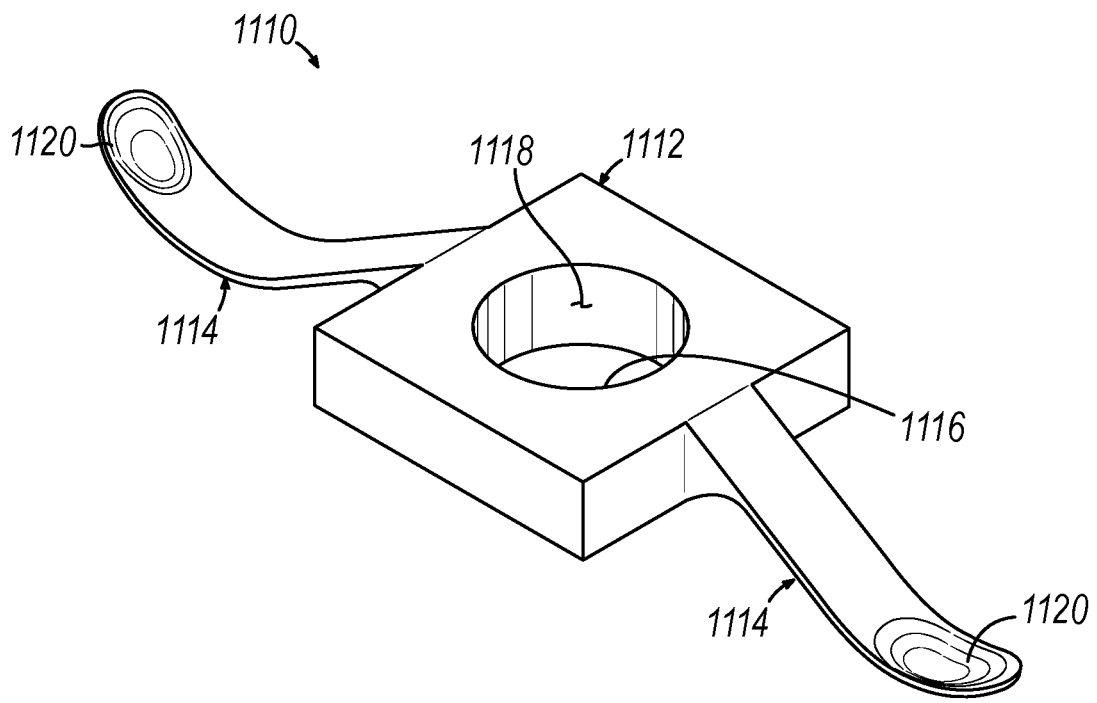
FIG. 34 depicts a perspective view of a tenth exemplary depth limiter that includes two legs.

FIG. 34 shows a tenth exemplary depth limiter (1110) that is similar to depth limiter (1010). Depth limiter (1110) includes a hub (1112) similar to hub (1012), legs (1114) similar to legs (1014), an aperture (1116) similar to aperture (1016), a gripping surface (1118) of aperture (1116) similar to gripping surface (1018). Legs (1114) may include cupped portions (1120) similar to cupped portions (1020). Unlike depth limiter (1010) that is shown as including four legs (1014), depth limiter (1110) includes two legs (1114). For example, legs (1114) may be separated by approximately 180 degrees. Legs (1114) flex similar to legs (1014) shown above with reference to FIGS. 33A-33B.

K. Eleventh Exemplary Depth Limiter

Figure 35:
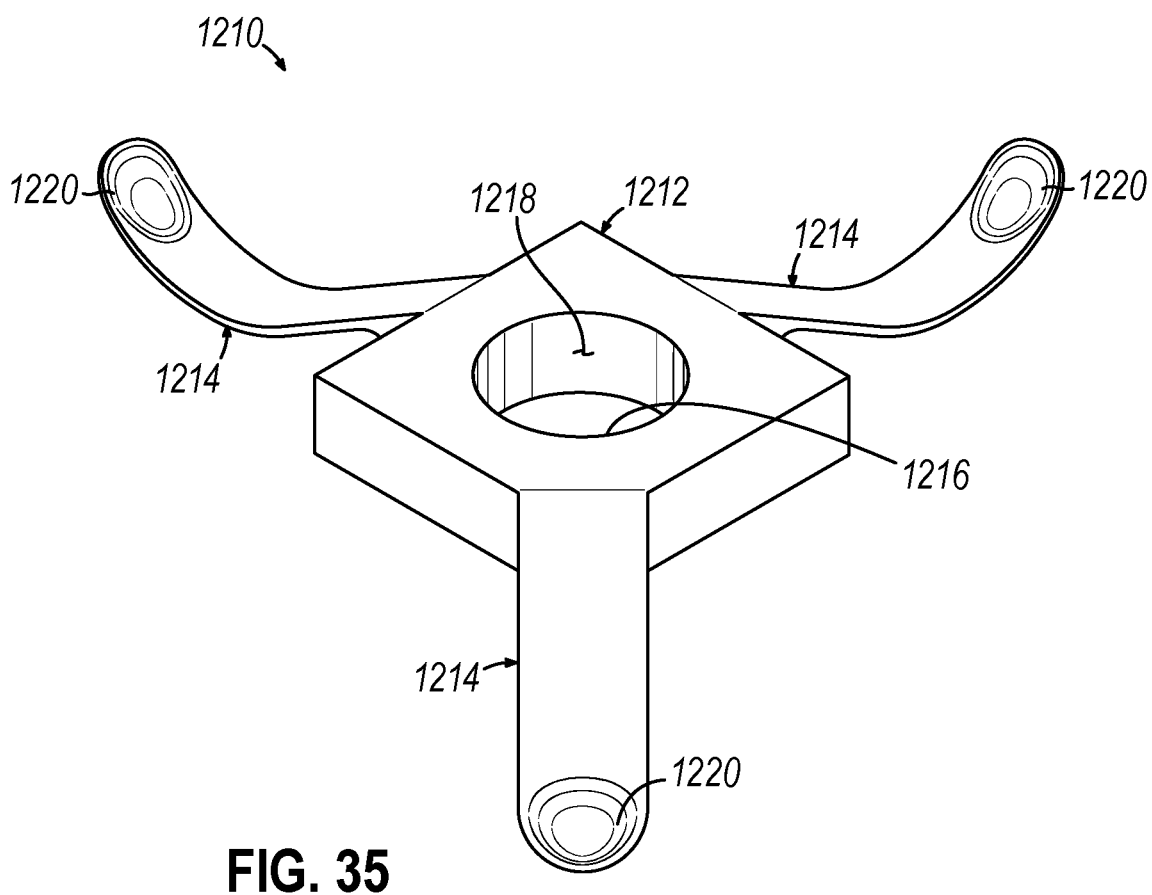
FIG. 35 depicts a perspective view of an eleventh exemplary depth limiter that includes three legs.

FIG. 35 shows an eleventh exemplary depth limiter (1210) that is similar to depth limiters (1010, 1110). Depth limiter (1210) includes a hub (1212) similar to hub (1012), legs (1214) similar to legs (1014), an aperture (1216) similar to aperture (1016), a gripping surface (1218) of aperture (1216) similar to gripping surface (1018). Legs (1114) may include cupped portions (1220) similar to cupped portions (1020). Unlike depth limiter (1010) that is shown as including four legs (1014), depth limiter (1210) includes three legs (1214). For example, legs (1214) may be circumferentially separated uniformly by approximately 120 degrees around hub (1212). However, legs (1214) may be non-uniformly separated. In some instances, the use of three or four legs (1014, 1214, 1314, 1414) may allow for further stability and ergonomics to allow for finger grip of user (U). Legs (1214) may flex similar to legs (1014) shown above with reference to FIGS. 33A-33B.

L. Twelfth Exemplary Depth Limiter

Figure 36:
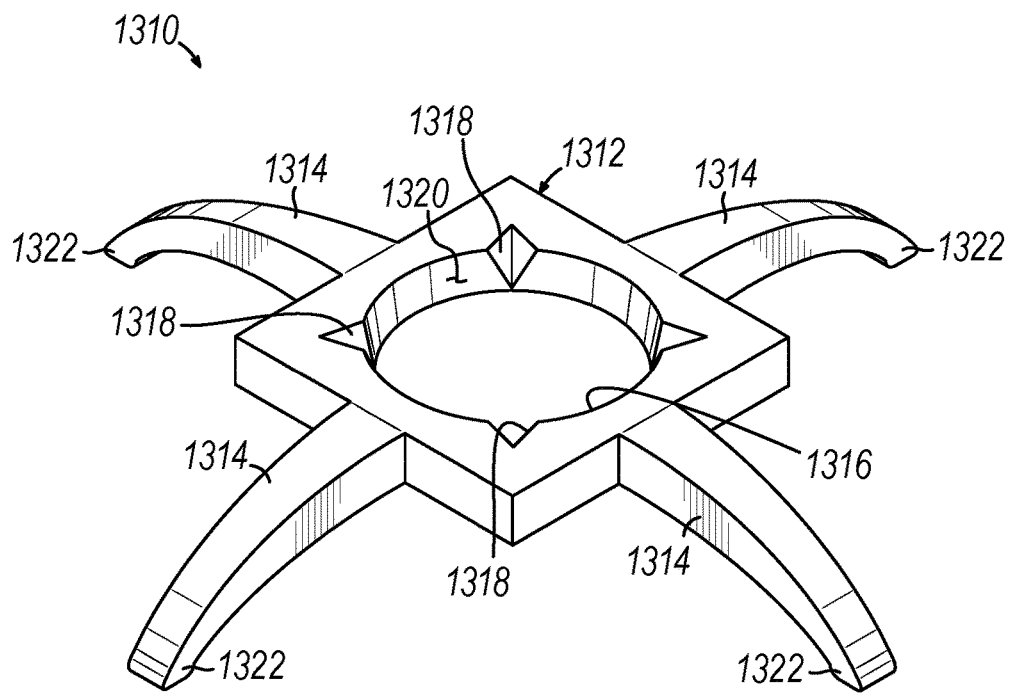
FIG. 36 depicts a perspective view of a twelfth exemplary depth limiter that includes a hub with notches.

FIGS. 36-38B show a twelfth exemplary depth limiter (1310). Particularly, FIG. 36 shows a perspective view of depth limiter (1310). As shown, depth limiter (1310) includes a hub (1312) and a plurality of legs (1314). extending from hub (1312). Depth limiter (1310) may be used in combination with any one or more of depth limiters (210, 310, 410, 510, 610, 710, 810, 910) described above. While hub (1312) is shown as being generally cylindrically shaped, other shapes of hub (1312) are also envisioned. As shown, hub (1312) includes an aperture (1316) and a plurality of notches (1318). Notches (1318) may transform depth limiter (1310) from a movable configuration to a fixed configuration.

Aperture (1316) includes a gripping surface (1320) that is configured to couple with the outer surface of cannula tube (124) in the fixed configuration. Gripping surface (1320) may extend parallel to a longitudinal axis defined by cannula tube (124) of cannula (120). Gripping surface (1320) may be smooth or non-smooth. As shown in FIG. 36, gripping surface (1320) may include a smooth surface that frictionally engages ribs (128) of cannula (120) in the fixed configuration. Alternatively, gripping surface (1320) may include a non-smooth surface may include one or more features to lockingly engage cannula tube (124). Hub (1312) of depth limiter (1310) may be secured to cannula (120) with mating threads (like a nut) or may be secured to a scalloped cannula using an interference fit. Threads may be helical or non-helical (e.g., scallops). For example, gripping surface (1320) may include at least one tooth configured to lockingly engage with at least one of rib (128) of cannula (120). For example, notches (1318) may be formed in hub (1312) of depth limiter (1310), such that each leg (1314) may selectively collapse when adequate force acts on that leg (1314), causing gripping surface (1320) to clamp down tighter on cannula (120). As such, depth limiter (1310) may limit insertion depth of cannula tube (124) of cannula (120) and provide stability control of cannula tube (124) of cannula (120).

Legs (1314) may have a generally tapering cross-section moving radially away from hub (1312). For example, one or more ends of legs (1314) may include distal pad (1322) to distribute the downward force. As shown, legs (1314) are separated by approximately 90 degrees. Legs (1314) may be non-uniformly separated. Additionally, more or fewer legs (1314) are also envisioned (similar to those shown in FIGS. 34-35 associated with depth limiters (1110, 1210). Depth limiter (1310) may provide additional stability to the trocar (110) for anti-tip resistance. Depth limiter (1310) may be configured to restrict sudden tilting using legs (1314), thereby stabilizing cannula (120). Legs (1314) may contact body wall to prevent or at least decelerate tip over of cannula (120). While FIGS. 37A-38B describe depth limiter (1310) with reference to cannula tube (124) of trocar (110), cannula tube (22, 416, 616) of cannula (20, 412, 612) may also be used.

Figure 37A:
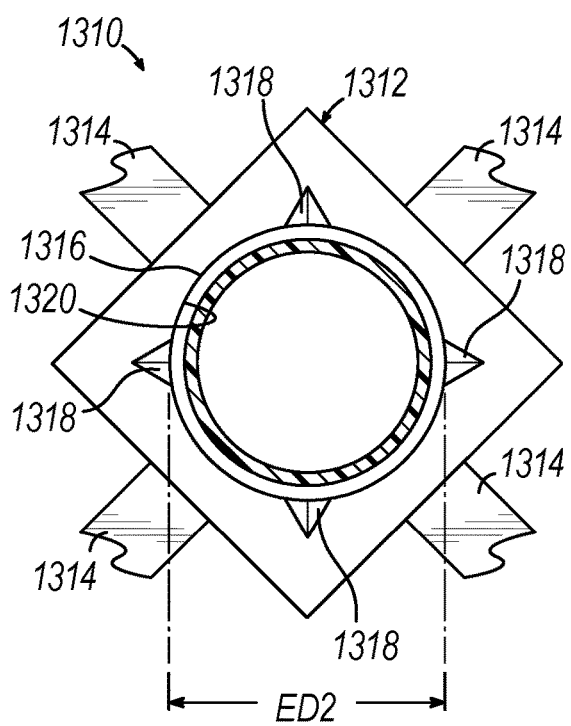
FIG. 37A depicts a top plan view of the depth limiter of FIG. 36 coupled with the cannula tube of the cannula assembly of FIG. 5, where the hub of the depth limiter is in a movable configuration.
Figure 38A:
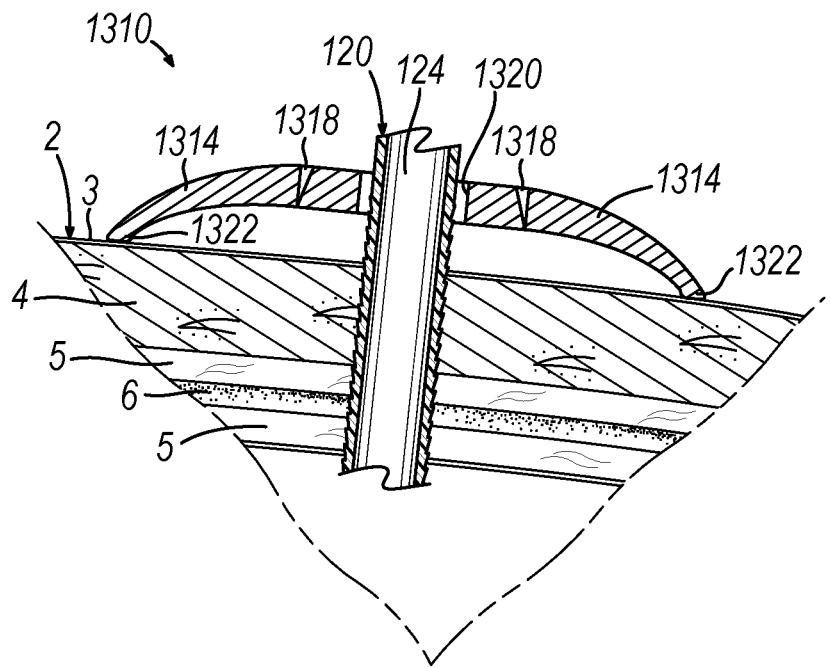
FIG. 38A depicts a partial side sectional view of the depth limiter of FIG. 36 coupled with the cannula tube of the cannula assembly of FIG. 5, where the legs of the depth limiter are in a deployed configuration.

FIGS. 37A and 38A show depth limiter (1310) in the movable configuration. Particularly, FIG. 37A shows a top plan view of depth limiter (1310) of FIG. 36 coupled with cannula tube (124) of cannula assembly (112) of FIG. 5, where hub (1312) of depth limiter (1310) is in a movable configuration. FIG. 38A shows a partial side sectional view of depth limiter (1310) of FIG. 36 coupled with cannula tube (124) of cannula assembly (112) of FIG. 5, where legs (1314) of depth limiter (1310) are in the movable configuration. In the movable configuration of FIGS. 37A and 38A, gripping surface (1320) forms a second effective diameter (ED2) that allows for axial movement of depth limiter (1310) relative to an outer diameter of cannula tube (124) of cannula (112). In the movable configuration, also considered the resting configuration, legs (1314) are curved downwardly. Once pushed against abdominal wall (2), legs (1314) bend flatter and provide a reaction force against abdominal wall (2) and cannula (120).

Figure 37B:
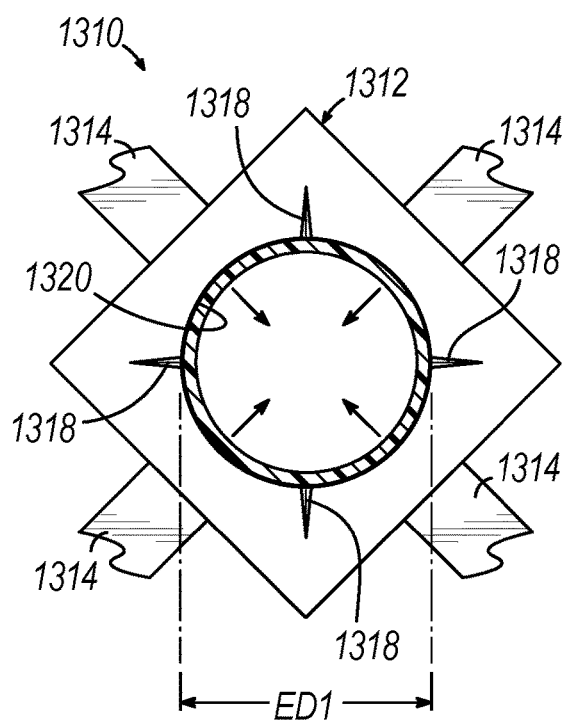
FIG. 37B depicts a partial side sectional view of the depth limiter of FIG. 36 coupled with the cannula tube of the cannula assembly of FIG. 5 following detachment and removal of the obturator, where the legs of the depth limiter are in a fixed configuration.
Figure 38B:
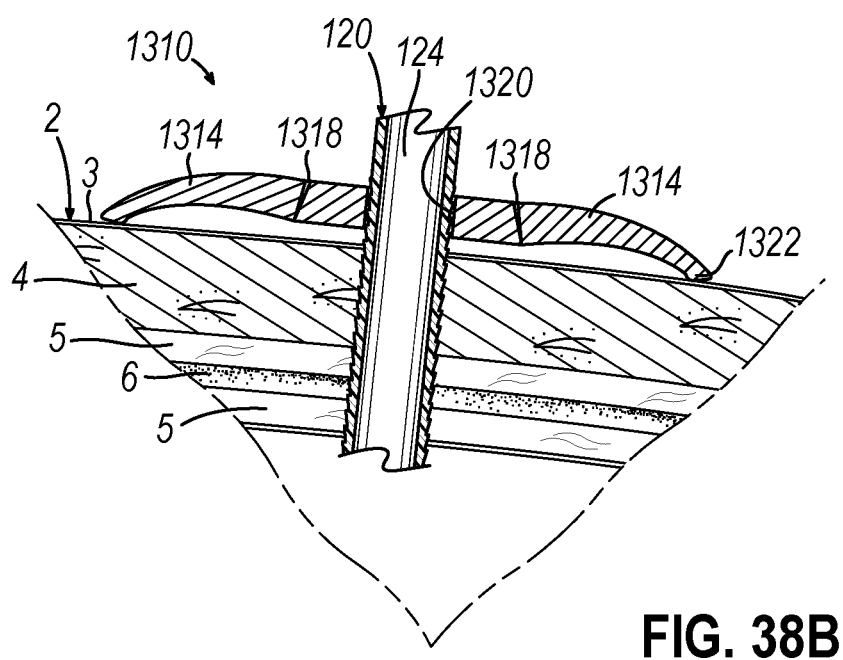
FIG. 38B depicts a partial side sectional view of the depth limiter of FIG. 36 coupled with the cannula tube of the cannula assembly of FIG. 5 following detachment and removal of the obturator, where the legs of the depth limiter are in a deployed configuration.

FIGS. 37B and 38B show depth limiter (1310) in the fixed configuration. Particularly, FIG. 37B shows a partial side sectional view of depth limiter (1310) of FIG. 36 coupled with cannula tube (124) of cannula assembly (112) of FIG. 5 following detachment and removal of obturator (116), where legs (1314) of depth limiter (1310) are in the fixed configuration. FIG. 38B shows a partial side sectional view of depth limiter (1310) of FIG. 36 coupled with cannula tube (124) of cannula assembly (112) of FIG. 5 following detachment and removal of obturator (116), where legs (1314) of depth limiter (1310) are in the fixed configuration. In the fixed configuration, notches (1318) may be forced closed to narrow aperture (1316). Legs (1314) may reduce the amount of rotational displacement/tilt that trocar (110) may exhibit, and may also reduce the velocity at which trocar (110) may assume that tilt (i.e., preventing sudden movements within the body). In the fixed configuration, gripping surfaces (1320) collectively form a first effective diameter (ED1) that restricts axial movement of depth limiter (1310) relative to cannula (120) by directly contacting cannula (120). Depth limiter (1310) may be disposable or reusable.

M. Thirteenth Exemplary Depth Limiter

Figure 39:
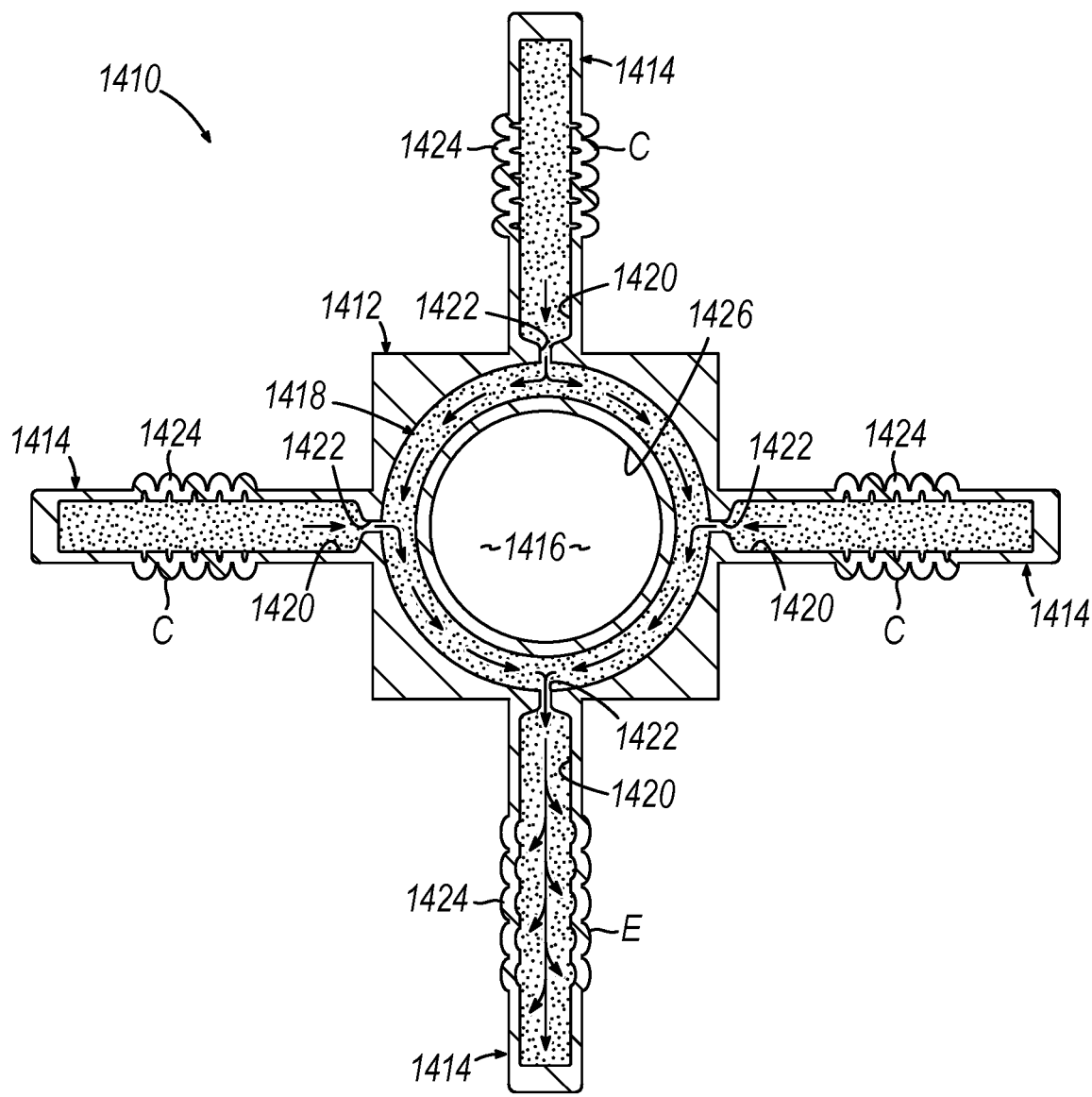
FIG. 39 depicts a top sectional view of a thirteenth exemplary depth limiter that includes a fluid chamber and four legs.

FIG. 39 shows a top sectional view of a thirteenth exemplary depth limiter (1410). Depth limiter (1410) includes a hub (1412) and a plurality of legs (1414) extending from hub (1412). Depth limiter (1410) may be used in combination with any one or more of depth limiters (210, 310, 410, 510, 610, 710, 810, 910) described above. In some versions, hub (1412) may being generally cylindrically shaped. As shown, hub (1412) includes an aperture (1416) configured to receive cannula tube (124) of cannula (120). As shown, legs (1414) may be separated by approximately 90 degrees. However, legs (1414) may be non-uniformly separated. Additionally, more or fewer legs (1414) are also envisioned, similar to depth limiters (1110, 1210) shown in FIGS. 34-35.

Depth limiter (1410) includes a fluid chamber (1418) that may be disposed within hub (1412) and legs (1414). For example, fluid chamber (1418) may be completely enclosed by hub (1412) and legs (1414). Fluid chamber may include a plurality of fluid passageways (1420) that include narrow portions (1422). Narrow portions (1422) may be disposed generally between hub (1412) and legs (1414). Narrow portions (1422) regulate flow between hub (1412) and legs (1414). In other words, fluid chamber (1418) may be integrated into legs (1414) with narrow portions (1422) forming restricted areas of flow at the base of each leg (1414). As shown, one or more ends of legs (1414) may include extensive portion (1424) configured to extend from a compressed configuration (C) to an expanded configuration (E). Depth limiter (1410) may provide additional stability to the trocar (110) for anti-tip resistance. As additional tilt force acts on each independent leg (1414), the fluid may redistribute to the other legs (1414), but the fluid may be restricted by these restricted areas (1422), thus creating a damping effect on the tilting of trocar (110). This damping effect may regulate the speed at which trocar (110) tilts. As a result, depth limiter (1410) may restrict sudden tilting of trocar (110) via restricted fluid flow between legs (1414), thereby stabilizing cannula (120).

Aperture (1416) includes a gripping surface (1426) that may couple with the outer surface of cannula tube (124) of cannula (120). Gripping surface (1426) may extend parallel to a longitudinal axis defined by cannula tube (124) of cannula (120). Gripping surface (1426) may be smooth or non-smooth. As shown in FIG. 39, gripping surface (1426) may include a smooth surface that frictionally engages ribs (128) of cannula (120). Alternatively, gripping surface (1426) may include a non-smooth surface may include one or more features to lockingly engage cannula tube (124). For example, hub (1412) of depth limiter (1410) may be secured to cannula (120) using mating threads (like a nut) or secured to a scalloped cannula. Threads may be helical or non-helical (e.g., scallops). For example, gripping surface (1426) may include at least one tooth configured to lockingly engage with at least one of rib (128) of cannula (120). Depth limiter (1410) may be disposable.

N. Exemplary Method

A method of inserting a surgical access device (e.g., trocar 10, 110) through a body wall (e.g., abdominal wall (2)) of a patient is also described. Trocar (10, 110) includes a cannula (20, 120, 412, 612, 912), an obturator (16, 116), and one or more of depth limiters (210, 310, 410, 510, 610, 710, 810, 910, 1010, 1110, 1210, 1310, 1410).

The method includes coupling depth limiter (210, 310, 410, 510, 610, 710, 810, 910, 1010, 1110, 1210, 1310, 1410) with cannula tube (22, 124, 416, 616) of cannula (20, 120, 412, 612). This coupling may be obtained by the user (U) actuating user contact portions (224, 232, 320, 322, 434, 436, 534, 536, 622, 624, 714, 716, 814, 816, 936, 938) which causes the resilient portion including gripping surface (256, 258, 370, 374, 458, 462, 558, 562, 654, 656, 738, 746, 840, 842, 934, 940, 1018, 1118, 1218, 1320, 1426) to move from the fixed configuration to the movable configuration.

In the fixed configuration, gripping surfaces (256, 258, 370, 374, 458, 462, 558, 562, 654, 656, 738, 746, 840, 842, 934, 940, 1320) may collectively form a first effective diameter (ED1) that restricts axial movement of depth limiter (210, 310, 410, 510, 610, 710, 810, 910, 1310) relative to cannula (20, 120, 412, 612) by directly contacting cannula (20, 120, 412, 612). In the movable configuration, gripping surfaces (256, 258, 370, 374, 458, 462, 558, 562, 654, 656, 738, 746, 840, 842, 934, 940, 1320) collectively form a second effective diameter (ED2) that allows for axial movement of depth limiter (210, 310, 410, 510, 610, 710, 810, 910, 1310) relative to cannula (20, 120, 412, 612, 912).

The method also includes inserting a least a portion of cannula tube (22, 124, 416, 616, 914) of cannula (20, 120, 412, 612, 912) into the patient. Depth limiters (210, 310, 410, 510, 610, 710, 810, 910, 1010, 1110, 1210, 1310, 1410) may be moved along cannula (20, 120, 412) once cannula (20, 120, 412) is within the body by user again actuating user contact portion (224, 232, 320, 322, 434, 436, 534, 536, 622, 624, 714, 716, 814, 816, 936, 938) which causes the resilient portion including gripping surface (256, 258, 370, 374, 458, 462, 558, 562, 654, 656, 738, 746, 840, 842, 934, 940, 1018, 1118, 1218, 1320, 1426) to move from the fixed configuration to the movable configuration.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A depth limiter configured to couple with a cannula of a surgical access device, the depth limiter comprising: (a) first and second user contact portions configured to be actuated by a user; (b) a first biasing feature comprising: (i) a first resilient portion, and (ii) a first gripping surface, wherein the first gripping surface is movably coupled with the first resilient portion, wherein the first resilient portion is configured to move the first gripping surface from a fixed configuration to a movable configuration when the first user contact portion is actuated by the user; and (c) a second biasing feature comprising: (i) a second resilient portion, and (ii) a second gripping surface, wherein the second gripping surface is movably coupled with the second resilient portion, wherein the second resilient portion is configured to move the second gripping surface from the fixed configuration to the movable configuration when the second user contact portion is actuated by the user, wherein in the fixed configuration, the first and second gripping surfaces collectively form a first effective diameter that is configured to restrict axial movement of the depth limiter relative to the cannula by directly contacting the cannula, and wherein in the movable configuration, the first and second gripping surfaces extend parallel to a longitudinal axis defined by the cannula and collectively form a second effective diameter that is configured to allow for axial movement of the depth limiter relative to the cannula.

Example 2

The depth limiter of Example 1, wherein the first resilient portion is affixed to the first gripping surface, wherein the second resilient portion is affixed to the second gripping surface.

Example 3

The depth limiter of any of the preceding Examples, wherein the first resilient portion is integrally formed together as a unitary piece together with the first gripping surface, wherein the second resilient portion is integrally formed together as a unitary piece together with the second gripping surface.

Example 4

The depth limiter of any of the preceding Examples, wherein the first gripping surface is radially offset from the first user contact portion by approximately 90 degrees, wherein the second gripping surface is radially offset from the second user contact portion by approximately 90 degrees.

Example 5

The depth limiter of any of the preceding Examples, wherein the first and second gripping surfaces do not completely surround the cannula in either the fixed configuration or the movable configuration.

Example 6

The depth limiter of any of the preceding Examples, wherein the first gripping surface is configured to contact the cannula at a first discrete region, wherein the second gripping surface is configured to contact the cannula at a second discrete region that is spaced from the first discrete region.

Example 7

The depth limiter of any of the preceding Examples, wherein the first and second gripping surfaces are disposed circumferentially opposite one another and are configured to directly contact circumferentially opposite sides of the cannula in the fixed configuration.

Example 8

The depth limiter of any of the preceding Examples, wherein the first and second gripping surfaces are spaced apart from one another in both of the fixed and movable configurations.

Example 9

The depth limiter of any of the preceding Examples, wherein the cannula includes a plurality of tissue gripping features, wherein at least one of the first and second gripping surfaces includes a smooth surface that is configured to frictionally engage the tissue gripping features of the cannula in the fixed configuration and not frictionally engage the tissue gripping features of the cannula in the movable configuration.

Example 10

The depth limiter of any one or more of Examples 1 through 8, wherein the cannula includes a plurality of tissue gripping features, wherein at least one of the first and second gripping surfaces includes at least one engagement feature configured to lockingly engage with at least one of the tissue gripping features of the cannula in the fixed configuration and not lockingly engage with the tissue gripping features of the cannula in the movable configuration.

Example 11

The depth limiter of any one or more of Examples 1 through 8, wherein the cannula includes a plurality of tissue gripping features, wherein at least one of the first and second gripping surfaces includes a plurality of engagement features configured to lockingly engage with the tissue gripping features of the cannula in the fixed configuration and not lockingly engage with the tissue gripping features of the cannula in the movable configuration.

Example 12

The depth limiter of any of the preceding Examples, wherein the first resilient portion includes first and second biasing arms that are disposed opposite one another, wherein the second resilient portion includes first and second biasing arms that are disposed opposite one another.

Example 13

The depth limiter of any of the preceding Examples, wherein the first and second user contact portions that are disposed circumferentially opposite one another.

Example 14

The depth limiter of any of the preceding Examples, wherein the depth limiter is integrally formed together as a unitary piece.

Example 15

The depth limiter of any of the preceding Examples, further comprising a housing that surrounds the at least one biasing feature while exposing the first and second user contact portions.

Example 16

A depth limiter configured to couple with a cannula of a surgical access device, the depth limiter comprising: (a) a housing comprising: (i) a slot, and (ii) an aperture extending through the housing, wherein the aperture communicates with the slot, wherein the aperture extends along a longitudinal axis; (b) a biasing feature disposed at least partially within the slot; and (c) a slidable member disposed at least partially within the slot, wherein the slidable member includes an aperture extending therethrough, wherein the slidable member is movably coupled with the biasing feature between a fixed configuration and a movable configuration, wherein in the fixed configuration, the apertures of the housing and the slidable member are at least partially aligned to collectively form a first effective diameter such that the slidable member and the housing are configured to restrict axial movement of the depth limiter relative to the cannula, wherein in the movable configuration, the apertures of the housing and the slidable member collectively form a second effective diameter such that the slidable member and the housing are configured to allow for axial movement of the depth limiter relative to the cannula.

Example 17

The depth limiter of Example 16, wherein the aperture of the slidable member has an oblong shape that is configured to accommodate cannulas having different diameters in both the fixed and movable configurations.

Example 18

A surgical access device assembly comprising: (a) a cannula, wherein the cannula includes a working channel configured to guide a surgical instrument along a central axis of the cannula; and (b) a depth limiter comprising: (i) first and second user contact portions configured to be actuated by a user; (ii) a first biasing feature comprising: (A) a first resilient portion, and (B) a first gripping surface, wherein the first gripping surface is movably coupled with the first resilient portion, wherein the first resilient portion is configured to move the first gripping surface from a fixed configuration to a movable configuration when the first user contact portion is actuated by the user; and (iii) a second biasing feature comprising: (A) a second resilient portion, and (B) a second gripping surface, wherein the second gripping surface is movably coupled with the second resilient portion, wherein the second resilient portion is configured to move the second gripping surface from the fixed configuration to the movable configuration when the second user contact portion is actuated by the user, wherein in the fixed configuration, the first and second gripping surfaces collectively form a first effective diameter that is configured to restrict axial movement of the depth limiter relative to the cannula by directly contacting the cannula, and wherein in the movable configuration, the first and second gripping surfaces extend parallel to a longitudinal axis defined by the cannula and collectively form a second effective diameter that is configured to allow for axial movement of the depth limiter relative to the cannula.

Example 19

The surgical access device assembly of Example 18, wherein the resilient portion is integrally formed together as a unitary piece together with the first and second gripping surfaces.

Example 20

The surgical access device assembly of any one or more of Examples 18 through 19, further comprising an obturator, wherein the obturator is configured to removably couple with the cannula along the central axis to facilitate insertion of the surgical access device through a body wall of the patient.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,304, entitled "Multi-Diameter Cannula Depth Limiter," filed on even date herewith, published as U.S. Pub. No. 2021/0338281 on Nov. 4, 2021; U.S. patent application Ser. No. 17/213,401, entitled "Pinch-To-Clamp Cannula Depth Limiter," filed on even date herewith, published as U.S. Pub. No. 2021/0338273 on Nov. 4, 2021; U.S. patent application Ser. No. 17/213,409, entitled "Universal Size Multi-Walled Elastomer Cannula Depth Limiter," filed on even date herewith, published as U.S. Pub. No. 2021/0338282 on Nov. 4, 2021; U.S. patent application Ser. No. 17/213,415, entitled "Threaded Cannula Depth Limiter," filed on even date herewith, published as U.S. Pub No. 2021/0338274 on Nov. 4, 2021; U.S. patent application Ser. No. 17/213,426, entitled "Tilting Tang Cannula Depth Limiter," filed on even date herewith, published as U.S. Pub. No. 2021/0338283 on Nov. 4, 2021; U.S. patent application Ser. No. 17/213,431, entitled "Two Piece Separable Obturator," filed on even date herewith, published as U.S. Pub. No. 2021/0338275 on Nov.

4, 2021; U.S. patent application Ser. No. 17/213,434, entitled "Latchless Obturator with Interference Fit Feature," filed on even date herewith, published as U.S. Pub. No. 2021/0338269 on Nov. 4, 2021; U.S. patent application Ser. No. 17/213,437, entitled "Balancing Feature for Reusable Trocar," filed on even date herewith, issued as U.S. Pat. No. 11,559,329 on Jan. 24, 2023; U.S. patent application Ser. No. 17/213,508, entitled "Airflow Channels and Patterns in Lumen for Cannula," filed on even date herewith, published as U.S. Pub. No. 2021/0338278 on Nov. 4, 2021; and/or U.S. patent application Ser. No. 17/213,518, entitled "Stabilizer for Surgical Shafts or Cannulas," filed on even date herewith, published as U.S. Pub. No. 2021/0338371 on Nov. 4, 2021. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A depth limiter configured to couple with a cannula of a surgical access device, the depth limiter comprising:
   (a) first and second user contact portions configured to be actuated by a user;
   (b) a first biasing feature comprising:
      (i) a first resilient portion,
      (ii) a first gripping surface, wherein the first gripping surface is angularly offset from the first user contact portion by approximately 90 degrees, wherein the first gripping surface is movably coupled with the first resilient portion, wherein the first resilient portion is configured to move the first gripping surface from a fixed configuration to a movable configuration when the first user contact portion is actuated by the user, and
      (iii) a first arm positioned between and aligned with the first resilient portion and the first gripping surface, wherein the first arm is configured to move the first gripping surface from the fixed configuration to the movable configuration, the first arm defining a longitudinal axis that is angularly offset from the first user contact portion by approximately 90 degrees; and
   (c) a second biasing feature comprising:
      (i) a second resilient portion, and
      (ii) a second gripping surface, wherein the second gripping surface is movably coupled with the second resilient portion, wherein the second resilient portion is configured to move the second gripping surface from the fixed configuration to the movable configuration when the second user contact portion is actuated by the user, wherein in the fixed configuration, the first and second gripping surfaces collectively form a first effective diameter that is configured to restrict axial movement of the depth limiter relative to the cannula by directly contacting the cannula, and wherein in the movable configuration, the first and second gripping surfaces extend parallel to a longitudinal axis defined by the cannula and collectively form a second effective diameter that is configured to allow for axial movement of the depth limiter relative to the cannula.

2. The depth limiter of claim 1, wherein the first resilient portion is affixed to the first gripping surface, wherein the second resilient portion is affixed to the second gripping surface.

3. The depth limiter of claim 1, wherein the first and second user contact portions, the first biasing feature, and the second biasing feature are integrally formed together as a unitary piece.

4. The depth limiter of claim 1, wherein the second gripping surface is angularly offset from the second user contact portion by approximately 90 degrees, wherein the first user contact portion is angularly offset from the second user contact portion by approximately 180 degrees.

5. The depth limiter of claim 1, wherein the first and second gripping surfaces do not completely surround the cannula in either the fixed configuration or the movable configuration.

6. The depth limiter of claim 1, wherein the first gripping surface is configured to contact the cannula at a first discrete region, wherein the second gripping surface is configured to contact the cannula at a second discrete region that is spaced from the first discrete region.

7. The depth limiter of claim 6, wherein the first and second gripping surfaces are disposed circumferentially opposite one another and are configured to directly contact circumferentially opposite sides of the cannula in the fixed configuration.

8. The depth limiter of claim 1, wherein the first and second gripping surfaces are spaced apart from one another in both of the fixed and movable configurations.

9. The depth limiter of claim 1, wherein the cannula includes a plurality of tissue gripping features, wherein at least one of the first or second gripping surfaces includes a smooth surface that is configured to frictionally engage the tissue gripping features of the cannula in the fixed configuration and not frictionally engage the tissue gripping features of the cannula in the movable configuration.

10. The depth limiter of claim 1, wherein the cannula includes a plurality of tissue gripping features, wherein at least one of the first or second gripping surfaces includes at least one engagement feature configured to lockingly engage with at least one of the tissue gripping features of the cannula in the fixed configuration and not lockingly engage with the tissue gripping features of the cannula in the movable configuration.

11. The depth limiter of claim 1, wherein the cannula includes a plurality of tissue gripping features, wherein at least one of the first or second gripping surfaces includes a plurality of engagement features configured to lockingly engage with the tissue gripping features of the cannula in the fixed configuration and not lockingly engage with the tissue gripping features of the cannula in the movable configuration.

12. The depth limiter of claim 1, wherein a height of the first user contact portion is greater than a height of the first resilient portion, wherein each height of the first user contact portion and the first resilient portion is taken parallel to the longitudinal axis.

13. The depth limiter of claim 1, wherein a thickness of the first user contact portion is greater than a thickness of the first resilient portion, wherein each thickness of the first user contact portion and the first resilient portion is taken radially from the longitudinal axis.

14. The depth limiter of claim 1, the second biasing feature further comprising a second arm positioned between the second resilient portion and the second gripping surface, wherein the second arm is configured to move to move the second gripping surface from the fixed configuration to the movable configuration.

15. A surgical access device assembly comprising:
(a) a cannula having a tube defining a working channel configured to guide a surgical instrument along a central axis of the cannula; and
(b) a depth limiter comprising:
(i) first and second user contact portions configured to be actuated by a user, the first and second user contact portions being positioned on opposing sides of the cannula;
(ii) a first biasing feature comprising:
(A) a first resilient portion, and
(B) a first gripping surface movably coupled with the first resilient portion, and
(C) a first arm positioned between the first resilient portion and the first gripping surface, the first arm extending along a longitudinal axis that intersects a normal axis extending through the first user contact portion at approximately 90 degrees, wherein the first arm is configured to move the first gripping surface from a fixed configuration to a movable configuration,
(iii) a second biasing feature comprising:
(A) a second resilient portion, and
(B) a second gripping surface, movably coupled with the second resilient portion,
wherein each of the first and second gripping surfaces is angularly offset from the first user contact portion by approximately 90 degrees about the central axis,
wherein the first and second gripping surfaces are actuatable by the first and second user contact portions, respectively, between the fixed configuration and the movable configuration,
wherein in the fixed configuration, the first and second gripping surfaces collectively form a first effective diameter that is configured to restrict axial movement of the depth limiter relative to the cannula by directly contacting the tube, and
wherein in the movable configuration, the first and second gripping surfaces collectively form a second effective diameter that is configured to allow for axial movement of the depth limiter relative to the cannula.

16. The depth limiter of claim 15, wherein each of the first and second gripping surfaces extends parallel to the central axis when in the movable configuration.

17. The depth limiter of claim 15, wherein the second biasing feature further comprises:
(C) a second arm positioned between the second resilient portion and the second gripping surface, wherein the second arm is configured to move the second gripping surface from the fixed configuration to the movable configuration.

18. The depth limiter of claim 17, wherein a longitudinal axis of the second arm intersects the second gripping surface at approximately 90 degrees.

19. A depth limiter configured to couple with a cannula of a surgical access device, the depth limiter comprising:
- (a) first and second user contact portions configured to be actuated by a user, wherein the first and second user contact portions are positioned on opposing sides of the depth limiter;
- (b) a biasing portion at least partially defining an opening, wherein the first and second user contact portions are configured to transition the biasing portion between a fixed configuration and a movable configuration; and
- (c) a gripping surface positioned within the opening and aligned with the biasing portion, wherein the gripping surface is configured to couple with the cannula of the surgical access device when the biasing portion is in the fixed configuration to thereby inhibit longitudinal translation of the depth limiter along the cannula, and to decouple from the cannula when the biasing portion is in the movable configuration to allow longitudinal translation of the depth limiter along the cannula, wherein the gripping surface includes a plurality of teeth, wherein each tooth of the plurality of teeth is configured to engage a rib of the cannula of the surgical access device to thereby inhibit longitudinal translation of the depth limiter along the cannula when the biasing portion is in the fixed configuration, and wherein the biasing portion comprises an arm positioned between the first user contact portion and the second user contact portion, wherein the arm is configured to move the gripping surface from the fixed configuration to the movable configuration, and wherein a longitudinal axis through the arm intersects a normal axis extending through the first user contact portion at approximately 90 degrees.

20. The depth limiter of claim 10, wherein the longitudinal axis through the arm intersects a second normal axis extending through the second user contact portion at approximately 90 degrees.

* * * * *